(12) United States Patent
Cohen et al.

(10) Patent No.: US 10,391,143 B2
(45) Date of Patent: Aug. 27, 2019

(54) MITOCHONDRIAL-DERIVED PEPTIDE MOTS3 REGULATES METABOLISM AND CELL SURVIVAL

(71) Applicant: THE REGENTS OF THE UNIVERSITY OF CALIFORNIA, Oakland, CA (US)

(72) Inventors: Pinchas Cohen, Pacific Palisades, CA (US); Changhan Lee, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/113,996

(22) Filed: Aug. 27, 2018

(65) Prior Publication Data

US 2018/0360910 A1 Dec. 20, 2018

Related U.S. Application Data

(62) Division of application No. 15/146,249, filed on May 4, 2016, now Pat. No. 10,064,914, which is a division of application No. 14/213,617, filed on Mar. 14, 2014.

(60) Provisional application No. 61/801,474, filed on Mar. 15, 2013.

(51) Int. Cl.
| | | |
|---|---|---|
| *C07K 14/47* | (2006.01) | |
| *C07K 16/18* | (2006.01) | |
| *A61K 38/17* | (2006.01) | |
| *A61K 9/00* | (2006.01) | |

(52) U.S. Cl.
CPC ........ *A61K 38/1709* (2013.01); *A61K 9/0019* (2013.01); *C07K 14/47* (2013.01); *C07K 16/18* (2013.01)

(58) Field of Classification Search
CPC .. A61K 38/1709; A61K 9/0019; C07K 14/47; C07K 16/18
See application file for complete search history.

(56) References Cited

U.S. PATENT DOCUMENTS

| | | |
|---|---|---|
| 2011/0039771 A1 | 2/2011 | Cohen et al. |
| 2014/0296139 A1 | 10/2014 | Cohen et al. |
| 2017/0049853 A1 | 2/2017 | Cohen et al. |

FOREIGN PATENT DOCUMENTS

| | | |
|---|---|---|
| WO | WO 2001/070984 | 9/2001 |
| WO | WO 2001/076532 | 10/2001 |
| WO | WO 2003/037911 | 5/2003 |
| WO | WO 2004/094475 | 11/2004 |
| WO | WO 2014/144521 | 9/2014 |

OTHER PUBLICATIONS

NCBI, GenBank accession No. AY275535.1 (2012).
Amikura et al., "Presence of mitochondria-type ribosomes outside mitochondria in germ plasm of Drosophila embryos." *PNAS*, vol. 98, No. 16, pp. 9133-9138 (2001).
Bachar et al., "Humanin is expressed in human vascular walls and has a cytoprotective effect against oxidized LDL-induced oxidative stress." *Cardiovascular Research*, vol. 88, pp. 360-366 (2010).
Cheadle et al., "Analysis of Microarray Data Using Z Score Transformation." Journal of Molecular Diagnostics, vol. 5, No. 2, pp. 73-81 (2003).
Durieux et al., "The Cell-Non-Autonomous Nature of Electron Transport Chain-Mediated Longevity." *Cell*, vol. 144, pp. 79-91 (2011).
Galindo et al., "Peptides Encoded by Short ORFs Control Development and Define a New Eukaryotic Gene Family." *PLoS Biology*, vol. 5, No. 5, pp. 1052-1062 (2007).
Guo et al., "Humanin peptide suppresses apoptosis by interfering with Bax activation." *Nature*, vol. 423, pp. 456-461 (2003).
Hashimoto et al., "A rescue factor abolishing neuronal cell death by a wide spectrum of familial Alzheimer's disease genes and Aβ." *PNAS*, vol. 98, No. 11, pp. 6336-6341 (2001).
Hoang et al., "The neurosurvival factor Humanin inhibits beta cell apoptosis via Stat3 activation and delays and ameliorates diabetes in NOD mice." *Metabolism*, vol. 59, No. 3, pp. 343-349 (2010).
Ikonen et al., "Interaction between the Alzheimer's survival peptide humanin and insulin-like growth factor-binding protein 3 regulates cell survival and apoptosis." *PNAS*, vol. 100, No. 22, pp. 13042-13047 (2003).
Kim and Volsky, "Page: Parametric Analysis of Gene Set Enrichment." BMC *Bioinformatics*, vol. 6, No. 144 (2005).
Kondo et al., "Small Peptides Switch the Transcriptional Activity of Shavenbaby During *Drosophila embryogenesis.*" *Science*, vol. 329, pp. 336-339 (2010).
Lee et al., "Humanin: a harbinger of mitochondrial-derived peptides?" *Trends in Endocrinology and Metabolism*, vol. 24, No. 5, pp. 222-228 (2013).
Magny et al., "Conserved Regulation of Cardiac Calcium Uptake by Peptides Encoded in Small Open Reading Frames." *Science*, vol. 341, pp. 1116-1120 (2013).
Mercer et al., "The Human Mitochondrial Transcriptome." *Cell*, vol. 146, pp. 645-658 (2011).
Ninomiya and Ichinose, "Subcellular Distribution of Mitochondrial Ribosomal RNA in the Mouse Oocyte and Zygote." *PLoS ONE*, No. 11, pp. 1-9 (2007).
Nishimoto, et al., "Unravelling the role of Humanin." *TRENDS in Molecular Medicine*, vol. 10, No. 3 (2004).
Ricchetti et al., "Continued Colonization of the Human Genome by Mitochondrial DNA." *PLoS Biology*, vol. 2, No. 9, pp. 1313-1324 (2004).

(Continued)

*Primary Examiner* — Rachael E Bredefeld
*Assistant Examiner* — Erinne R Dabkowski
(74) *Attorney, Agent, or Firm* — Morgan, Lewis & Bockius LLP; Jeffry S. Mann; Louis T. Nguyen

(57) ABSTRACT

MOTS3 is a novel polypeptide. Methods of treating diseases such as diabetes, obesity, fatty liver, and cancer using MOTS3 and pharmaceutical compositions thereof are disclosed herein.

9 Claims, 75 Drawing Sheets

Specification includes a Sequence Listing.

(56) References Cited

OTHER PUBLICATIONS

Savard et al., "A Segmentation Gene in Tribolium Produces a Polycistronic mRNA that Codes for Multiple Conserved Peptides." *Cell*, vol. 126, pp. 559-569 (2006).
Tajima et al., "Evidence for in vivo production of Humanin peptide, a neuroprotective factor against Alzheimer's disease-related insults." *Neuroscience Letters*, vol. 324, pp. 227-231 (2002).
Villegas et al., "Localization of the 16S mitochondrial rRNA in the nucleus of mammalian spermatogenic cells." *Molecular Human Reproduction*, vol. 8, No. 11, pp. 977-983 (2002).
Ward and Thompson, "Metabolic Reprogramming: A Cancer Hallmark Even Warburg Did Not Anticipate." *Cancer Cell*, vol. 21, pp. 297-308 (2012).
Woo and Shadel, "Mitochondrial Stress Signals Revise an Old Aging Theory." *Cell*, vol. 144, pp. 11-12 (2011).
Zhang et al., "AMPK: An Emerging Drug Target for Diabetes and the Metabolic Syndrome." *Cell Metabolism*, vol. 9, pp. 407-416 (2009).

Figure 13C

```
(SEQ ID NO: 1)  Mt      MRWQEMGYIFYPRKLR----------------------------------------------
(SEQ ID NO: 8)  Ch.17a  MRWQEMGYIFYPRKFYD---------------------------------------NPYET-
(SEQ ID NO: 9)  Ch.17b  MRWQEMGYIFYPRKFYN---------------------------------------NPYET-
(SEQ ID NO: 10) Ch.11   MRWQEMGYIFYPRKLR----------------------------------------------
(SEQ ID NO: 11) Ch.1    MRWQEMGYIFYTQKILL---------------------------------------QPL---
(SEQ ID NO: 12) Ch.4    MRWQEMGYIFYTIRQISQ--------------------------------------QPL---
(SEQ ID NO: 13) Ch.17c  MRWQEMGYIFYTQKISR---------------------------------------QSL---
(SEQ ID NO: 14) Ch.X    MRWQEMGYIFYVQKLSR---------------------------------------QPL---
(SEQ ID NO: 15) Ch.17d  MRWQEMGYIFYTQKISRVRNTVDSRVPPKPSFGSRLTNQLIPVLBTCVAGSGRSL-
                        ***********
```

| From a total of 356 named biochemicals | Total number of biochemicals with P≤0.05 | Biochemicals (↑↓) P≤0.05 | Total number of biochemicals with 0.05<P<0.10 | Biochemicals (↑↓) 0.05<P<0.10 |
|---|---|---|---|---|
| MOTS-c 24h/Control 24h | 49 | 31 \| 18 | 28 | 18 \| 10 |
| MOTS-c 72h/Control 72h | 177 | 56 \| 121 | 26 | 10 \| 16 |
| MOTS-c ST/EV ST | 194 | 67 \| 127 | 22 | 6 \| 16 |

Figure 32

*Euglycemic-hyperinsulinemic Clamp Studies*

Metabolic parameters and circulating factors

| High Fat Diet (HFD) | Control | MOTS-c | P |
|---|---|---|---|
| n clamp | 6 | 8 | |
| Age (wks) | 47 | 47 (MOTS-c 2-wk Tx) | |
| Body weight (g) Pre-HFD | 35.7 ± 1.3 | 38.7 ± 1.0 | 0.09 |
| Body weight (g) 2-wks HFD | 36.8 ± 1.5 | 38.9 ± 1.3 | 0.28 (weight matched) |
| Gonadal Fat (g) | 1.41 ± 0.2 | 1.68 ± 0.126 | 0.025 |
| Liver weight (g) | 1.22 ± 0.06 | 1.39 ± 0.05 | 0.034 |
| Liver weight / BW (%) | 0.033 ± 0.002 | 0.036 ± 0.001 | 0.195 |
| Heart weight (g) | 0.141 ± 0.005 | 0.142 ± 0.006 | 0.83 |
| Fasting blood glucose (mg/dl) | 120 ± 4.6 | 128 ± 5 | 0.57 |
| Clamp blood glucose (mg/dl) | 120 ± 4.6 | 132 ± 3.6 | 0.72 |
| Clamp insulin (ng/ml) | 19.7 ± 3.4 | 13.4 ± 1.6 | 0.09 |
| GIR (mg/kg/min) | 38 ± 2 | 49 ± 3.7 | 0.016 |

SEQUENCE LISTING

```
<160> NUMBER OF SEQ ID NOS: 16

<210> SEQ ID NO 1
<211> LENGTH: 16
<212> TYPE: PRT
<213> ORGANISM: Homo sapiens

<400> SEQUENCE: 1

Met Arg Trp Gln Glu Met Gly Tyr Ile Phe Tyr Pro Arg Lys Leu Arg
1               5                   10                  15

<210> SEQ ID NO 2
<211> LENGTH: 51
<212> TYPE: DNA
<213> ORGANISM: Homo sapiens

<400> SEQUENCE: 2
```

-continued atgaggtggc aagaaatggg ctacattttc taccccagaa aactacgata g    51

<210> SEQ ID NO 3
<211> LENGTH: 14
<212> TYPE: PRT
<213> ORGANISM: Canis lupus

<400> SEQUENCE: 3

Met Arg Trp Met Gly Tyr Tyr Arg Thr His Cys Tyr Lys Asn
1               5                   10

<210> SEQ ID NO 4
<211> LENGTH: 13
<212> TYPE: PRT
<213> ORGANISM: Danio rerio

<400> SEQUENCE: 4

Met Lys Trp Met Gly Tyr Thr Tyr Arg Tyr Asn Val Thr
1               5                   10

<210> SEQ ID NO 5
<211> LENGTH: 6
<212> TYPE: PRT
<213> ORGANISM: Mus musculus

<400> SEQUENCE: 5

Met Lys Trp Met Gly Tyr
1               5

<210> SEQ ID NO 6
<211> LENGTH: 18
<212> TYPE: PRT
<213> ORGANISM: Rattus norvegicus

<400> SEQUENCE: 6

Met Lys Arg Lys Met Gly Tyr Ser Arg Thr Arg Asn Tyr Thr Lys Gly
1               5                   10                  15

Arg Arg

<210> SEQ ID NO 7
<211> LENGTH: 12
<212> TYPE: PRT
<213> ORGANISM: Panthera leo

<400> SEQUENCE: 7

Met Arg Trp Glu Ala Met Gly Tyr Ile Phe Tyr Asn
1               5                   10

<210> SEQ ID NO 8
<211> LENGTH: 17
<212> TYPE: PRT
<213> ORGANISM: Artificial Sequence
<220> FEATURE:
<223> OTHER INFORMATION: MOTS-c Ch. 17a

<400> SEQUENCE: 8

Met Arg Trp Gln Glu Met Gly Tyr Ile Phe Tyr Pro Arg Lys Phe Tyr
1               5                   10                  15

Asp

<210> SEQ ID NO 9
<211> LENGTH: 17
<212> TYPE: PRT
<213> ORGANISM: Artificial Sequence
<220> FEATURE:
<223> OTHER INFORMATION: MOTS-c Ch. 17b

<400> SEQUENCE: 9

Met Arg Trp Gln Glu Met Gly Tyr Ile Phe Tyr Pro Arg Lys Phe Tyr
1               5                   10                  15
Asn

<210> SEQ ID NO 10
<211> LENGTH: 16
<212> TYPE: PRT
<213> ORGANISM: Artificial Sequence
<220> FEATURE:
<223> OTHER INFORMATION: MOTS-c Ch. 11

<400> SEQUENCE: 10

Met Arg Trp Gln Glu Met Gly Tyr Ile Phe Tyr Phe Arg Lys Leu Arg
1               5                   10                  15

<210> SEQ ID NO 11
<211> LENGTH: 17
<212> TYPE: PRT
<213> ORGANISM: Artificial Sequence
<220> FEATURE:
<223> OTHER INFORMATION: MOTS-c Ch. 1

<400> SEQUENCE: 11

Met Arg Trp Gln Glu Met Gly Tyr Ile Phe Tyr Thr Gln Lys Ile Leu
1               5                   10                  15
Leu

<210> SEQ ID NO 12
<211> LENGTH: 17
<212> TYPE: PRT
<213> ORGANISM: Artificial Sequence
<220> FEATURE:
<223> OTHER INFORMATION: MOTS-c Ch. 4

<400> SEQUENCE: 12

Met Arg Trp Gln Glu Met Gly Tyr Ile Phe Tyr Ile Arg Gln Ile Ser
1               5                   10                  15
Gln

<210> SEQ ID NO 13
<211> LENGTH: 17
<212> TYPE: PRT
<213> ORGANISM: Artificial Sequence
<220> FEATURE:
<223> OTHER INFORMATION: MOTS-c Ch. 17c

<400> SEQUENCE: 13

Met Arg Trp Gln Glu Met Gly Tyr Ile Phe Tyr Thr Gln Lys Ile Ser
1               5                   10                  15
Arg

<210> SEQ ID NO 14
<211> LENGTH: 17
<212> TYPE: PRT
<213> ORGANISM: Artificial Sequence
<220> FEATURE:
<223> OTHER INFORMATION: MOTS-c Ch. X

<400> SEQUENCE: 14

Met Arg Trp Gln Glu Met Gly Tyr Ile Phe Tyr Val Gln Lys Leu Ser

-continued

```
1               5              10              15

Arg

<210> SEQ ID NO 15
<211> LENGTH: 55
<212> TYPE: PRT
<213> ORGANISM: Artificial Sequence
<220> FEATURE:
<223> OTHER INFORMATION: MOTS-c Ch. 17d

<400> SEQUENCE: 15

Met Arg Trp Gln Glu Met Gly Tyr Ile Phe Tyr Thr Gln Lys Ile Ser
1               5                   10                  15

Arg Val Arg Asn Thr Val Asp Ser Arg Val Pro Pro Lys Pro Ser Phe
            20                  25                  30

Gly Ser Arg Leu Thr Asn Gln Leu Ile Pro Val Leu Arg Thr Cys Val
        35                  40                  45

Ala Gly Ser Gly Arg Ser Leu
    50                  55

<210> SEQ ID NO 16
<211> LENGTH: 16
<212> TYPE: PRT
<213> ORGANISM: Homo sapiens

<400> SEQUENCE: 16

Met Gly Trp Gln Glu Met Gly Tyr Ile Phe Tyr Pro Arg Lys Leu Arg
1               5                   10                  15
```

MITOCHONDRIAL-DERIVED PEPTIDE MOTS3 REGULATES METABOLISM AND CELL SURVIVAL

CROSS REFERENCE TO RELATED APPLICATIONS

This application is a Divisional of U.S. application Ser. No. 15/146,249 filed May 4, 2016, now U.S. Pat. No. 10,064,914 which is a Divisional of U.S. application Ser. No. 14/213,617 filed Mar. 14, 2014 which claims, under 35 U.S.C. § 119(e), the benefit of U.S. Provisional Application No. 61/801,474, filed Mar. 15, 2013, the disclosures of which are incorporated herein by reference in their entireties for all purposes.

GOVERNMENT RIGHTS

This invention was made with Government support under Grant Nos. AG034430 and GM090311, awarded by the National Institutes of Health. The Government has certain rights in the invention.

FIELD OF THE INVENTION

This invention relates to a novel mitochondrial-derived peptide (MOTS3). This novel peptide can be used in methods of treating diseases such as diabetes, obesity, fatty liver, and cancer.

BACKGROUND

Mitochondria, central to metabolic processes, is involved energy production, programmed cell death, and reactive oxygen species (ROS) generation, and is heavily implicated in various stages of major diseases including cancer, diabetes, neurodegenerative diseases, and aging; yet its role in the pathogenesis still remains largely unclear. Traditionally, mitochondria have been considered as "end-function" organelles, receiving and processing vast amounts of cellular signals to regulate energy production and cell death. However, retrograde signaling, whereby the mitochondria communicate back to the cell, is a poorly understood biological process.

Calcium, cytochrome C, and ROS have been considered a retrograde mitochondrial molecule. Notably, Durieux et al. proposed that signals originating from mitochondria can regulate the lifespan of *C. elegans* in a cell non-autonomous manner, but the nature of such signals has not been identified in worms (Durieux et al., *Cell* 144, 79 (Jan. 7, 2011). The identity of such mitochondria-derived signals may have been discovered in 2001, when a 24 amino acid peptide, now known as humanin (HN), was cloned from a cDNA library constructed from the surviving fraction of an Alzheimer patient's brain and was mapped to the mitochondrial 16S rRNA locus (Hashimoto et al., *Proc Natl Acad Sci USA* 98, 6336 (May 22, 2001). Since then, HN has been shown to be a cytoprotective and anti-apoptotic factor, partially due to its role as a Bax antagonist that prevents apoptosis in various cancer cells (Guo et al., *Nature* 423, 456 (May 22, 2003) as an IGFBP-3 partner that antagonizes the apoptotic actions of IGFBP-3 on cancer cells (Ikonen et al., *Proc Natl Acad Sci USA* 100, 13042 (Oct. 28, 2003). More recent work indicates that HN is a wide spectrum survival factor (Nishimoto et al., *Trends Mol Med* 10, 102 (March, 2004)), however, its exact mechanism of action remains unclear.

Mitochondria-derived humanin shares 92-95% identity with several nuclear-encoded cDNAs, which represent domains within larger hypothetical genes, whose expression has not been validated (Tajima et al., *Neurosci Lett* 324, 227 (May 24, 2002)). HN transcripts of mitochondrial origin are present in kidney, testis, brain, and the gastrointestinal tract. Of note is that humanin is highly conserved among species (between 90-100% homology), including lower organisms. The peptide has been demonstrated in brain and testis and we have shown that it is present in 1-10 ng/ml concentrations in plasma, CSF and seminal fluid. Novel mutants and analogs of HN with more potent actions have been described, including HNG (S14G), HNG-F6A (non-IGFBP-3 binding, which we have recently protected as a possible type-2 diabetes treatment under a joint AECOM/UCLA patent that has been submitted) and colivelin (hybrid peptide containing partial sequences of HN and ADNF9). Humanin and its analogues and derivatives are showing therapeutic potential for an array of diseases including Alzheimer's disease, diabetes and kidney failure.

This report is the first description of a novel open-reading frame (ORF) in the 12S rRNA. The name of this novel ORF in the 12S rRNA is Mitochondrial ORF in the Twelve S rRNA 3 (MOTS3). Similar to HN (Y. Hashimoto et al., *Proc Natl Acad Sci USA* 98, 6336 (May 22, 2001)), the MOTS3 transcripts are polyadenylated and suggest a gene within-a-gene structure that is well conserved throughout species.

MOTS3 is detected in the liver, heart, testis at the same molecular weight, but found with a slightly higher molecular weight in the brain of mice and rats. Its main biological function is metabolic regulation with strong influence on mitochondrial respiration and glucose utilization in both cell culture and mice. MOTS3 has also been tested in various ways in vitro and in vivo to affect mitochondrial respiration, glucose utilization, insulin regulation and cellular proliferation/survival.

Furthermore, MOTS3 is a non-toxic natural peptide derived from the mitochondria that has a general metabolic regulatory role. It is the first of its kind that provides strong body weight and blood glucose regulation as well as activation of AMPK which is a major drug target for diabetes and cancer via the mTOR pathway. It is from an entirely novel category of drugs, i.e. mtDNA-derived signaling peptides that have only recently been described. Accordingly, MOTS3 and pharmaceutical formulations thereof can be used to treat various age-related disease with much metabolic implications such as cancer, diabetes, obesity, and neurodegenerative diseases are not sufficient to cure the disease.

Accordingly, this invention discloses the novel MOTS3 ORFs and methods of use thereof to treat disease.

BRIEF SUMMARY OF THE INVENTION

In certain embodiments, this invention comprises an isolated polypeptide comprising 70% sequence identity to SEQ ID NO:1. In certain embodiments, the isolated polypeptide comprises an 80% sequence identity to SEQ ID NO:1. In certain embodiments, the isolated polypeptide comprises an 90% sequence identity to SEQ ID NO:1. In certain embodiments, the isolated polypeptide comprises the sequence of SEQ ID NO:1.

In certain embodiments, this invention comprises an isolated antibody that specifically binds to a polypeptide described above. In certain embodiments, the antibody is a monoclonal antibody.

In certain embodiments, this invention comprises an isolated polypeptide comprising 70% sequence identity to SEQ ID NO:1. In certain embodiments, the polypeptide comprises 80% or 90% sequence identity to SEQ ID NO:1. In certain embodiments, the polypeptide comprises the sequence of SEQ ID NO:1.

In certain embodiments, this invention comprises a method of treating diabetes, the method comprising the step of administering to a subject in need thereof a therapeutically effective amount of a pharmaceutical composition comprising an isolated polypeptide comprising 70% sequence identity to SEQ ID NO:1. In certain embodiments, the polypeptide comprises 80% or 90% sequence identity to SEQ ID NO:1. In certain embodiments, the polypeptide comprises the sequence of SEQ ID NO:1. In certain embodiments, the diabetes is type I diabetes. In certain embodiments, the diabetes is type II diabetes. In certain embodiments, the subject is a human.

In certain embodiments, this invention comprises a method of treating obesity and/or fatty liver, the method comprising the step of administering to a subject in need thereof a therapeutically effective amount of a pharmaceutical composition comprising an isolated polypeptide comprising 70% sequence identity to SEQ ID NO:1. In certain embodiments, the polypeptide comprises 80% or 90% sequence identity to SEQ ID NO:1. In certain embodiments, the polypeptide comprises the sequence of SEQ ID NO:1. In certain embodiments, the subject is a mammal. In certain embodiments, the subject is a human.

In certain embodiments, this invention comprises a method of treating cancer, the method comprising the step of administering to a subject in need thereof a therapeutically effective amount of a pharmaceutical composition comprising an isolated polypeptide comprising 70% sequence identity to SEQ ID NO:1. In certain embodiments, the polypeptide comprises 80% or 90% sequence identity to SEQ ID NO:1. In certain embodiments, the polypeptide comprises the sequence of SEQ ID NO:1. In certain embodiments, the subject is a human. In certain embodiments, the cancer is a cancer selected from a group consisting of breast cancer, brain cancer, colon cancer, melanoma, leukemia (e.g., AML), lymphoma, pancreatic cancer, prostate cancer, ovarian cancer, lung cancer, and gastric cancer.

In some embodiments, this invention comprises a cDNA molecule that encodes SEQ ID NO:1. In some embodiments, this invention comprises a cDNA at least 80%, 90% or 100% identical to SEQ ID NO:2.

In some embodiments, this invention comprises an expression vector comprising a nucleic acid sequence that encodes SEQ ID NO:1. In some embodiments, this invention comprises an expression vector comprising a cDNA at least 80%, 90% or 100% identical to SEQ ID NO:2.

In some embodiments, this invention provides a host cell transformed or transfected with an expression vector as described herein in the present disclosure.

BRIEF DESCRIPTION OF THE DRAWINGS

FIG. 13A-FIG. 13J describes MOTS-c is a novel peptide encoded in the mitochondrial genome. a, MOTS-c is encoded within the 12S rRNA of the mitochondrial genome as a 51 bp open reading frame (ORF). Use of the mitochondrial genetic code yields tandem start/stop codons, whereas the cytoplasmic genetic code yields a viable peptide. b, 3' rapid amplification of cDNA ends (3' RACE) shows that MOTS-c and humanin transcripts are polyadenylated. c, Comparison of MOTS-c encoded in mitochondrial DNA (mtDNA) and peptides encoded in nuclear DNA that have been transferred from mtDNA (NUMT) through evolution. d-e, HeLa ρ0 cells, which are devoid of mitochondrial DNA through prolonged exposure to low doses ethidium bromide (EtBr), have undetectable levels of: d, 12S rRNA and MOTS-c transcripts by qRT-PCR, and e, mitochondria-encoded proteins cytochrome C oxidase I and II (COI/II), as well as MOTS-c, but normally express the nuclear-encoded GAPDH detected by immunoblotting. f, MOTS-c (green) and hsp60 (red) immunostaining in HEK293 cells. Scale bar, 20 μm. g-h, MOTS-c is detected in: g, various tissues in mice and rats and h, circulation (plasma) in humans and rodents. i-j, Fasting, a metabolic stress, alters expression of endogenous MOTS-c in i, tissues, and j, plasma in mice. Data shown as mean±SEM. Student's t-test. *P<0.05, P<0.01, *P<0.001

FIG. 30 describes microarray data on HEK293 cells treated with MOTS-c (10 µM) for 72-hours (N=6). See FIG. 14d.

FIG. 31 describes the total number of biochemicals (metabolites) in HEK293 cells with significant (P≤0.05) and borderline significant (0.05<P<0.1) changes 24- and 72-hours after exogenous MOTS-c treatment (10 µM) or stably over-expressing MOTS-c or empty vector (EV) (N=5). Red: increased, Blue: decreased. Welch's Two Sample t-tests.

FIG. 32 describes the metabolic parameters and circulating factors from the euglycemic-hyperinsulinemic clamp study in FIG. 16 h-j. Student's t-test.

DEFINITIONS

Figures 1A, 1B, 1C, 1D, 1E:
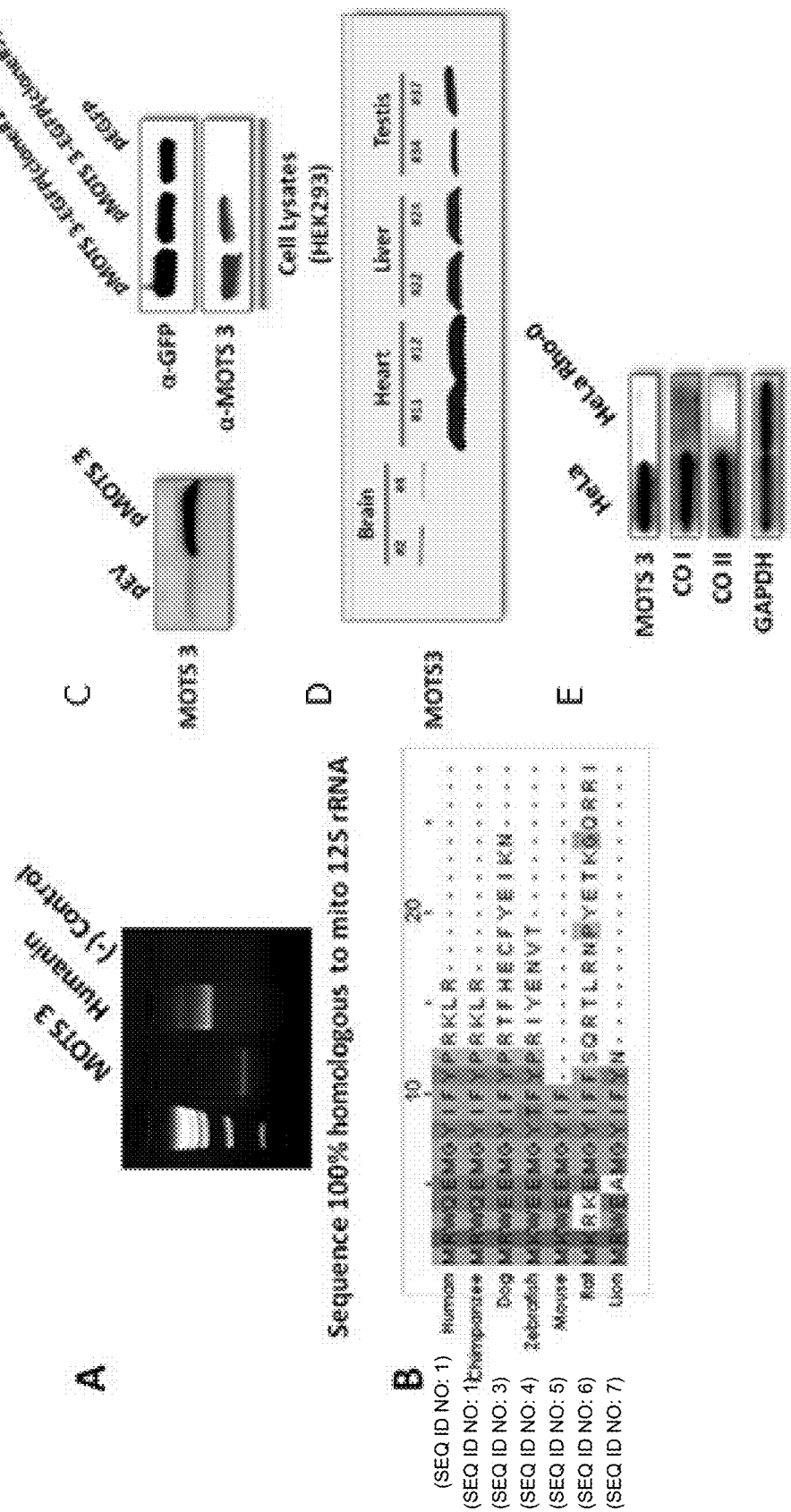
FIG. 1A-FIG. 1E shows that MOTS3 is a polyadenylated transcript from the mitochondrial 12S rRNA (A). MOTS 3 sequence is well conserved in various organisms (B). Rabbit polyclonal anti-MOTS3 antibody recognizes overexpressed MOTS3 as well as GFP tagged MOTS3 cloned into an expression vector in cells (C). MOTS3 is found in rat heart, liver, and testis at similar molecular weights but at a slightly higher molecular weight in the brain (D). MOTS3 is not detected in Rho-0 cells which do not have mitochondrial DNA (E). CO I/II (cytochrome oxidase I/II) were used to verify lack of mitochondrial DNA.

For convenience, the meaning of certain terms and phrases used in the specification, examples, and appended claims, are provided below.

As used herein, the term "diabetes" refers to the broad class of disorders characterized by impaired insulin production and glucose tolerance. Diabetes includes type 1 and type 2 diabetes (also called juvenile and adult-onset, respectively), gestational diabetes, prediabetes, insulin resistance, metabolic syndrome, and impaired glucose tolerance. Common symptoms include frequent urination, excessive thirst, extreme hunger, unusual weight loss, increased fatigue, irritability, and blurry vision. Diagnosis of these individual disorders is described in more detail below.

Type I diabetes is also known as Insulin Dependent Diabetes Mellitus (IDDM), Type 1 diabetes, and juvenile diabetes. The terms are used interchangeably herein. Treatment and diagnosis of the disease is described in more detail below "Pancreatic beta cells," "beta islet cells," and similar terms refer a population of pancreatic endocrine cells found in the Islets of Langerhans. Beta islet cells produce and secrete insulin and amylin into the bloodstream.

As used herein, "improving cell survival" refers to an increase in the number of cells that survive a given condition, as compared to a control, e.g., the number of cells that would survive the same conditions in the absence of treatment. Conditions can be in vitro, in vivo, ex vivo, or in situ. Improved cell survival can be expressed as a comparative value, e.g., twice as many cells survive if cell survival is improved two-fold. Improved cell survival can result from a reduction in apoptosis, an increase in the life-span of the cell, or an improvement of cellular function and condition. In some embodiments, cell survival is improved by 5, 10, 20, 30, 40, 50, 60, 70, 80, 90 or 100%, as compared to control levels. In some embodiments, cell survival is by two-, three-, four-, five-, or ten-fold of control levels. Alternatively, improved cell survival can be expressed as a percentage decrease in apoptosis. In some embodiments, for example, apoptosis is reduced by 10, 20, 30, 40, 50, 60, 70, 80, 90 or up to 100%, as compared to a control sample.

The term "preventing a disorder" as used herein, is not intended as an absolute term. Instead, prevention, e.g., of type 1 diabetes, refers to delay of onset, reduced frequency of symptoms, or reduced severity of symptoms associated with the disorder. Prevention therefore refers to a broad range of prophylactic measures that will be understood by those in the art. In some circumstances, the frequency and severity of symptoms is reduced to non-pathological levels, e.g., so that the individual does not need traditional insulin replacement therapy. In some circumstances, the symptoms of an individual receiving the compositions of the invention are only 90, 80, 70, 60, 50, 40, 30, 20, 10, 5 or 1% as frequent or severe as symptoms experienced by an untreated individual with the disorder.

Similarly, the term "treating a disorder" is not intended to be an absolute term. In some aspects, the compositions of the invention seek to reduce the loss of insulin producing cells that lead to diabetic symptoms. In some circumstances, treatment with the leads to an improved prognosis or a reduction in the frequency or severity of symptoms.

As used herein, the term "an individual in need of treatment or prevention" refers to an individual that has been diagnosed with type 1 diabetes, type 2 diabetes, gestational diabetes, pre-diabetes, insulin resistance, metabolic syndrome, or impaired glucose tolerance, or one that is at risk of developing any of these disorders. Individuals in need of treatment also include those that have suffered an injury, disease, or surgical procedure affecting the pancreas, or individuals otherwise impaired in their ability to make insulin. Such individuals can be any mammal, e.g., human, dog, cat, horse, pig, sheep, bovine, mouse, rat, rabbit, or primate.

As used herein, the term "percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

As used herein, the terms "identical" or percent "identity," in the context of two or more nucleic acids or polypeptide sequences, refer to two or more sequences or subsequences that are the same sequences. Sequences are "substantially identical" if two sequences have a specified percentage of amino acid residues or nucleotides that are the same (i.e., 60% identity, optionally 65%, 70%, 75%, 80%, 85%, 90%, or 95% identity over a specified region, or, when not specified, over the entire sequence), when compared and aligned for maximum correspondence over a comparison window, designated region as measured using one of the following sequence comparison algorithms or by manual alignment and visual inspection, or across the entire sequence where not indicated. The invention provides polypeptides or polynucleotides encoding polypeptides that are substantially identical, or comprising sequences substantially identical, to the polypeptides exemplified herein (e.g., humanin). This definition also refers to the complement of a nucleotide test sequence.

A "pre-diabetic individual" refers to an adult with a fasting blood glucose level greater than 110 mg/dl but less than 126 mg/dl or a 2 hour PG reading of greater than 140 mg/dl but less than 200 mg/dl. A "diabetic individual" refers to an adult with a fasting blood glucose level greater than 126 mg/dl or a 2 hour PG reading of greater than 200 mg/dl.

DETAILED DESCRIPTION OF THE INVENTION

Introduction

A decade ago, the first mitochondria-derived peptide (MDP), humanin (HN), was cloned from a cDNA library constructed from the non-affected fraction of an Alzheimer patient's brain and was mapped to the mitochondrial 16s rRNA locus. HN has been shown to be a cytoprotective and anti-apoptotic factor (Bachar, A. R., et al., (2010). *Humanin is expressed in human vascular walls and has a cytoprotective effect against oxidized LDL-induced oxidative stress. Cardiovascular research* 88, 360-366; Guo, B., et al., (2003). *Humanin peptide suppresses apoptosis by interfering with Bax activation. Nature* 423, 456-461; Hashimoto, Y., et al., (2001). *A rescue factor abolishing neuronal cell death by a wide spectrum of familial Alzheimer's disease genes and Abeta. Proc Natl Acad Sci USA* 98, 6336-6341; Hoang, P. T., et al., (2010). *The neurosurvival factor Humanin inhibits beta-cell apoptosis via signal transducer and activator of transcription 3 activation and delays and ameliorates diabetes in nonobese diabetic mice. Metabolism: clinical and experimental* 59, 343-349; and Ikonen, M., et al. (2003). *Interaction between the Alzheimer's survival peptide humanin and insulin-like growth factor-binding protein 3 regulates cell survival and apoptosis. Proc Natl Acad Sci USA* 100, 13042-13047). There are now over 130 publications describing various aspects of HN biology.

Building previous observations, an additional MDP encoded within the 12S rRNA and have named it MOTS3 (Mitochondrial Open-reading-frame within the Twelve S rRNA) was discovered in silico and is disclosed herein (Table 1).

TABLE 1

Sequence and location of MOTS3
(SEQ ID NO: 1 and SEQ ID NO: 2).

| Name | Translation | Location | Region | Sequence | #AA |
|---|---|---|---|---|---|
| MOTS3 | Cytoplasmic | 1343-1393 | 696-746 | MRWQEMGYIFYPRK LR (SEQ ID NO: 1) ATGAGGTGGCAAGA AATGGGCTACATTT TCTACCCCAGAAAA CTACGATAG (SEQ ID NO: 2) | 16 |

As reported herein, MOTS3 shifts the cellular metabolic state by modulating mitochondrial function/metabolism and glucose utilization. This has much potential to be applied to various diseases in which mitochondria play a major role in either pathogenesis or maintenance/progression of the disease, such as cancer, diabetes, fatty liver, neurodegenerative diseases, hypertension, and aging.

Furthermore, mitochondrial dysfunction plays a central role in the pathogenesis of neurodegenerative disorders, including Alzheimer's disease (AD) as well as hypertension.

In cancer, mitochondria are central organelles for biosynthetic precursor production to supply its signature rampant proliferation, which can be counteracted by MOTS3-dependent mitochondrial function suppression and reduced cellular proliferation (Ward and Thompson, (2012) *Metabolic reprogramming: a cancer hallmark even warburg did not anticipate. Cancer cell* 21, 297-308).

Figures 11A, 11B, 11C:
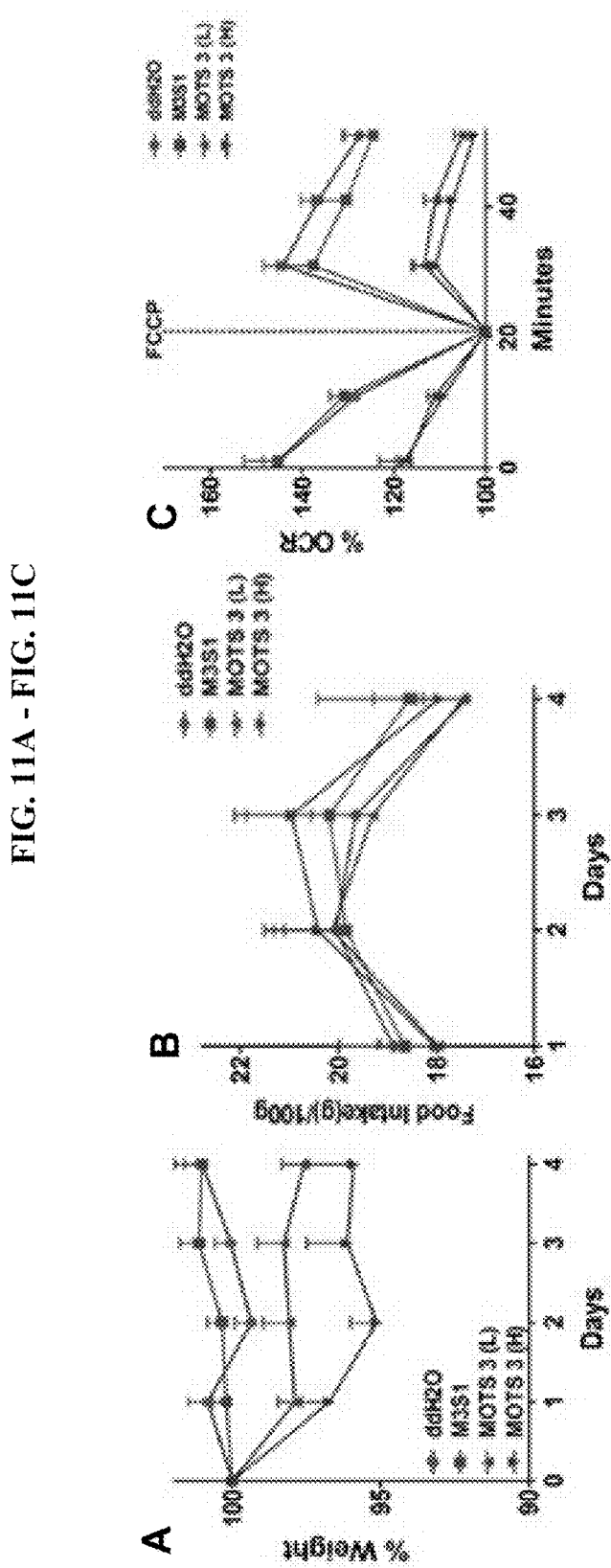
FIG. 11A-FIG. 11C shows that MOTS3 reduces body weight and liver mitochondrial respiration capacity. 4 days of MOTS 3 injections (i.p.; 0.5 and 5.0 mg/kg/day) in mice significantly reduced body weight but did not alter food intake. Liver mitochondrial respiration capacity was also reduced at both doses of MOTS3.
Figures 12A, 12B:
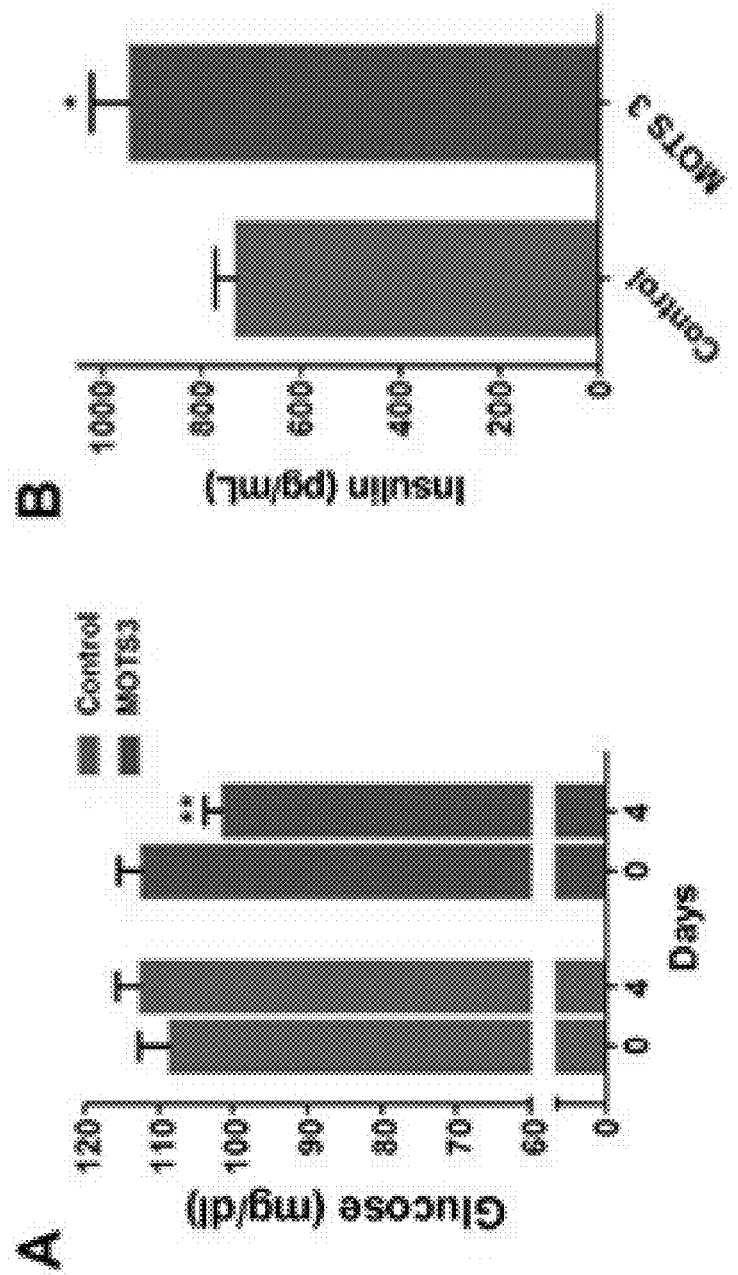
FIG. 12A-FIG. 12B illustrates mice treated with MOTS3 for 4 days show reduced blood glucose levels (A) and elevated insulin levels (B).

Metabolic diseases such as obesity and fatty liver could also be treated with MOTS3 as it is effective in regulating body weight and hepatic mitochondrial respiration under the same amount of food consumption (FIG. 11). In diabetes, drugs that activate Adenosine 5'-monophosphate (AMP)-activated protein kinase (AMPK), such as metformin and AICAR, have been well documented to regulate glucose homeostatsis and currently used in clinics (Zhang et al., (2009) *AMPK: an emerging drug target for diabetes and the metabolic syndrome. Cell metabolism* 9, 407-416). Accordingly, MOTS3 is also a strong activator of AMPK (FIG. 6) as well as a significant regulator of glucose levels (FIG. 12A) and thus could be used to treat diabetes.

Diabetes

Type II diabetes (non-insulin dependent diabetes) is a common metabolic disorder that is rapidly increasing particularly in the developed world. It can be characterized by insulin resistance, insulin deficiency and hyperglycaemia. Factors that are linked with Type II diabetes include elevated cholesterol, obesity and hypertension.

Type II diabetes may not be diagnosed for many years since symptoms may be sporadic and are certainly milder than those associated with Type I diabetes. However, elevated blood sugar levels in untreated Type II diabetes sufferers can lead to functional impairment of kidneys, eyes and cardiovascular systems.

Furthermore, Type II diabetes may be caused by the failure of beta cells to compensate for insulin resistance. High-caloric diets and insufficient muscle work seem to be important environmental factors involved in the pathogenesis of obesity and Type II diabetes. Environmental factors seem to act via two major targets. One is the processing of glucose, fatty acids and other metabolites, as regulated by insulin and other hormones in the majority of tissues, and the other is beta cell function.

Obesity has become a major public health problem. Health conditions caused or exacerbated by obesity include hypertension, diabetes mellitus, sleep apnea, obesity-related hypoventilation, back and joint problems, cardiovascular disease, non-alcoholic fatty liver disease and gastroesophageal reflux disease.

The body mass index (BMI) (calculated as weight in kilograms divided by the square of height in meters) is the most commonly accepted measurement for overweight and/or obesity. A BMI exceeding 25 is considered overweight, while obesity is defined as a BMI of 30 or more, with a BMI of 35 or more considered as serious comorbidity and a BMI of 40 or more considered morbid obesity.

Type I diabetes is an autoimmune disease characterized by the progressive destruction of pancreatic beta cells following infiltration of the islet by lymphocytes. This results in insulin deficiency.

Apoptosis is the primary mode of beta cell death during development of Type-1 diabetes (O'Brien et al. (1997) *Diabetes* 46:750-57). IL-1, TNF-alpha and IFN-gamma are released by T cells and macrophages during this autoimmune response and are important mediators of beta cell destruction (Eizirik and Mandrup-Poulsen (2001) *Diabetologia* 44:2115-2133).

Insulin-like Growth Factor Binding Protein-3 (IGFBP-3) induces apoptosis in a manner unrelated to its IGF binding (Rajah et al. (1997) *J Biol Chem.* 272:12181-88). Pro-inflammatory Th1 cytokines increases intranuclear aggregation of endogenous IGFBP-3 and addition of exogenous IGFBP-3 to beta cells induces apoptosis (Shim et al. (2004) *Growth Norm IGF Res.* 14:216-25). IGFBP-3 is one of a number of peptides that includes insulin, leptin, adiponectin, and resistin, that have been shown to act in the central nervous system to regulate glucose metabolism (Muse et al. (2007) *J Clin Invest*. 117:1670-78; Obici et al. (2002) *Nat Med* 8:1376-82). Beta cell loss by apoptosis also occurs after islet graft (Paraskevas et al. (1999) *FEBS Lett*. 455:203-8); Tobiasch et al. (2001) *J Investig Med*. 49:566-71). Recent studies have demonstrated that isolated human islets express the pro-apoptotic protein Bax at higher level than the anti-apoptotic protein Bcl-2 (Thomas et al. (2002) *Transplantation* 74:1489).

Over a million people in the U.S. have Type I diabetes. According to the American Diabetes Association, the disease causes thousands of deaths every year and costs more than $20 billion annually. There is need effective therapeutic or preventative agent available for Type I diabetes.

There is a need to develop methods to treat and prevent Type I and Type II diabetes. Accordingly, in certain embodiments of this invention, MOTS3 and pharmaceutical compositions thereof can be used to treat and prevent Type I and Type II diabetes.

Cancer

Cancer is a serious threat to modern society. Worldwide, more than 10 million people are diagnosed with cancer every year and it is estimated that this number will grow to 15 million new cases every year by 2020. Cancer causes six million deaths every year or 12% of the deaths worldwide.

Malignant cancerous growths, due to their unique characteristics, pose serious challenges for modern medicine. Their characteristics include uncontrollable cell proliferation resulting in unregulated growth of malignant tissue, an ability to invade local and even remote tissues, lack of differentiation, lack of detectable symptoms and most significantly, the lack of effective therapy and prevention.

Cancer can develop in any tissue of any organ at any age. The etiology of cancer is not clearly defined but mechanisms such as genetic susceptibility, chromosome breakage disorders, viruses, environmental factors and immunologic disorders have all been linked to a malignant cell growth and transformation. Cancer encompasses a large category of medical conditions, affecting millions of individuals worldwide. Cancer cells can arise in almost any organ and/or tissue of the body. Cancer develops when cells in a part of the body begin to grow or differentiate out of control. All cancer types begin with the out-of-control growth of abnormal cells.

There are many types of cancer, including but not limited to, brain cancer, colon cancer, melanoma, leukemia (e.g., AML), lymphoma, pancreatic cancer, prostate cancer, ovarian cancer, lung cancer, and gastric cancer.

Currently, some of the main treatments available are surgery, radiation therapy, and chemotherapy. Surgery is often a drastic measure and can have serious consequences. For example, all treatments for ovarian cancer may result in infertility. Some treatments for cervical cancer and bladder cancer may cause infertility and/or sexual dysfunction. Surgical procedures to treat pancreatic cancer may result in partial or total removal of the pancreas and can carry significant risks to the patient. Breast cancer surgery invariably involves removal of part of or the entire breast. Some surgical procedures for prostate cancer carry the risk of urinary incontinence and impotence. The procedures for lung cancer patients often have significant post-operative pain as the ribs must be cut through to access and remove the cancerous lung tissue. In addition, patients who have both lung cancer and another lung disease, such as emphysema or chronic bronchitis, typically experience an increase in their shortness of breath following the surgery. Radiation therapy has the advantage of killing cancer cells but it also damages non-cancerous tissue at the same time. Chemotherapy involves the administration of various anti-cancer drugs to a patient but often is accompanied by adverse side effects.

Thus, there remains a need for methods that can treat and prevent cancer. These methods can provide the basis for pharmaceutical compositions useful in the prevention and treatment of cancer in humans and other mammals. Accordingly, in certain embodiments of this invention, MOTS3 and pharmaceutical compositions thereof can be used to treat and prevent cancer. Specifically, as non-limiting examples, MOTS3 and pharmaceutical compositions thereof can be used to treat and prevent brain cancer, colon cancer, melanoma, leukemia (e.g., AML), lymphoma, pancreatic cancer, prostate cancer, ovarian cancer, lung cancer, and gastric cancer.

Fatty Liver and Obesity

Fatty liver, also known as Fatty Liver Disease (FLD), is a reversible condition where vacuoles of triglyceride fats accumulate in the liver. The process of fat accumulation in the liver cells is known as steatosis.

Obesity is a general term for describing having too much body fat. Obesity occurs when a subject takes in more calories than he/she can burn, leading to stores of fat. Obesity is caused by taking in more calories than a subject needs and not getting enough exercise. Two of the most common methods for assessing obesity are the Body Mass Index (BMI) and waist circumference. BMI is calculated using height and weight. A high BMI, i.e., obesity, increases the risk of Type II diabetes, heart disease, and stroke.

Thus, there remains a need for methods that can treat and prevent fatty liver disease and obesity. Accordingly, in certain embodiments of this invention, MOTS3 and pharmaceutical compositions thereof can be used to treat and prevent fatty liver disease and obesity.

Expression and Purification of Polypeptides

Naturally-occurring, synthetic, or recombinant polypeptides of the invention can be purified for use in compositions and functional assays. Naturally-occurring polypeptides of the invention can be purified from any source. Recombinant polypeptides can be purified from any suitable expression system (e.g., mammalian, insect, yeast, or bacterial cell culture).

The peptides of the present invention (i.e., MOTS3 and MOTS3 analogues) may include both modified peptides and synthetic peptide analogues. In some embodiments the peptide is a peptide 70%, 75%, 80%, 85%, 90%, 95%, 97% or 100% identical to SEQ ID NO:1. In some embodiments the peptide is a peptide comprising SEQ ID NO:1. In some embodiments, the peptide is SEQ ID NO:1. Peptides as described herein may be modified to improve formulation and storage properties, or to protect labile peptide bonds by incorporating non-peptidic structures. Peptides of the present invention may be prepared using methods known in the art. For example, peptides may be produced by chemical synthesis, e.g., using solid phase techniques and/or automated peptide synthesizers. In certain instances, peptides may be synthesized using solid phase strategies on an automated multiple peptide synthesizer (Abimed AMS 422) using 9-fluorenylmethyloxycarbonyl (Fmoc) chemistry. The peptides can then be purified by reversed phase-HPLC and lyophilized.

For recombinant approaches, the present invention includes isolated nucleic acids encoding the polypeptides disclosed herein, expression vectors comprising the nucleic acids, and host cells comprising the expression vectors. More particularly, the invention provides isolated nucleic acids encoding MOTS3 peptides and MOTS3 peptide analogues having MOTS3 activities, the peptides including, but not limited to, SEQ ID NO:1. In some embodiments, this invention comprises a cDNA molecule that encodes a peptide at least 70%, 75%, 80%, 85%, 90%, 95%, 97% or 100% identical to SEQ ID NO:1. In some embodiments, this invention comprises a cDNA molecule that encodes SEQ ID NO:1. In some embodiments, this invention comprises a cDNA at least 70%, 75%, 80%, 85%, 90%, 95%, 97% or 100% identical to SEQ ID NO:2.

When recombinant proteins are expressed by the transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells typically, but not limited to, by incubation in a buffer of about 100-150 μg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook et al., both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques.

Alternatively, it is possible to purify proteins from bacteria periplasm. Where the protein is exported into the periplasm of the bacteria, the periplasmic fraction of the bacteria can be isolated by cold osmotic shock in addition to other methods known to those of skill in the art (see, Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

The polypeptides of the invention may be purified to substantial purity by standard techniques, including selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al., Current Protocols in Molecular Biology (1995 supplement); and Sambrook et al. MOLECULAR CLONING: A LABORATORY MANUAL, 2nd Ed., (1989)).

A number of procedures can be employed when polypeptides are being purified. For example, polypeptides can be purified using ion exchange or immunoaffinity columns.

Often as an initial step, and if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

The proteins of interest can also be separated from other proteins on the basis of their size, net surface charge, hydrophobicity and affinity for ligands. In addition, antibodies raised against proteins can be conjugated to column matrices and the proteins immunopurified. All of these methods are well known in the art.

Immunoaffinity chromatography using antibodies raised to a variety of affinity tags such as hemagglutinin (HA), FLAG, Xpress, Myc, hexahistidine, glutathione S transferase (GST) and the like can be used to purify polypeptides. The His tag will also act as a chelating agent for certain metals (e.g., Ni) and thus the metals can also be used to purify His-containing polypeptides. After purification, the tag is optionally removed by specific proteolytic cleavage.

It will be apparent to one of skill that chromatographic techniques can be performed at any scale and using equipment from many different manufacturers (e.g., Pharmacia Biotech).

Pharmaceutical Compositions

The peptides of the present invention can be administered with a suitable pharmaceutical excipient as necessary. One of skill will understand that the composition will vary depending on mode of administration and dosage unit.

The compositions typically include a conventional pharmaceutical carrier or excipient and may additionally include other medicinal agents, carriers, adjuvants, diluents, tissue permeation enhancers, solubilizers, and the like. Preferably, the composition will contain about 0.01% to about 90%, about 0.1% to about 75%, about 0.1% to 50%, or about 0.1% to 10% by weight of a conjugate of the present invention or a combination thereof, with the remainder consisting of suitable pharmaceutical carrier and/or excipients. Appropriate excipients can be tailored to the particular composition and route of administration by methods well known in the art. See, e.g., REMINGTON'S PHARMACEUTICAL SCIENCES, 18TH ED., Mack Publishing Co., Easton, Pa. (1990).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The compositions can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; coloring agents; and flavoring agents. The compositions may also comprise biodegradable polymer beads, dextran, and cyclodextrin inclusion complexes.

For oral administration, the compositions can be in the form of tablets, lozenges, capsules, emulsions, suspensions, solutions, syrups, sprays, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the pharmaceutical compositions take the form of a pill, tablet, or capsule, and thus, the composition can contain, along with the conjugate or combination of conjugates, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. The conjugates can also be formulated into a suppository disposed, for example, in a polyethylene glycol (PEG) carrier.

Liquid compositions can be prepared by dissolving or dispersing a conjugate or a combination of conjugates and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. The conjugates of the present invention can also be formulated into a retention enema.

For topical administration, the compositions of the present invention can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

One of ordinary skill in the art understands that the dose administered will vary depending on a number of factors, including, but not limited to, the particular peptide composition to be administered, the mode of administration, the type of application (e.g., prophylactic, therapeutic, etc.), the age of the patient, and the physical condition of the patient. Preferably, the smallest dose and concentration required to produce the desired result should be used. Dosage can be appropriately adjusted for children, the elderly, debilitated patients, and patients with cardiac and/or liver disease. Further guidance can be obtained from studies known in the art using experimental animal models for evaluating dosage. The MOTS3 or MOTS3 analog can be formulated without undue experimentation for administration to a mammal, including humans, as appropriate for the particular application. Additionally, proper dosages of the compositions can be determined without undue experimentation using standard dose-response protocols.

In some embodiments, the peptide comprising compositions of the present invention are administered to a subject at a particular dose of the peptide or are formulated for unit dosage administration of the peptide to a subject. In some embodiments, the dose administered to a subject is from about 0.001 to about 1000 mg per day. In some embodiments, the dose administered to a subject is from about 0.1 to about 500 mg per day. In some embodiments, the dose administered to a subject is from about 0.5 to about 100 mg per day. In some embodiments, the compositions of the present invention are formulated for unit dosage administration, wherein the unit dosage is from about 0.001 to about 1000 mg per day. In some embodiments, the compositions of the present invention are formulated for unit dosage administration, wherein the unit dosage is from about 0.1 to about 500 mg per day. In some embodiments, the compositions of the present invention are formulated for unit dosage administration, wherein the unit dosage is from about 0.5 to about 100 mg per day.

Methods of Administration

Administration of the peptides of the present invention with a suitable pharmaceutical excipient as necessary can be carried out via any of the accepted modes of administration. Thus, administration can be, for example, intravenous, topical, subcutaneous, transcutaneous, transdermal, intramuscular, oral, intra joint, parenteral, intra-arteriole, intradermal, intraventricular, intracranial, intraperitoneal, intralesional, intranasal, rectal, vaginal, or by inhalation. Administration can be targeted directly to pancreatic tissue, e.g., via injection.

The compositions of the invention may be administered repeatedly, e.g., at least 2, 3, 4, 5, 6, 7, 8, or more times, or the composition may be administered by continuous infusion. Suitable sites of administration include, but are not limited to, dermal, mucosal, bronchial, gastrointestinal, anal, vaginal, eye, and ear. The formulations may take the form of solid, semi-solid, lyophilized powder, or liquid dosage forms, such as, for example, tablets, pills, lozenges, capsules, powders, solutions, suspensions, emulsions, suppositories, retention enemas, creams, ointments, lotions, gels, aerosols, or the like, preferably in unit dosage forms suitable for simple administration of precise dosages.

The term "unit dosage form" refers to physically discrete units suitable as unitary dosages for human subjects, each unit containing a predetermined quantity of active material calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of a conjugate or a combination of conjugates.

Methods for preparing such dosage forms are known to those skilled in the art (see, for example, REMINGTON'S PHARMACEUTICAL SCIENCES, 18TH ED., Mack Publishing Co., Easton, Pa. (1990). The composition to be administered contains a quantity of the peptides of the invention in a pharmaceutically effective amount for improving beta islet cell survival. In addition, pharmaceutically acceptable salts of the peptides of the present invention (e.g., acid addition salts) may be prepared and included in the compositions using standard procedures known to those skilled in the art of synthetic organic chemistry and described, e.g., by March, Advanced Organic Chemistry: Reactions, Mechanisms and Structure, 4th Ed., New York, Wiley-Interscience (1992).

In another approach, nucleic acids encoding the polypeptides of the invention are used for transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acids, under the control of a promoter, then express a polypeptide of the present invention, thereby mitigating the effects of a disease associated with reduced insulin production.

Such gene therapy procedures have been used to correct acquired and inherited genetic defects, cancer, and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science*, 256:808-813 (1992); Nabel et al., *TIBTECH*, 11:211-217 (1993); Mitani et al., *TIBTECH*, 11:162-166 (1993); Mulligan, *Science*, 926-932 (1993); Dillon, *TIBTECH*, 11:167-175 (1993); Miller, *Nature*, 357: 455-460 (1992); Van Brunt, *Biotechnology*, 6(10):1149-1154 (1998); Vigne, *Restorative Neurology and Neuroscience*, 8:35-36 (1995); Kremer et al., *British Medical Bulletin*, 51(1):31-44 (1995); Haddada et al., in *Current Topics in Microbiology and Immunology* (Doerfler & Bohm eds., 1995); and Yu et al., *Gene Therapy*, 1:13-26 (1994)).

For delivery of nucleic acids, viral vectors may be used. Suitable vectors include, for example, herpes simplex virus vectors as described in Lilley et al., *Curr. Gene Ther.*, 1(4):339-58 (2001), alphavirus DNA and particle replicons as described in e.g., Polo et al., *Dev. Biol.* (Basel), 104:181-5 (2000), Epstein-Barr virus (EBV)-based plasmid vectors as described in, e.g., Mazda, *Curr. Gene Ther* 2(3):379-92 (2002), EBV replicon vector systems as described in e.g., Otomo et al., *J. Gene Med.*, 3(4):345-52 (2001), adenovirus associated viruses from rhesus monkeys as described in e.g., Gao et al., *PNAS USA*, 99(18):11854 (2002), adenoviral and adeno-associated viral vectors as described in e.g., Nicklin et al., *Curr. Gene Ther.*, 2(3):273-93 (2002). Other suitable adeno-associated virus (AAV) vector systems can be readily constructed using techniques well known in the art (see, e.g., U.S. Pat. Nos. 5,173,414 and 5,139,941; PCT Publication Nos. WO 92/01070 and WO 93/03769; Lebkowski et al., *Mol. Cell. Biol.*, 8:3988-3996 (1988); Vincent et al. (1990) Vaccines 90 (Cold Spring Harbor Laboratory Press); Carter, *Current Opinion in Biotechnology* 3:533-539 (1992); Muzyczka, *Current Topics in Microbiol. and Immunol.*, 158:97-129 (1992); Kotin, *Human Gene Therapy*, 5:793-801 (1994); Shelling et al., *Gene Therapy*, 1:165-169 (1994); and Zhou et al., *J. Exp. Med.*, 179:1867-1875 (1994)). Additional suitable vectors include E1B gene-attenuated replicating adenoviruses described in, e.g., Kim et al., *Cancer Gene Ther* 9(9):725-36 (2002) and nonreplicating adenovirus vectors described in e.g., Pascual et al., *J. Immunol.*, 160(9):4465-72 (1998) Exemplary vectors can be constructed as disclosed by Okayama et al., *Mol. Cell. Biol.*, 3:280 (1983).

In some embodiments, this invention comprises an expression vector comprising a nucleic acid sequence that encodes SEQ ID NO:1. In some embodiments, this invention comprises an expression vector comprising a nucleic acid sequence that encodes a peptide at least 70%, 75%, 80%, 85%, 90%, 95%, 97% or 100% identical to SEQ ID NO:1. In some embodiments, this invention comprises an expression vector comprising a cDNA at least 70%, 75%, 80%, 85%, 90%, 95%, 97% or 100% identical to SEQ ID NO:2.

Molecular conjugate vectors, such as the adenovirus chimeric vectors described in Michael et al., J. Biol. Chem., 268:6866-6869 (1993) and Wagner et al., Proc. Natl. Acad. Sci. USA, 89:6099-6103 (1992), can also be used for gene delivery according to the methods of the invention.

In one illustrative embodiment, retroviruses provide a convenient and effective platform for gene delivery systems. A selected nucleotide sequence encoding a polypeptide of the invention is inserted into a vector and packaged in retroviral particles using techniques known in the art. The recombinant virus can then be isolated and delivered to a subject. Suitable vectors include lentiviral vectors as described in e.g., Scherr et al., Curr. Gene Ther., 2(1):45-55 (2002). Additional illustrative retroviral systems have been described (e.g., U.S. Pat. No. 5,219,740; Miller et al., *BioTechniques*, 7:980-990 (1989); Miller, *Human Gene Therapy*, 1:5-14 (1990); Scarpa et al., *Virology*, 180:849-852 (1991); Bums et al., *Proc. Natl. Acad. Sci. USA*, 90:8033-8037 (1993); and Boris-Lawrie et al., *Curr. Opin. Genet. Develop.*, 3:102-109 (1993).

Other known viral-based delivery systems are described in, e.g., Fisher-Hoch et al., *Proc. Natl. Acad. Sci. USA*, 86:317-321 (1989); Flexner et al., *Ann. N.Y. Acad. Sci.*, 569:86-103 (1989); Flexner et al., *Vaccine,* 8:17-21 (1990); U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques,* 6:616-627 (1988); Rosenfeld et al., *Science,* 252:431-434 (1991); Kolls et al., *Proc. Natl. Acad. Sci. USA,* 91:215-219 (1994); Kass-Eisler et al., *Proc. Natl. Acad. Sci. USA,* 90:11498-11502 (1993); Guzman et al., *Circulation,* 88:2838-2848 (1993); Guzman et al., *Cir. Res.,* 73:1202-1207 (1993); and Lotze et al., *Cancer Gene Ther.,* 9(8):692-9 (2002).

Therapeutic and Prophylactic Applications

In certain aspects, the compositions of the invention are used for the treatment or prevention of a disease or disorder in a subject in need thereof. Examples of diseases or disorders suitable for treatment with the MOTS3 or MOTS3 analogue compositions described herein include, but are not limited to, treating and preventing disorders which include but are not limited to Type 1 and Type 2 diabetes, gestational diabetes, pre-diabetes, insulin resistance, metabolic syndrome, impaired glucose tolerance, cancers (e.g., breast cancer, brain cancer, colon cancer, melanoma, leukemia (e.g., AML), lymphoma, pancreatic cancer, prostate cancer, ovarian cancer, lung cancer, and gastric cancer), obesity, and fatty liver disease. The compositions of the invention can be used prophylactically, e.g., for individuals with a genetic predisposition for diabetes.

One of skill in the art will appreciate that the MOTS3 peptides and analogues of the invention can be co-administered with other therapeutic agents for the treatment or prevention of any of the diseases described herein. Co-administration can be simultaneous, e.g., in a single pharmaceutical composition or separate compositions. The compositions of the invention can also administered separately from the other therapeutic agent(s), e.g., on an independent dosing schedule.

EXAMPLES

Example 1

3' RACE analysis revealed that MOTS3 is polyadenylated, similar to HN (FIG. 1A). After initial screening as described below, MOTS 3 was determined to have potent biological activity, and its peptide sequence is well conserved in various species (FIG. 1B). We have generated anti-MOTS3 polyclonal rabbit antibodies that can detect endogenous and overexpressed MOTS3 by cloning the ORF into an expression vector in cell culture as well GFP-tagged MOTS3 (FIG. 1C). Using these validated antibodies, we can detect MOTS3 in rat heart, liver, and testis at similar molecular weights and in the brain at a slightly higher molecular weight (FIG. 1D). The expression level appears to be highest in the heart, an organ with one of the highest mitochondrial density. Further, rho-O HeLa cells, which have been purged of mitochondrial DNA using ethidium bromide, do not express MOTS3 as well as other well described mitochondria-encoded proteins such as cytochrome oxidase I and II (COI and COII), confirming its mitochondrial origin (FIG. 1E).

Example 2

Figures 2A, 2B:
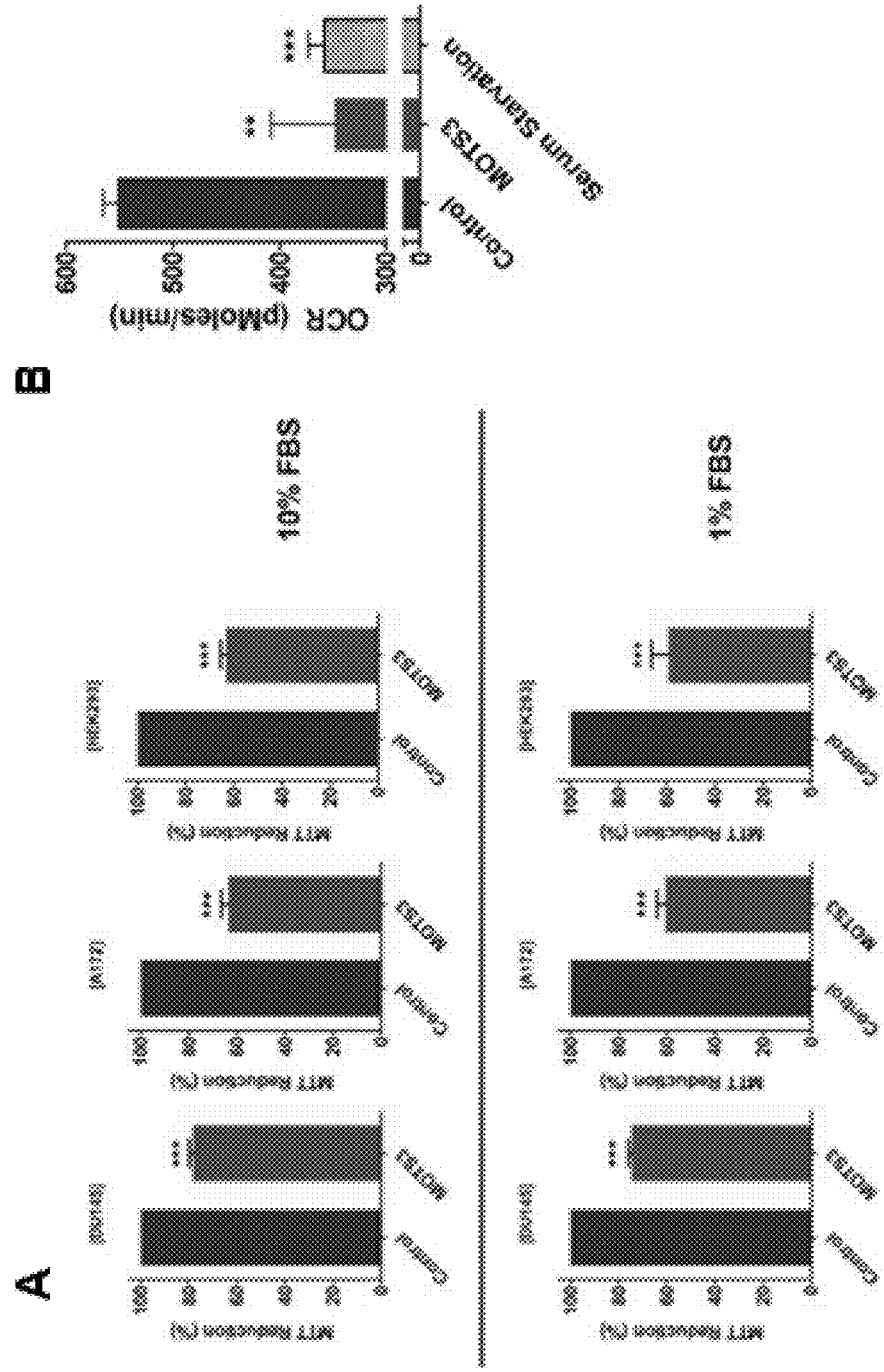
FIG. 2A-FIG. 2B depicts the effect of MOTS3 on mitochondrial activity under 10% and 1% FBS culture conditions (A). MTT reduction by mitochondrial reductase enzymes and oxygen consumption rate (OCR) and extracellular acidification rate (ECAR; measures glycolysis by pH changes in the medium made by lactate secretion) (B).
Figure 3:
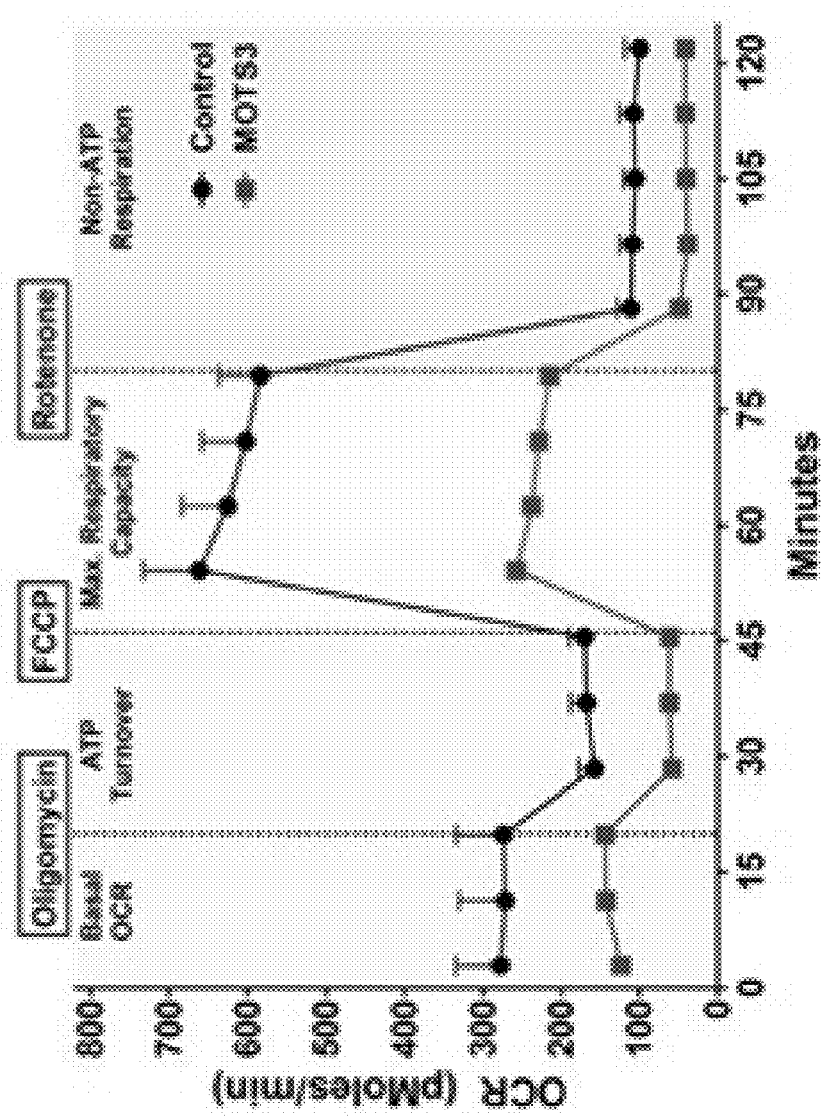
FIG. 3 depicts the effect of exogenous MOTS3 treatment on mitochondrial respiration. Each drug was treated to test the specific metabolic parameter described at the top of the chart; i.e. oligomycin-ATP turnover, FCCP-maximum respiratory capacity, Rotenone-non-ATP respiration.
Figures 4A, 4B:
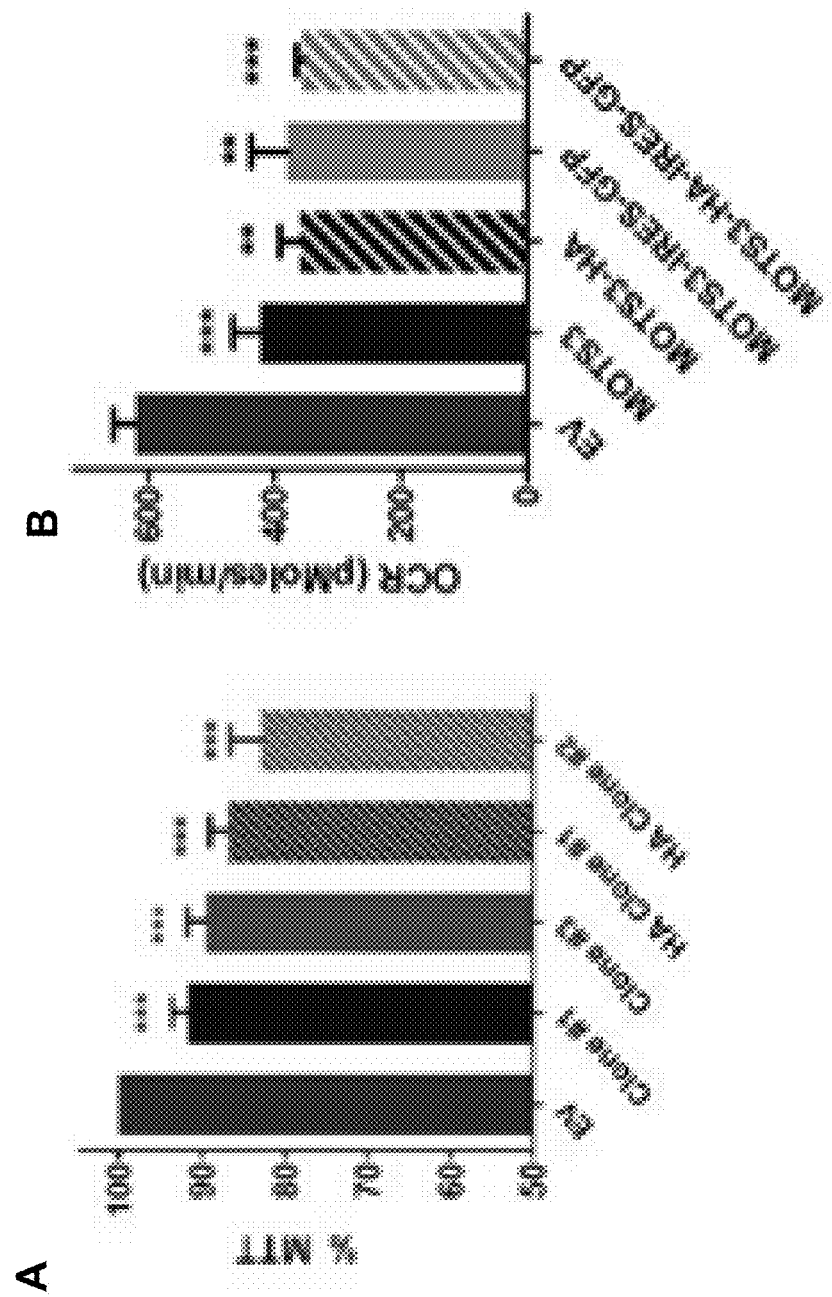
FIG. 4A-FIG. 4B depicts the effect of MOTS3 overexpression by transfection on mitochondrial activity. Various versions of MOTS3 were cloned and expressed in cells.
Figures 5A, 5B, 5C:
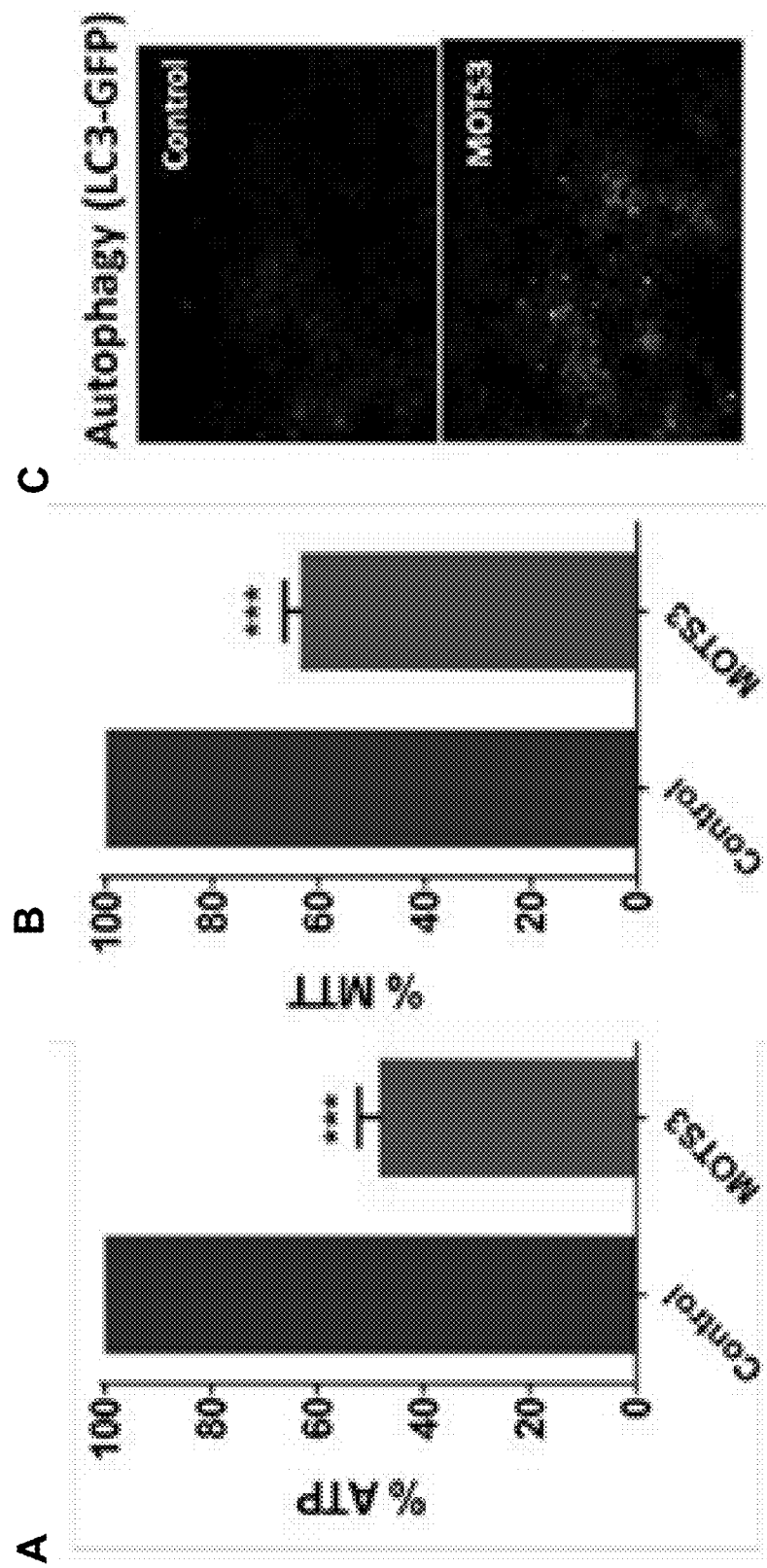
FIG. 5A-FIG. 5C depicts the effect of exogenous MOTS3.

Exogenous treatment of synthetic MOTS3 causes a mitochondria-dependent metabolic shift, measured by oxygen consumption rate (OCR) measured by Seahorse technology as wells as MTT reduction (under 10% and 1% FBS conditions) (FIG. 2). Both exogenous MOTS 3 treatments with synthetic peptides (FIG. 3), as well as the endogenous expression by cloning (FIG. 4) inhibited mitochondrial activity. Notably, exogenous MOTS3 treatment reduced cellular ATP levels and mitochondrial activity (MTT), which simultaneously occurred with increased autophagy (FIG. 5).

Figures 6A, 6B, 6C, 6D:
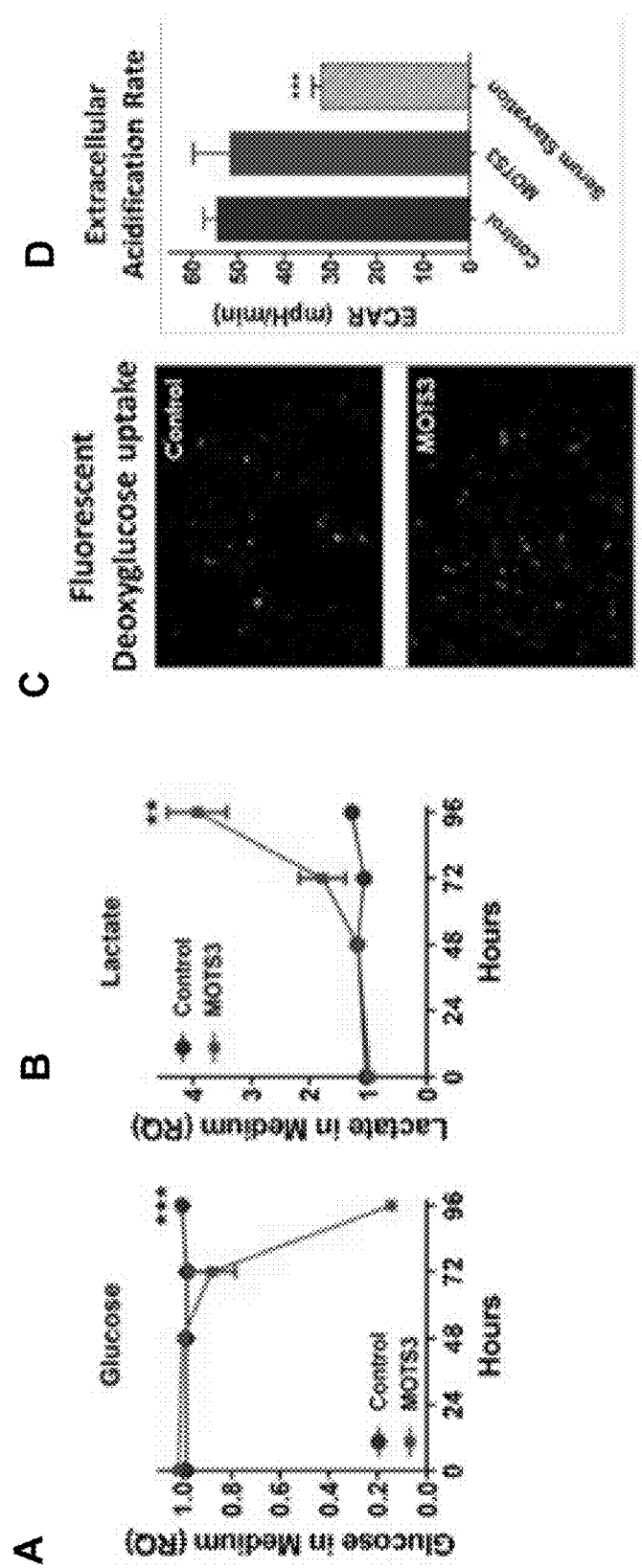
FIG. 6A-FIG. 6D depicts the effect of exogenous MOTS3 treatment on glucose uptake and glycolysis.
Figure 7:
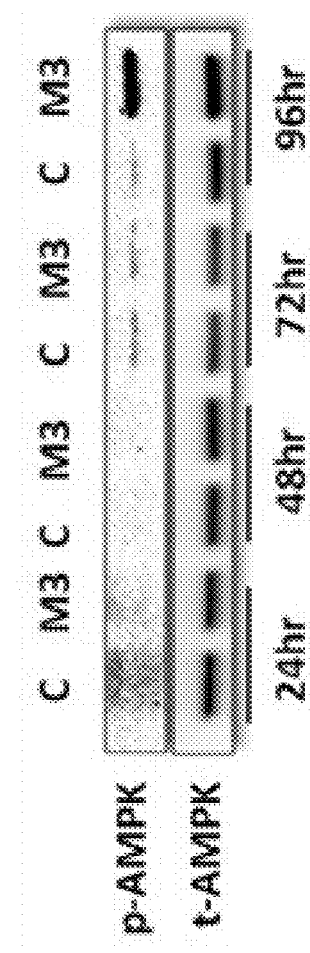
FIG. 7 shows that MOTS3 (M3) significantly induces AMPK activation compared to the control group (C) following 96 hours of treatment. This correlates with the sharp decrease in glucose availability in the medium following 96 hours of treatment in FIG. 6.
Figures 8A, 8B:
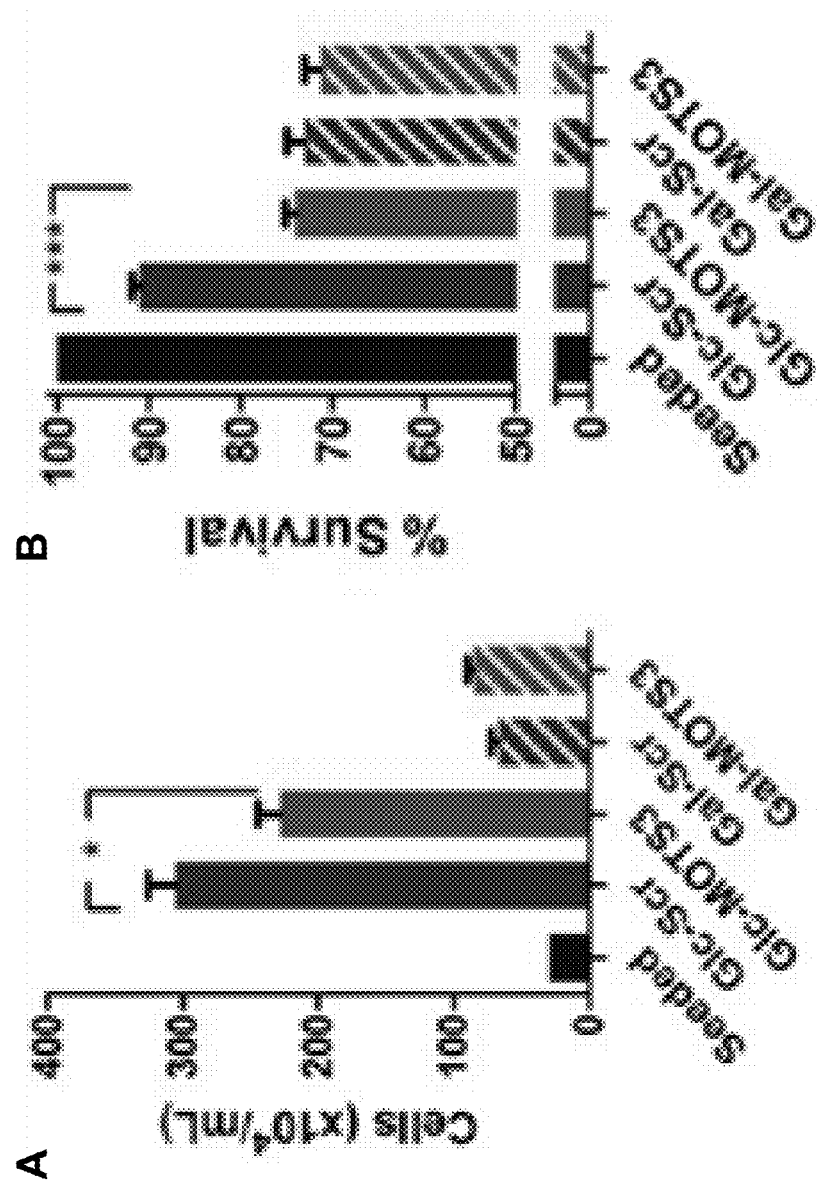
FIG. 8A-FIG. 8B shows that MOTS3 retards cellular proliferation and survival in glucose medium, but not in galactose medium which forces the cells to rely largely on mitochondrial function for survival.

MOTS3 treatment induced an increase in glucose uptake as measured by residual glucose levels in the culture medium and by fluorescence-labeled glucose analog uptake (FIG. 6A and FIG. 6B). As expected, lactate secretion was increased in keep with elevated glucose consumption (FIG. 6A). Notably, by 96 hours of MOTS3 treatment, when most of the glucose in the medium has been consumed, AMPK activation is significantly higher in the MOTS3 treated cells (FIG. 7), agreeing with the sharp decrease in cellular ATP levels and increased autophagy as shown in FIG. 5. Impaired cellular metabolism induced by exogenous MOTS3 led to reduced cellular proliferation and survival under glucose medium but not galactose medium (FIG. 8); galactose forces the cells to rely on mitochondrial metabolism for survival.

Figure 9A:
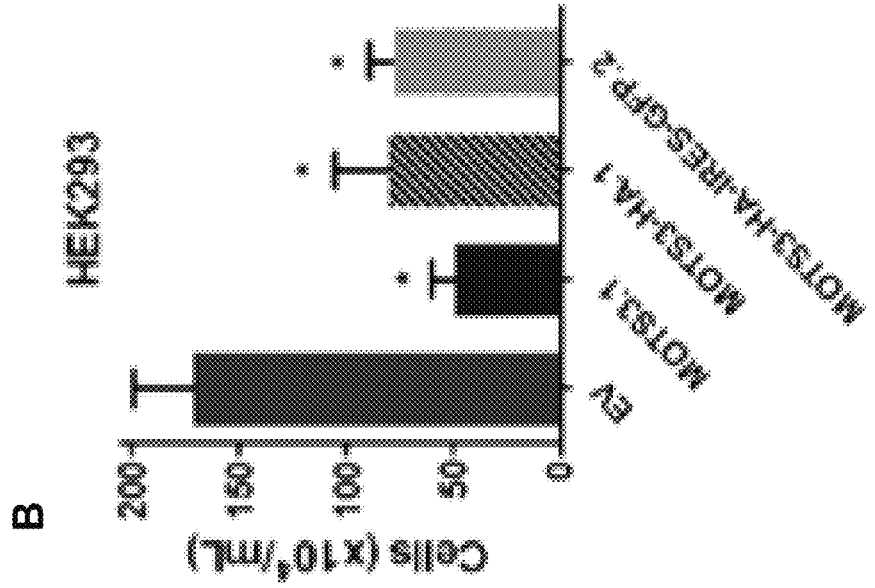
FIG. 9A-FIG. 9B depicts the effect of intracellular expression of MOTS3 on cellular proliferation. MOTS3 was cloned into expression vectors and transfected into cells.
Figure 9B:
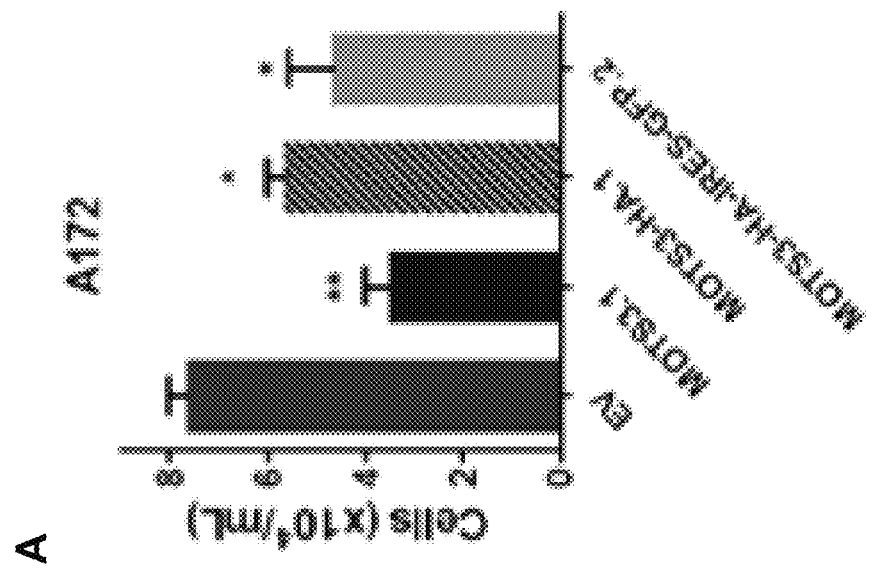
Figure 10:
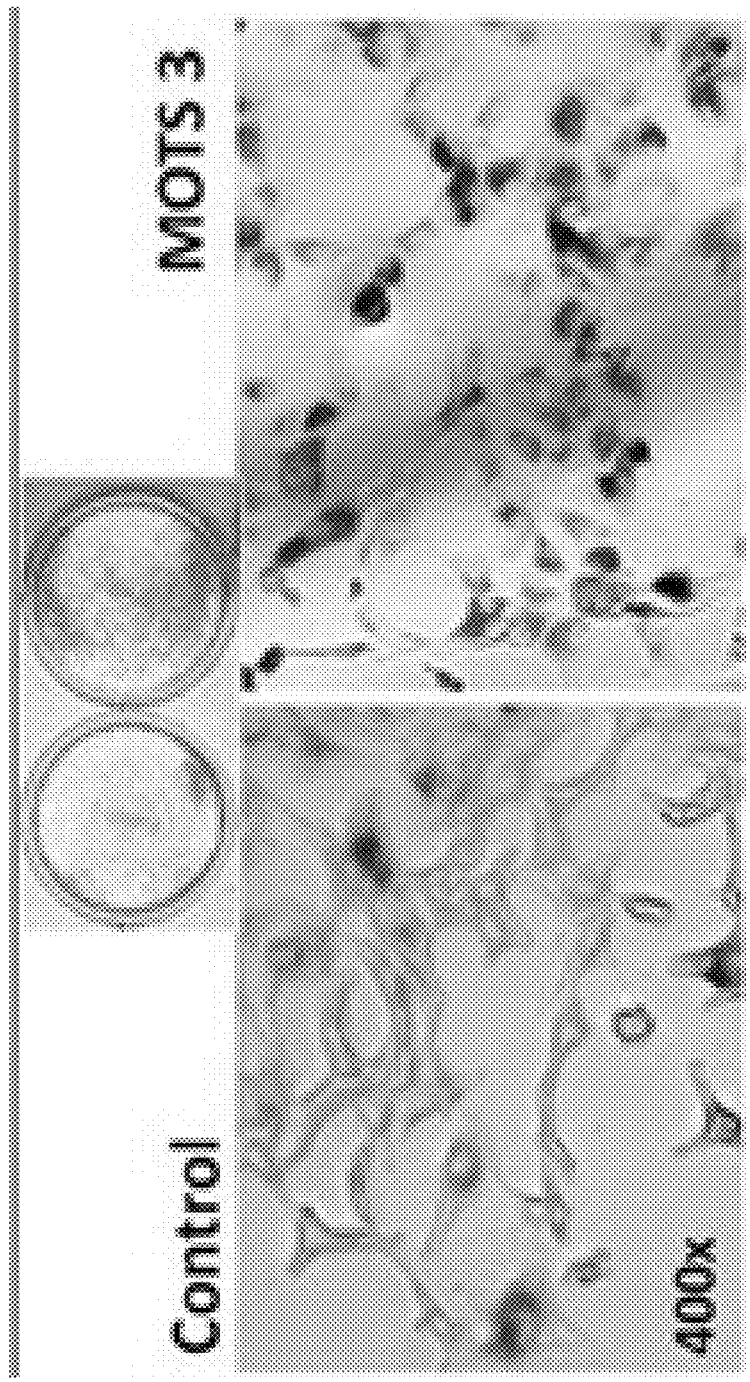
FIG. 10 depicts the effect of exogenous MOTS 3 on cellular senescence. Senescence was determined by senescence associated β-galactosidase levels (blue).

Intracellular MOTS3 overexpression by transfecting expression clones also retarded cellular proliferation (FIG. 9). Interestingly, 8 days of exogenous MOTS 3 treatment induced cellular senescence as measured by senescence associated β-galactosidase staining (FIG. 10).

Example 3

In mice, 4 days of MOTS3 injections (i.p.; 0.5 or 5.0 mg/kg/day) led to significant weight loss without significant alteration of food intake (FIG. 11). Further, in agreement with our in vitro studies, liver mitochondrial respiration capacity was diminished following MOTS3 treatment at both tested doses (FIG. 11). Notably, MOTS3 treatment significantly reduced blood glucose levels (FIG. 12A) and also had higher insulin levels (FIG. 12B), suggesting increased glucose uptake similar to that observed in cell culture (FIG. 6).

Example 4

MOTS-c: A Novel Peptide Encoded within the Mitochondrial Genome that Prevents Obesity and Regulates Metabolic Homeostasis Abstract The mitochondrial genome is traditionally known to encode for only 13 proteins, which are translated using a mitochondria-specific genetic code. This has been recently challenged with the discovery of humanin, a peptide encoded within the mitochondrial 16S rRNA. Humanin suggests the possible existence of unexplored mitochondrial genes that give rise to bioactive peptides (C. Lee, K. Yen, P. Cohen, *Humanin: a harbinger of mitochondrial-derived peptides? Trends in endocrinology and metabolism: TEM,* (Feb. 7, 2013)). Here we report a novel peptide encoded within the mitochondrial 12S rRNA, named MOTS-c ( mitochondrial open-reading-frame of the twelve SrRNA c), which was detected in various tissues and in circulation. MOTS-c acts as a key regulator of metabolic homeostasis by modulating nucleotide, glucose, mitochondrial, and fatty acid metabolism. Notably, MOTS-c caused a >20-fold increase in endogenous AICAR levels, via the de novo purine biosynthesis pathway, and also activated AMPK signaling in HEK293 cells and skeletal muscle in mice. MOTS-c treatment in mice prevented high fat diet-induced weight gain and insulin resistance. Furthermore, coinciding with age-dependent insulin resistance in muscle, MOTS-c levels were found to decline with age in plasma and muscle, and MOTS-c treatment sufficiently restored insulin sensitivity in older mice. The discovery of MOTS-c, along with humanin, suggests previously unknown regulatory roles for mitochondria in coordinating critical cellular processes, including metabolism. Our findings suggest that mitochondrial-derived peptide (MDP) including MOTS-c not only unravels novel mitochondrial biology, but may also provide novel diagnostic biomarkers and therapeutic targets that can be exploited to ameliorate metabolic dysfunctions associated with aging and age-related chronic diseases.

Figure 13A:
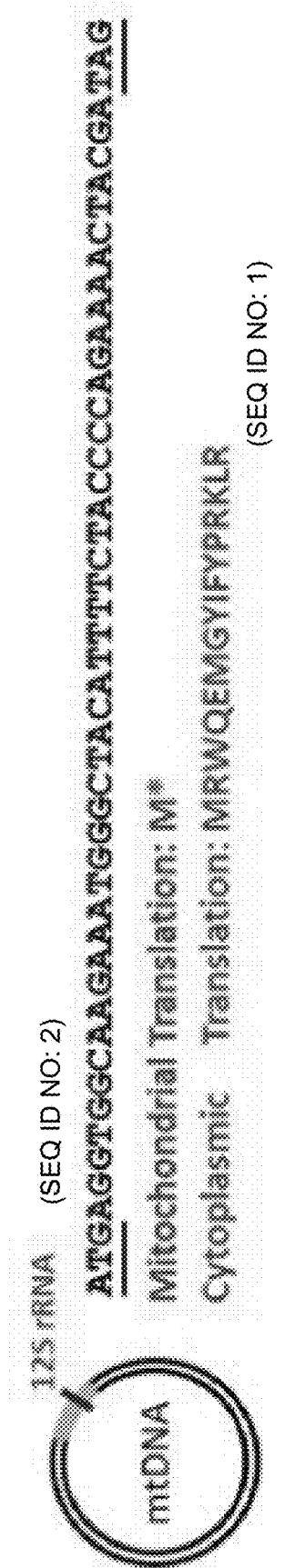
Figure 13B:
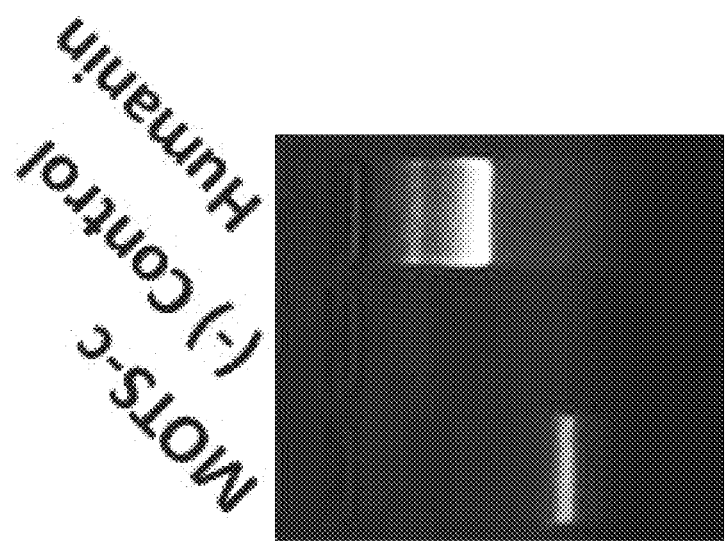
Figures 17A, 17B, 17C, 17D, 17E, 17F:
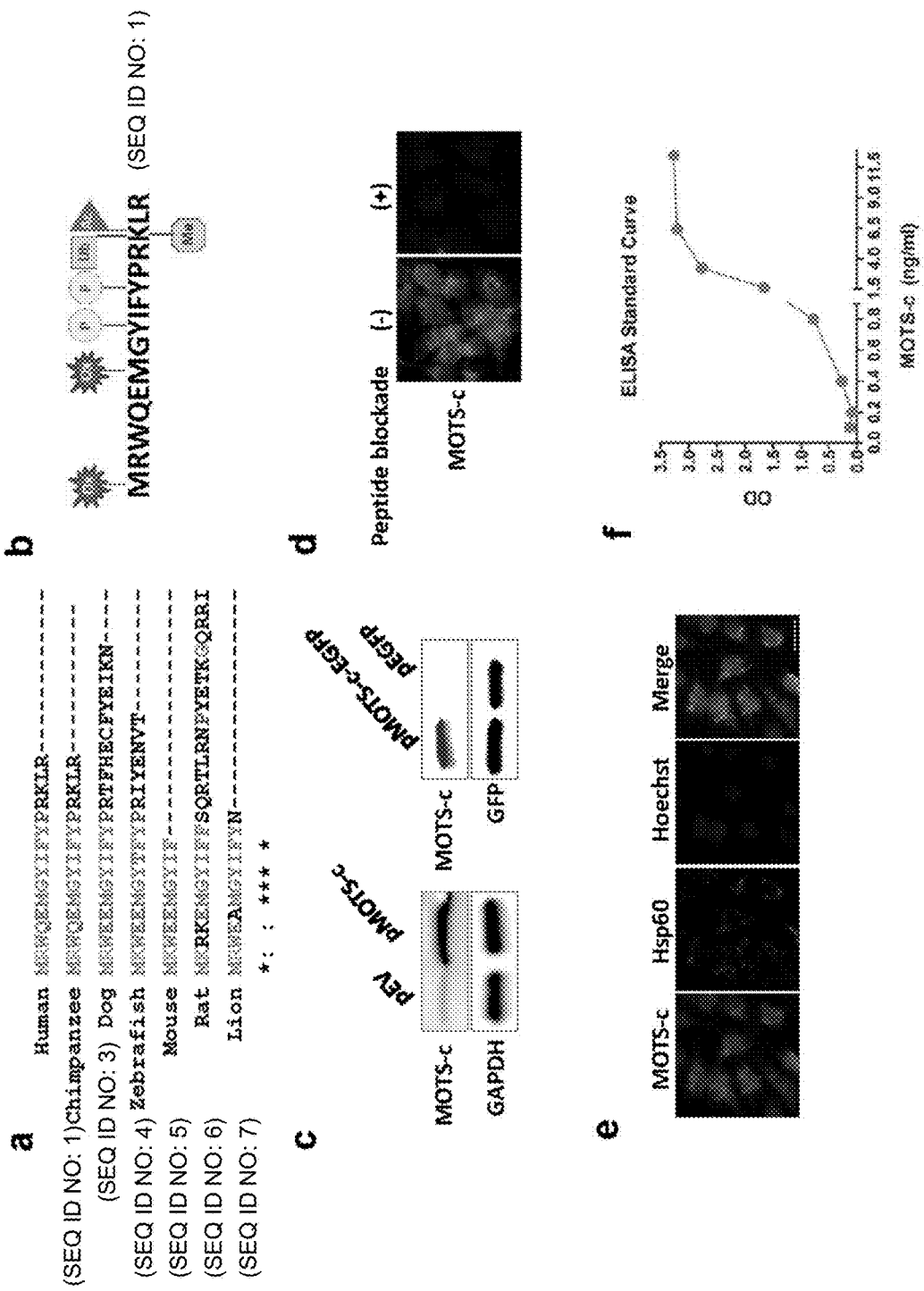
FIG. 17A-FIG. 17F describes a, MOTS-c peptide sequence is highly conserved. b, putative post-translational modifications of MOTS-c. c, MOTS-c antibodies were generated and tested for specificity against MOTS-c by immunoblotting. Western blots showing MOTS-c detection from HEK293 cells transfected with pEV, pMOTS-c, pMOTS-c-EGFP, pEGFP. d, HEK293 cells were stained with anti-MOTS-c antibody (green) alone or in the presence of MOTS-c peptide (blocking). e, MOTS-c (green) and hsp60 (red) immunostaining in HEK293 cells. Nuclei were stained with Hoechst 33258 (blue). Scale bar, 20 μm. f, standard-curve of an in-house MOTS-c ELISA, which was used to measure MOTS-c in plasma.

An in silico search for potential open reading frames (ORFs) encoding bioactive peptides within the 12S rRNA region of the mitochondrial DNA (mtDNA) was conducted. MOTS-c was identified as a 51 bp open reading frame (ORF) that translates into a 16 amino acid peptide (FIG. 13a), which is highly conserved (FIG. 17a). This peptide is also subject to several putative post-translation modifications (FIG. 17b). Translation of MOTS-c could theoretically be either mitochondrial or cytoplasmic, but because the mitochondrial genetic code yields tandem start/stop codons (FIG. 13a), MOTS-c must undergo cytoplasmic translation, indicating that its polyadenylated transcript (FIG. 13b) is exported from the mitochondria by a currently unknown mechanism (Y. Ninomiya, S. Ichinose, *Subcellular distribution of mitochondrial ribosomal RNA in the mouse oocyte and zygote. PloS one* 2, e1241 (2007) and R. Amikura, M. Kashikawa, A. Nakamura, S. Kobayashi, *Presence of mitochondria-type ribosomes outside mitochondria in germ plasm of Drosophila embryos. Proceedings of the National Academy of Sciences of the United States of America* 98, 9133 (Jul. 31, 2001)).

Figure 13D:
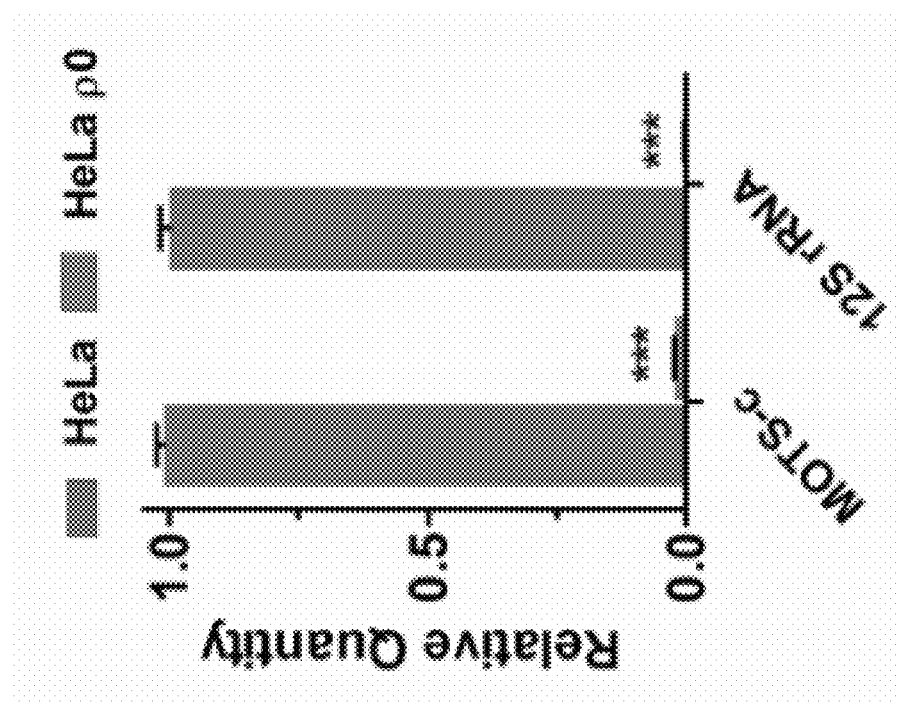
Figure 13E:
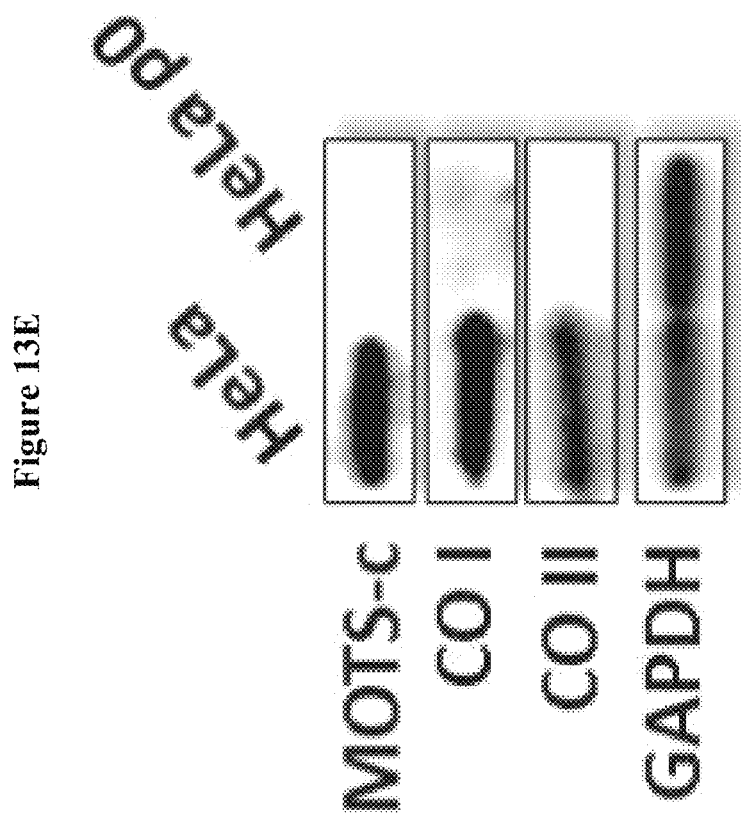
Figure 13F:
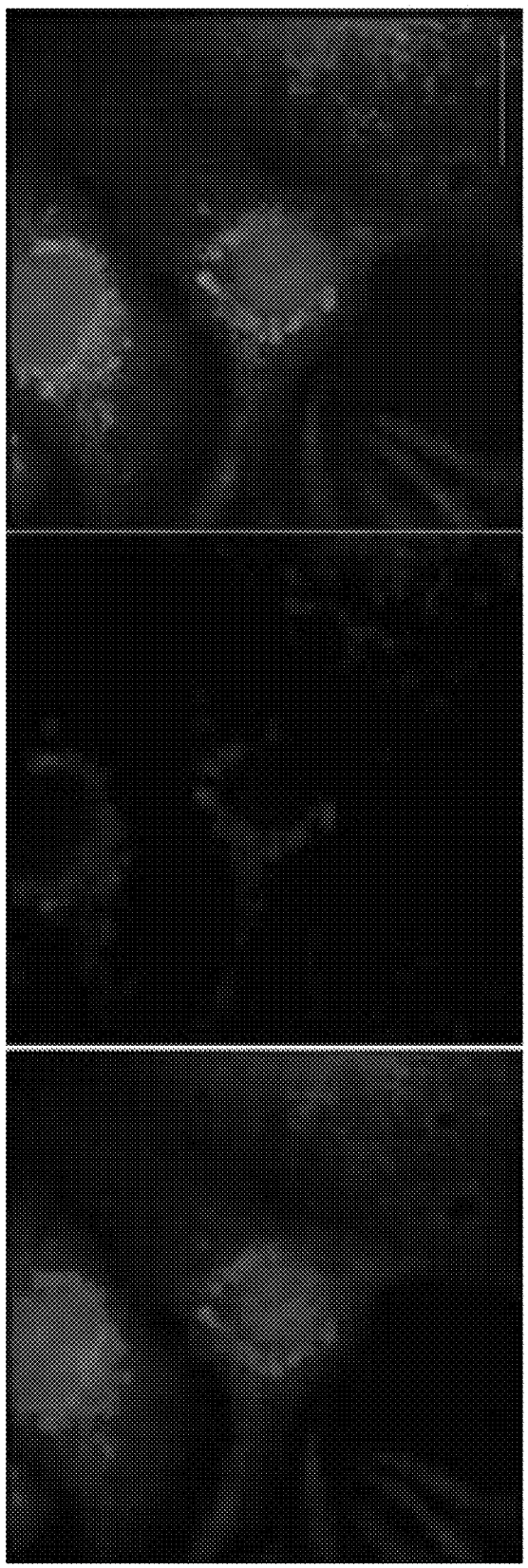
Figure 13G:
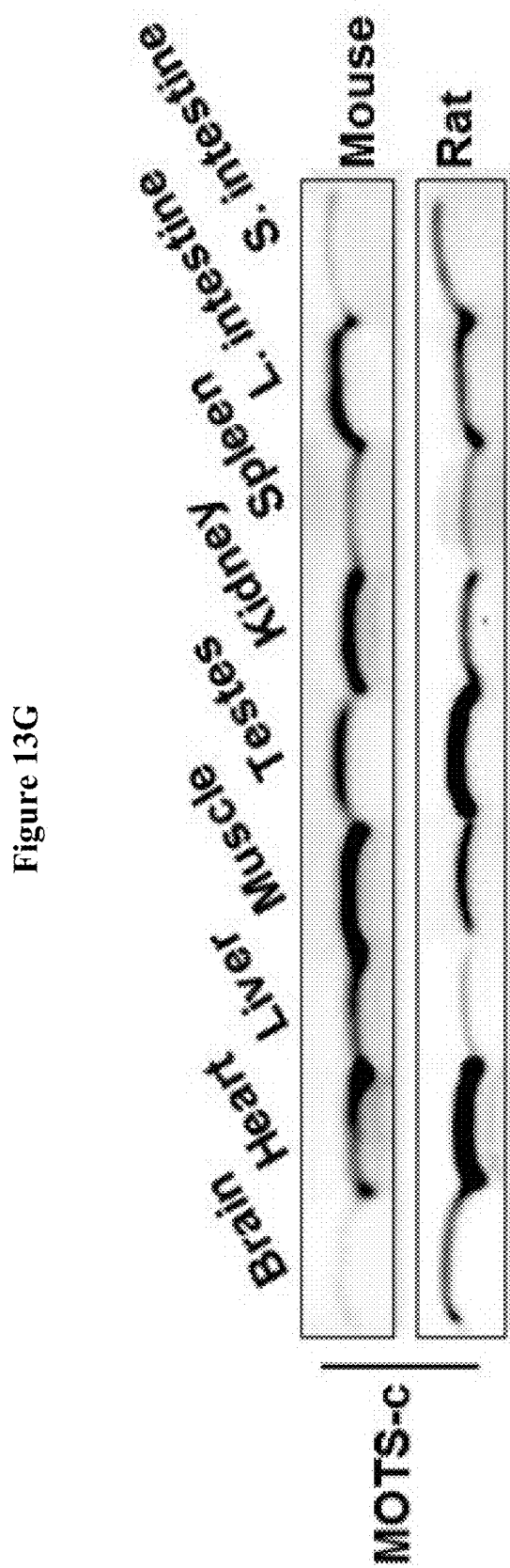
Figure 13H:
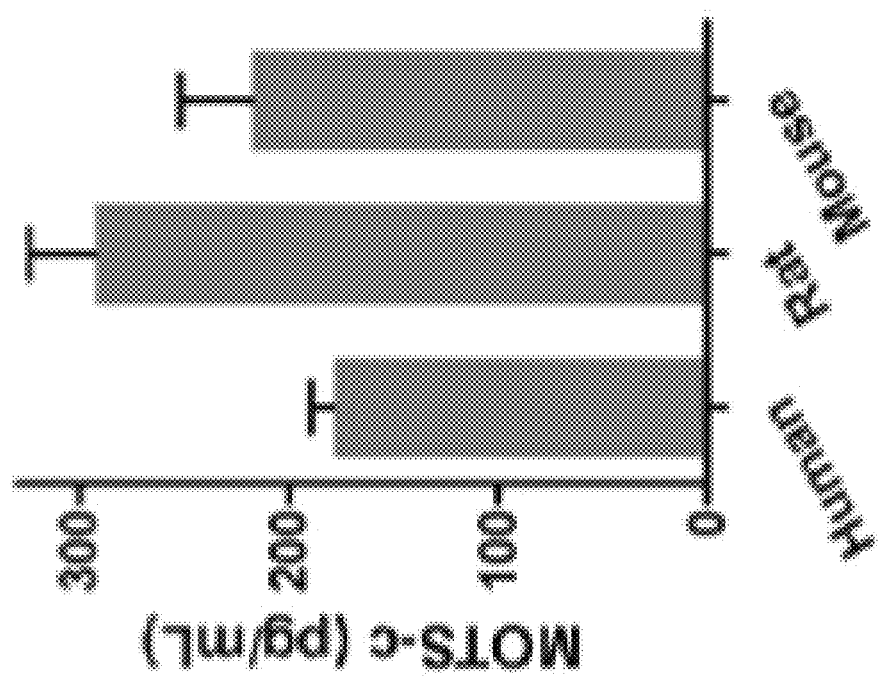
Figure 13I:
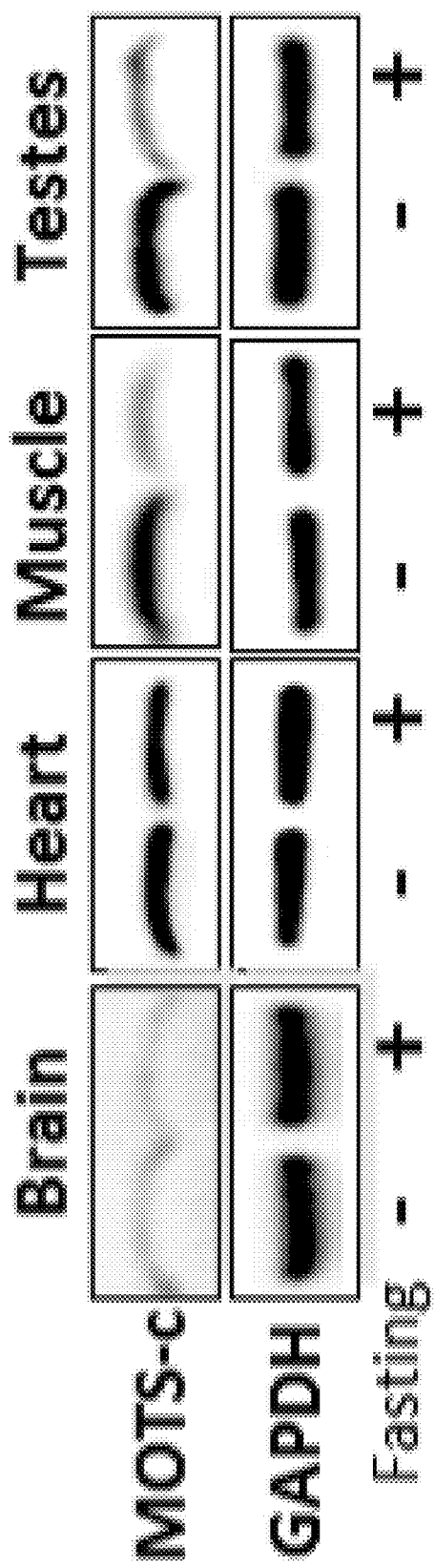
Figure 13J:
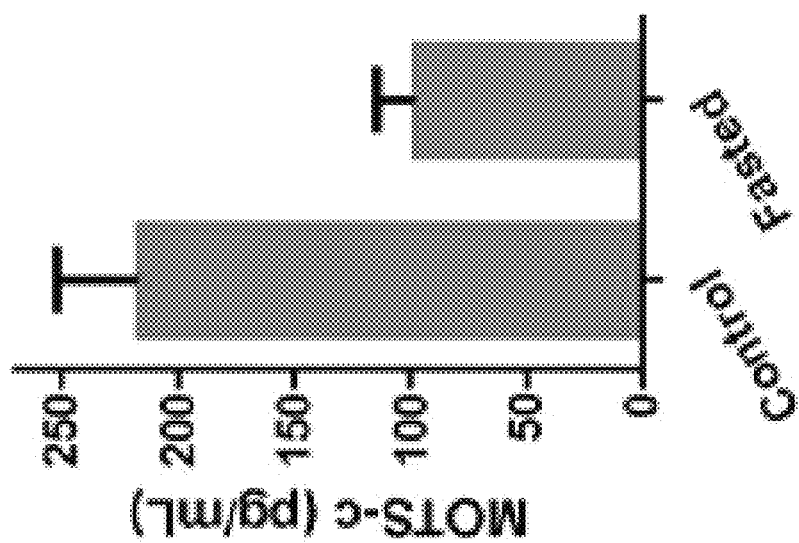

The possibility that MOTS-c could also be of nuclear origin due to a phenomenon known as nuclear mitochondrial DNA transfer (NUMT) (M. Ricchetti, F. Tekaia, B. Dujon, *Continued colonization of the human genome by mitochondrial DNA. PLoS biology* 2, E273 (September, 2004)) was recognized. Using the NCBI nucleotide basic local alignment search tool (BLAST), it was found that none of the NUMTs or their peptide products had complete homology to the mitochondrial MOTS-c sequence (FIG. 13c). To further confirm its mitochondrial origin, MOTS-c expression in HeLa cells that have been selectively depleted of mitochondrial DNA (ρ0) was measured. In HeLa-ρ0 cells, both 12S rRNA and MOTS-c transcript were undetectable by qRT-PCR (FIG. 13d), and immunoblots using MOTS-c specific antibodies (FIG. 17c) showed undetectable levels of mitochondrial-encoded cytochrome oxidase I and II (COI/II) and MOTS-c, but unaltered expression of nuclear-encoded GAPDH (FIG. 13e). To study its subcellular distribution pattern, HEK293 cells were immunostained for MOTS-c and observed mitochondrial colocalization (FIG. 13f; FIG. 17d, 17e). MOTS-c was detected in various tissues in mice and rats (FIG. 13g), as well as in circulation in human and rodent plasma (FIG. 13h; FIG. 17f). Notably, fasting altered the endogenous expression of MOTS-c in certain metabolically active tissues (FIG. 13i), and in plasma (FIG. 13j).

Figure 14A:
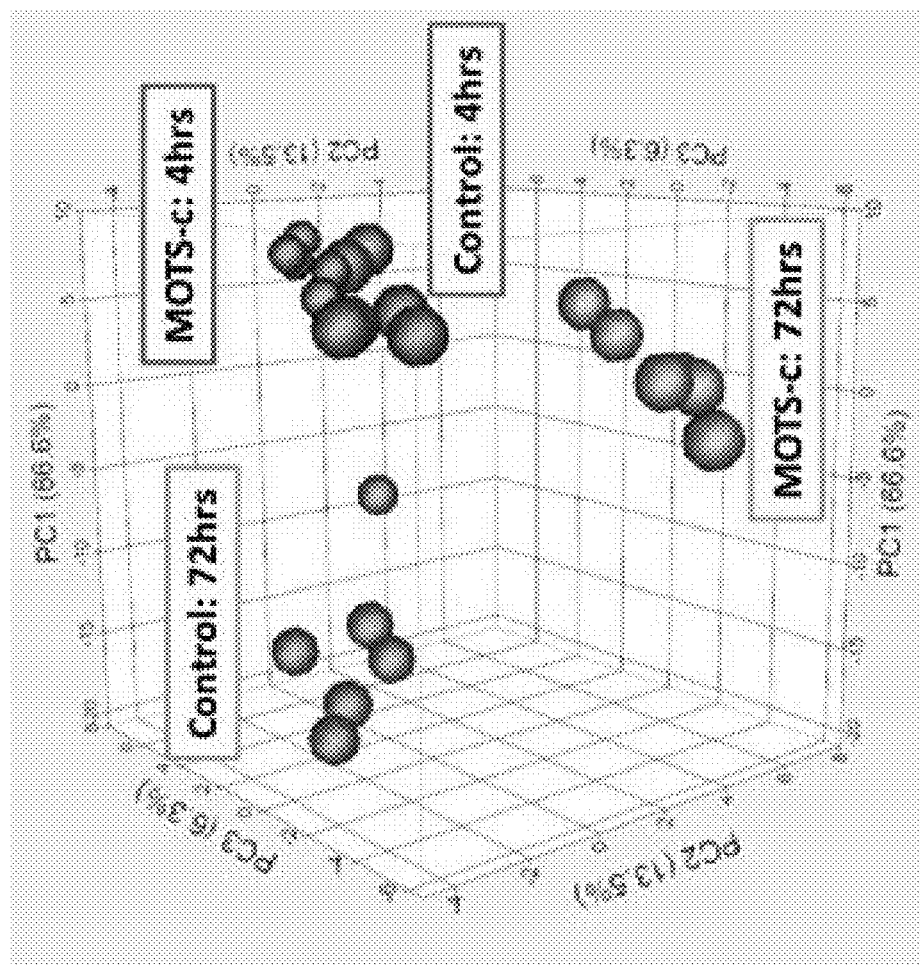
FIG. 14A-FIG. 14I describes MOTS-c modulates gene expression and regulates metabolism via AICAR and AMPK signaling. a, Principal component analysis (PCA) on HEK293 cells after 4- and 72-hours of MOTS-c treatment (10 μM; N=6). b, Parametric analysis of gene set enrichment (PAGE) further showed time-dependent global gene expression changes (N=6). c, Venn diagram depicting upregulated genes (Red) and downregulated genes (Blue) is shown per time point (N=6). d, Effect of 72 hours of MOTS-c treatment in HEK293 cells (10 μM; N=6) on various gene sets related to metabolism and inflammation. e, The effect of MOTS-c on de novo purine biosynthesis. The pentose phosphate pathway (PPP) and $NAD^+$ feed into the de novo purine biosynthesis pathway (N=5). Enzymes altered by 4- and 72-hours of MOTS-c were determined by microarray analysis (FIG. 18b). GAR: glycinamide ribonucleotide, FGAM: N-formylglycinamidine ribonucleotide, AIR: aminoimidazole ribonucleotide, NCAIR: N5-carboxyaminoimidazole ribonucleotide, SAICAR: N-succinocarboxamide-5-aminoimidazole ribonucleotide. Colors indicate changes by MOTS-c; Red: upregulation, blue: downregulation, and gray: unmeasured. f, HEK293 stably over-expressing MOTS-c have significantly increased AICAR levels (N=5). g, Metabolic intermediates of the de novo purine biosynthesis pathway in HEK293 cells stably over-expressing MOTS-c are shown (N=5). h, AICAR is a potent activator of AMPK. MOTS-c activates AMPK and its downstream pathways control fatty acid oxidation (ACC and CPT-1), and glucose uptake (GLUT-4). i, MOTS-c promotes AMPK and Akt phosphorylation in a time- and dose-dependent manner. Data shown as mean±SEM. Student's t-test. *P<0.05, P<0.01, *P<0.001
Figures 14B, 14C, 14D:
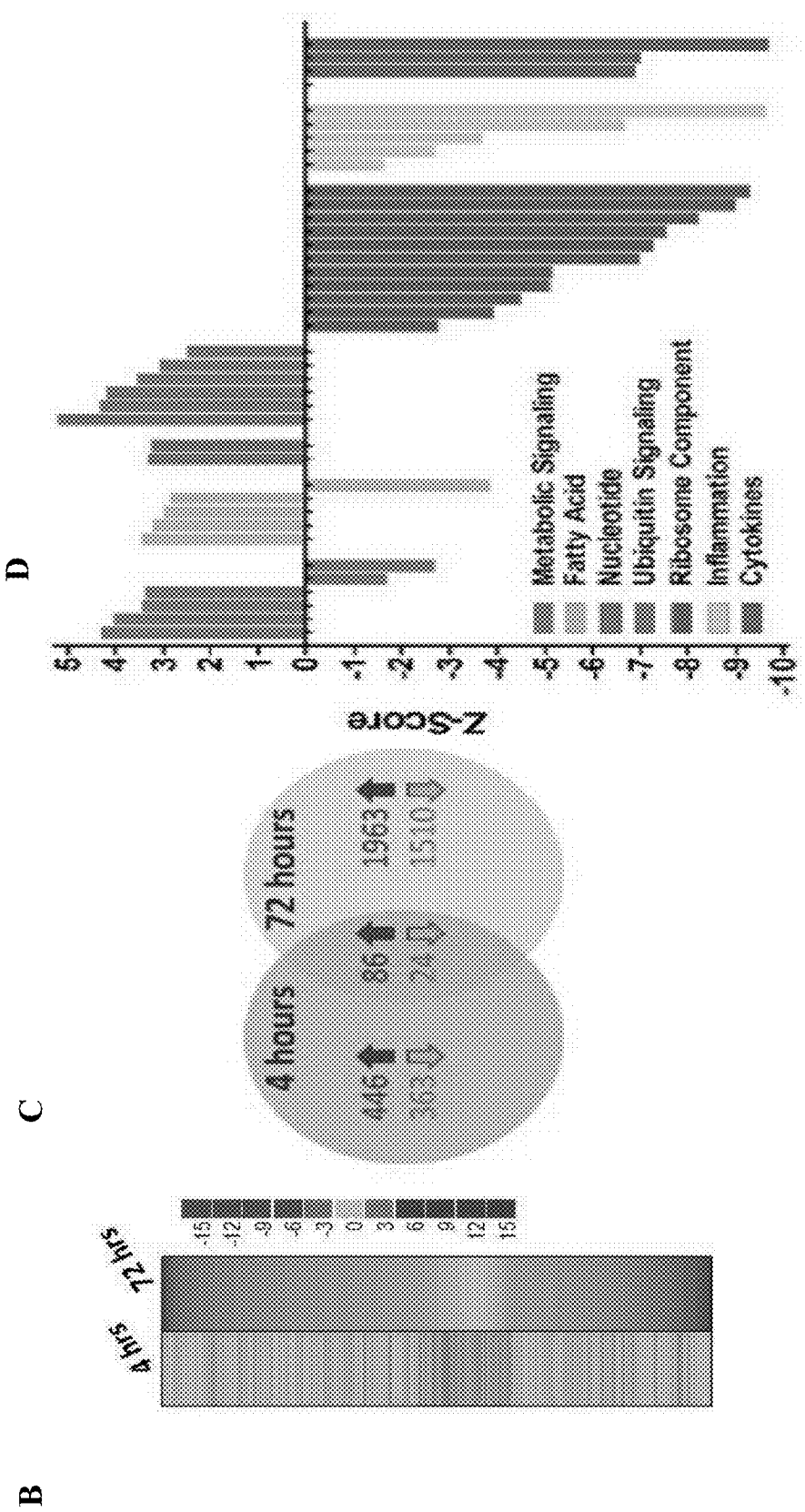
Figure 30:
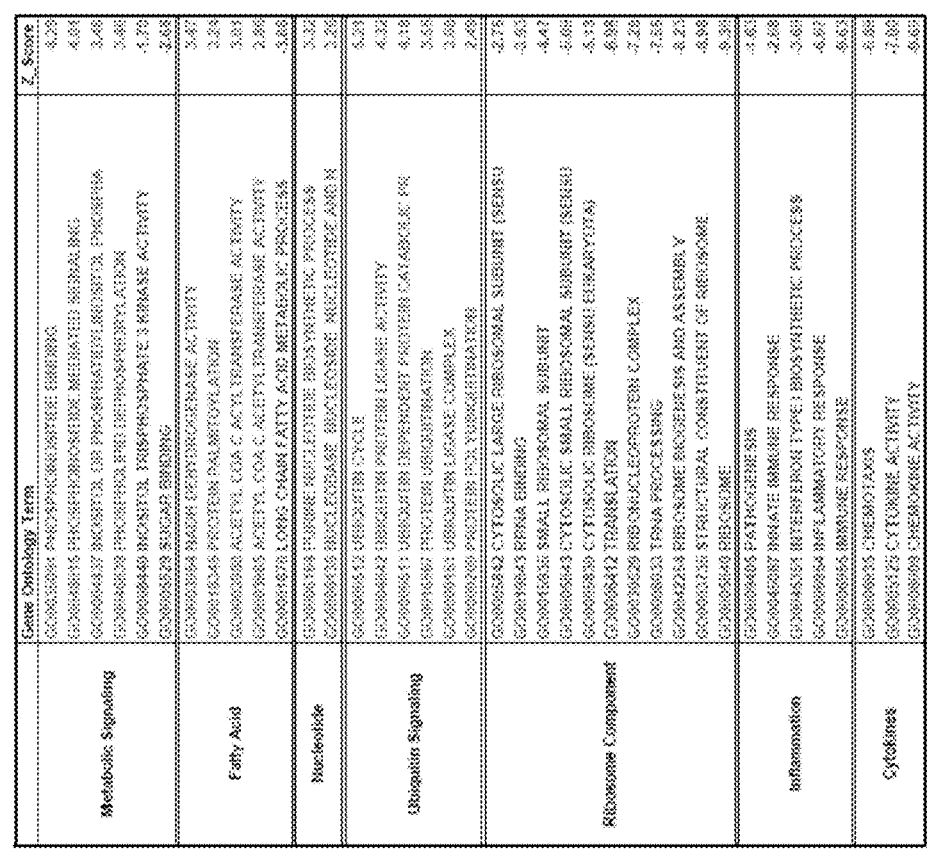

To unravel the biological role of MOTS-c, microarray analysis on HEK293 cells following 4- and 72-hours of MOTS-c (10 μM) treatment was performed. Principal component analysis (PCA) showed that MOTS-c promoted a clear global gene expression profile shift by 72 hours (FIG. 14a). To further highlight differences between functional pathways modified by MOTS-c, parametric analysis of gene set enrichment (PAGE) to show that gene expression significantly altered by 4 hours after MOTS-c treatment, which became remarkably distinct by 72 hours was employed (FIG. 14b). There was modest overlap between gene signatures at 4- and 72-hours, suggesting a time-dependent progression in response to MOTS-c treatment (FIG. 14c). It was found that MOTS-c had a profound effect on gene expression in pathways involved in cellular metabolism and inflammation (FIG. 14d; FIG. 30).

Figure 14E:
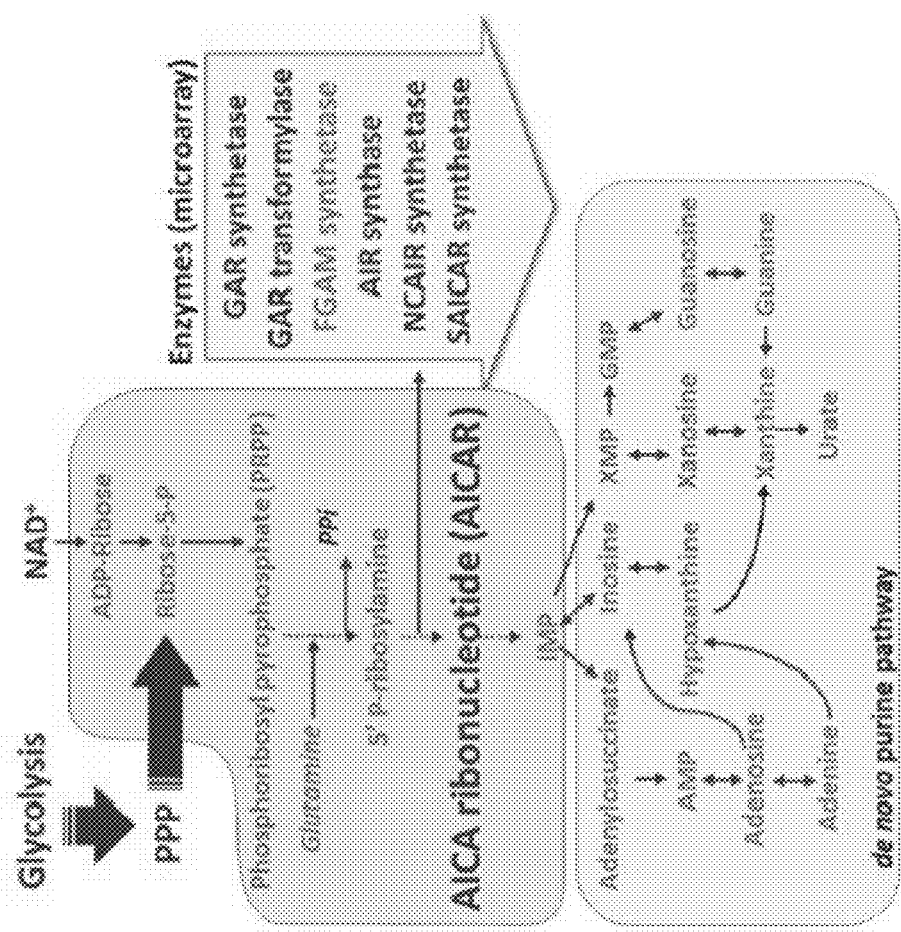
Figures 14F, 14G:
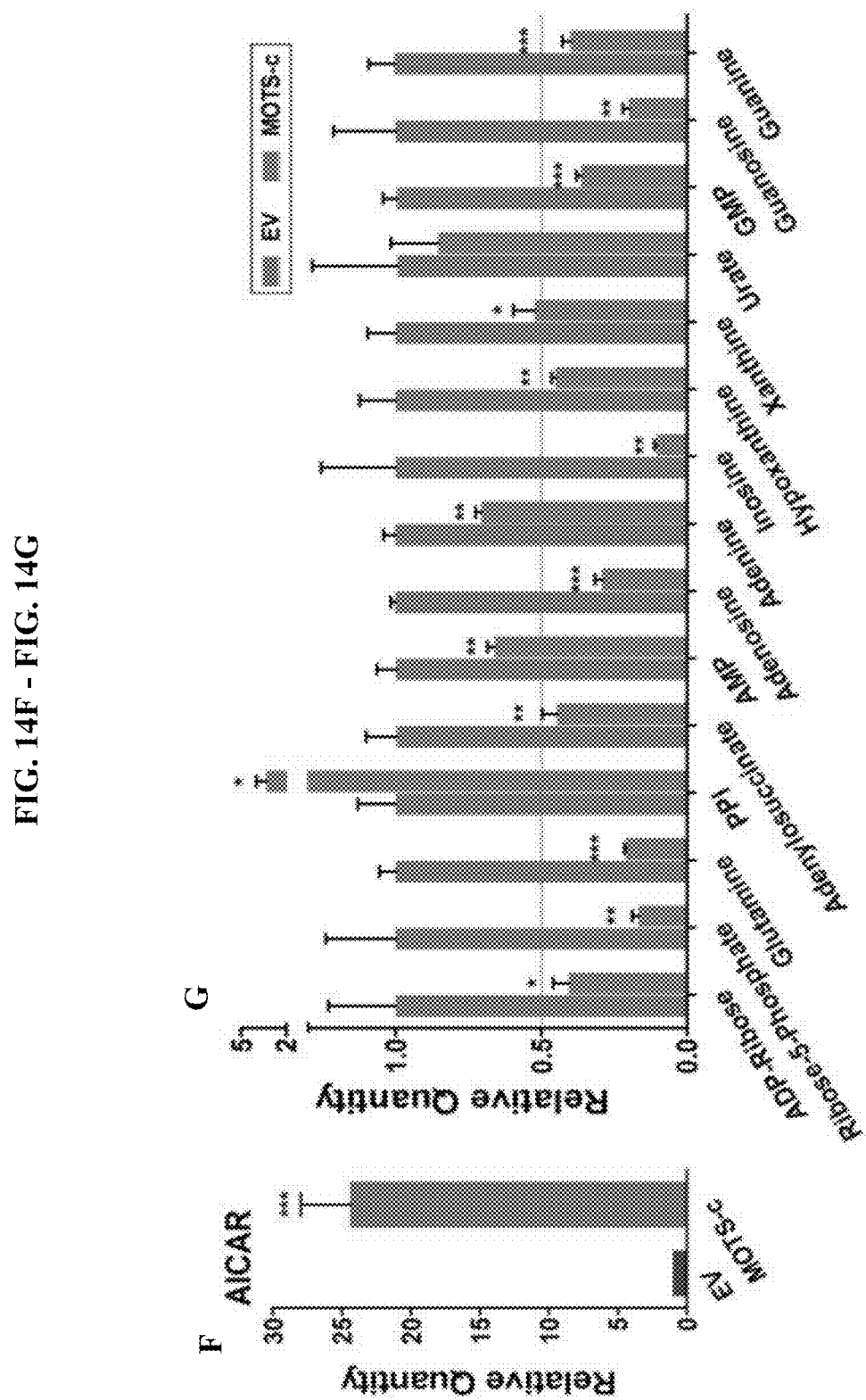
Figures 18A, 18B:
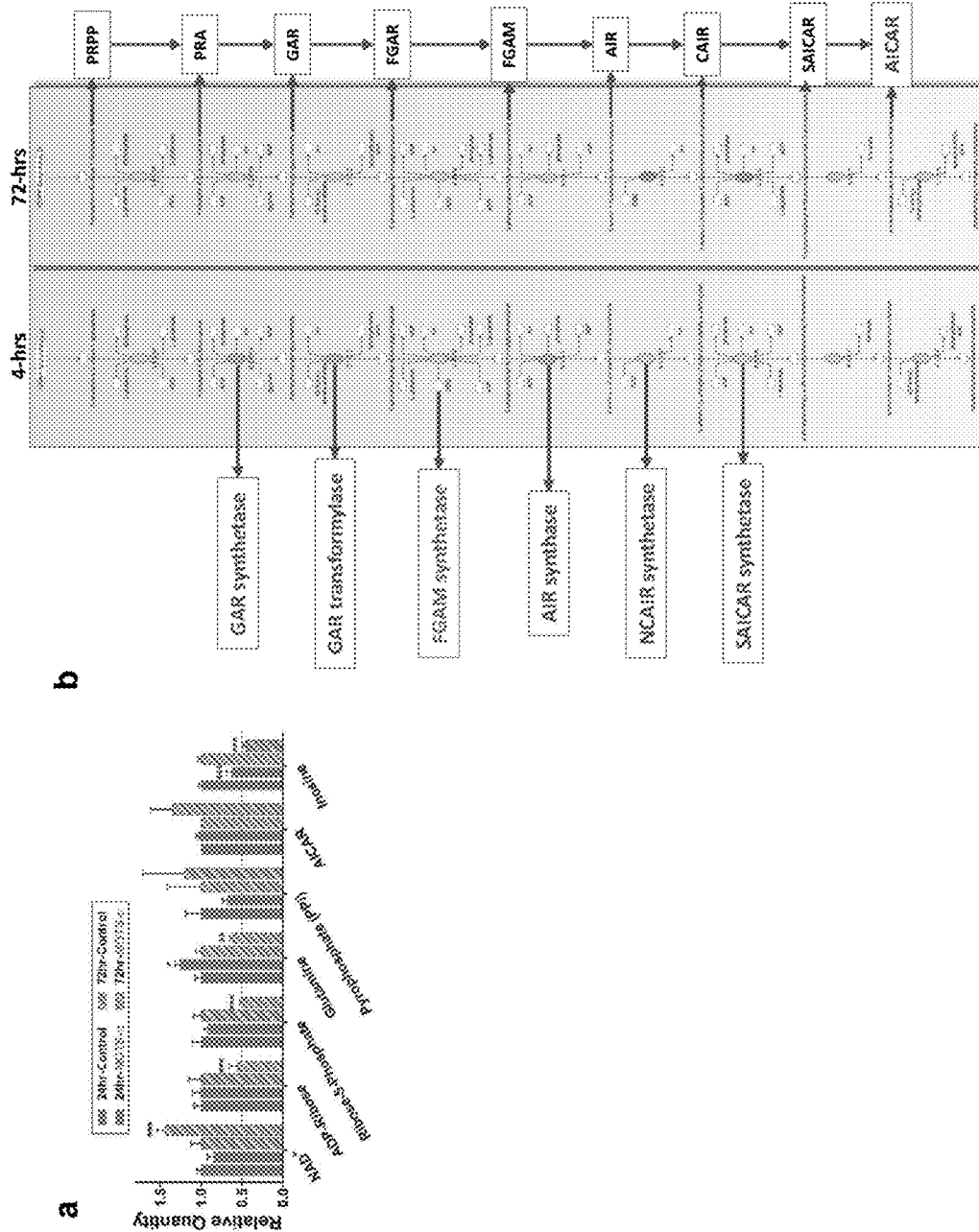
FIG. 18A-FIG. 18B describes the effect of MOTS-c on the de novo purine biosynthesis pathway (N=5). a, MOTS-c treatment (10 μM; 24- and 72-hours post-treatment) regulates the de novo purine biosynthesis pathway in HEK293 cells. b, MOTS-c treatment (10 μM) alters gene expression of pathways involved in de novo purine biosynthesis as determined by microarray and Ingenuity Pathway Analysis (IPA) (N=6). See FIG. 14e for overlay with metabolomics analysis. Red: upregulation, green: downregulation. Student's t-test between groups within the same time point. *P<0.05, P<0.01, *P<0.001
Figures 19A, 19B:
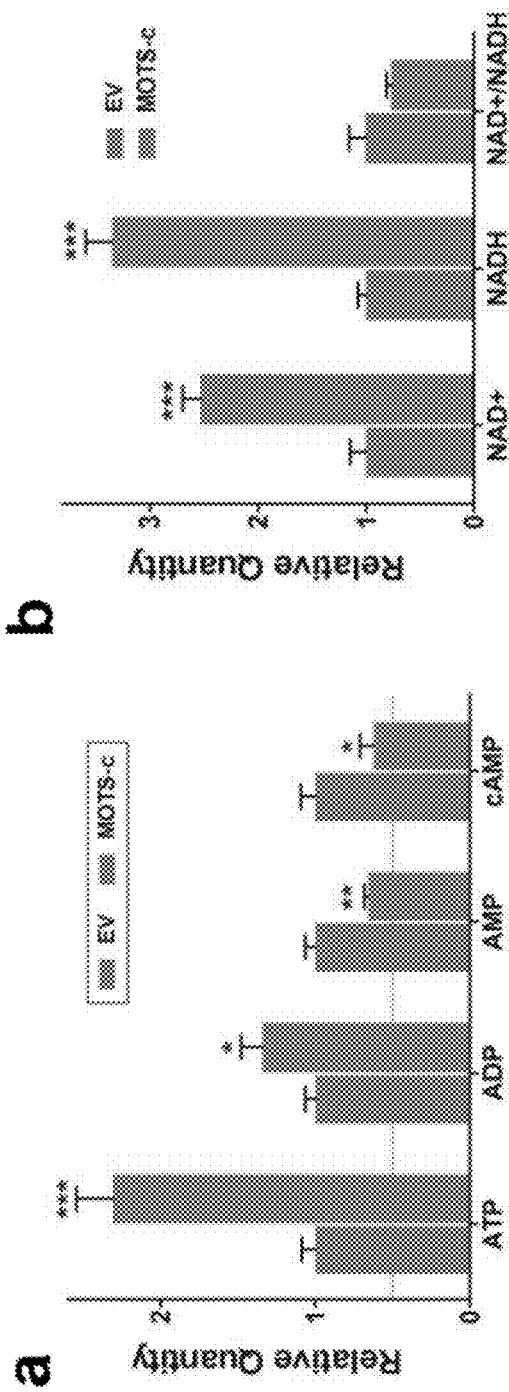
FIG. 19A-FIG. 19B describes the effect of MOTS-c on adenylic system components and nicotinamide adenine dinucleotide (NAD) cycle components. a, ATP, ADP, AMP, and cyclic AMP (cAMP) levels, and b, $NAD^+$ and NADH levels in HEK293 cells stably over-expressing MOTS-c. EV: HEK293 stably transfected with empty vector. Student's t-test. *P<0.05, P<0.01, *P<0.001
Figure 20A:
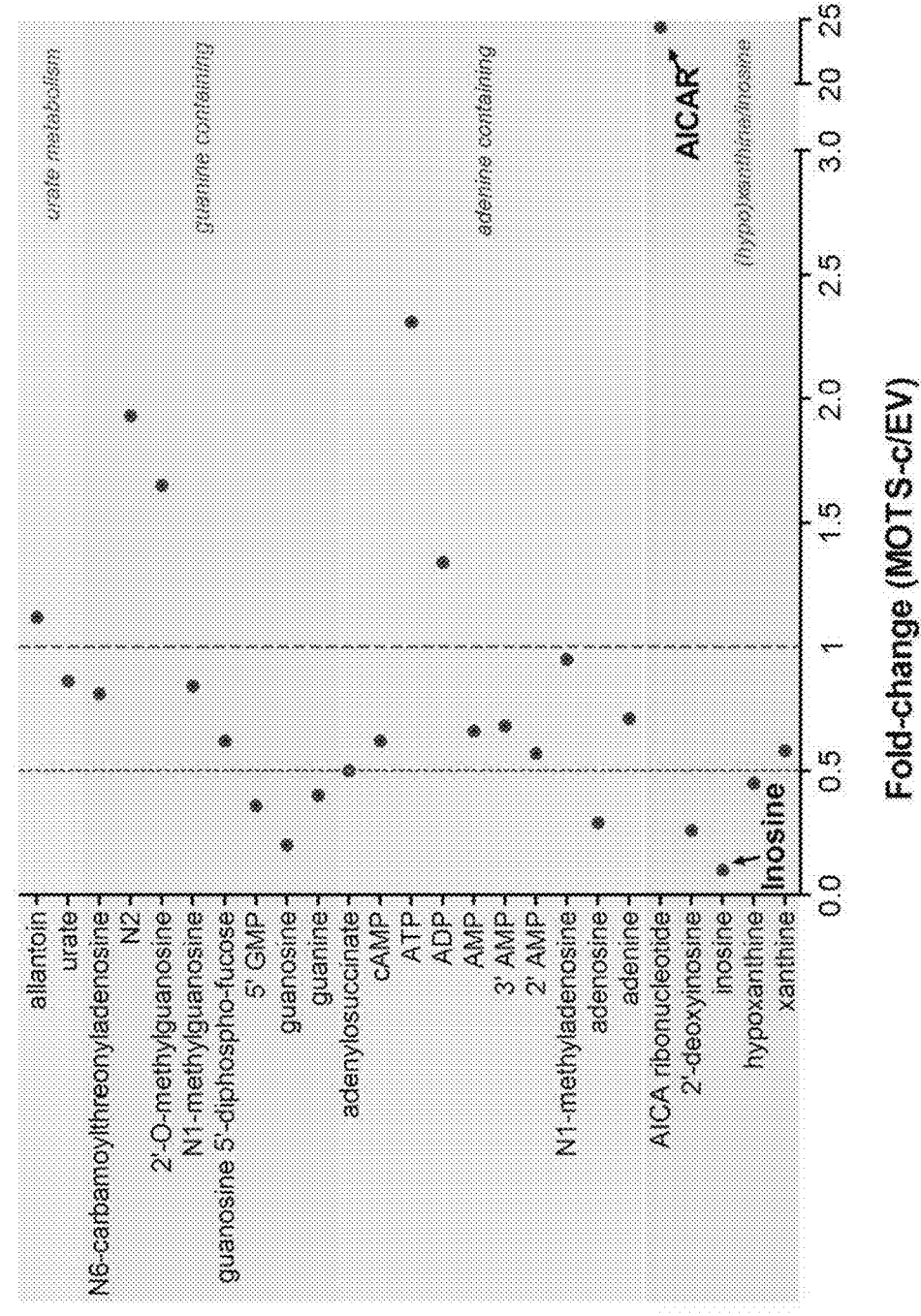
FIG. 20A-FIG. 20B describes the effect of MOTS-c on the components of a, purine metabolism and b, cofactors and vitamin metabolism in HEK293 cells stably over-expressing MOTS-c, determined by metabolomics (N=5). EV: HEK293 stably transfected with empty vector.
Figure 20B:
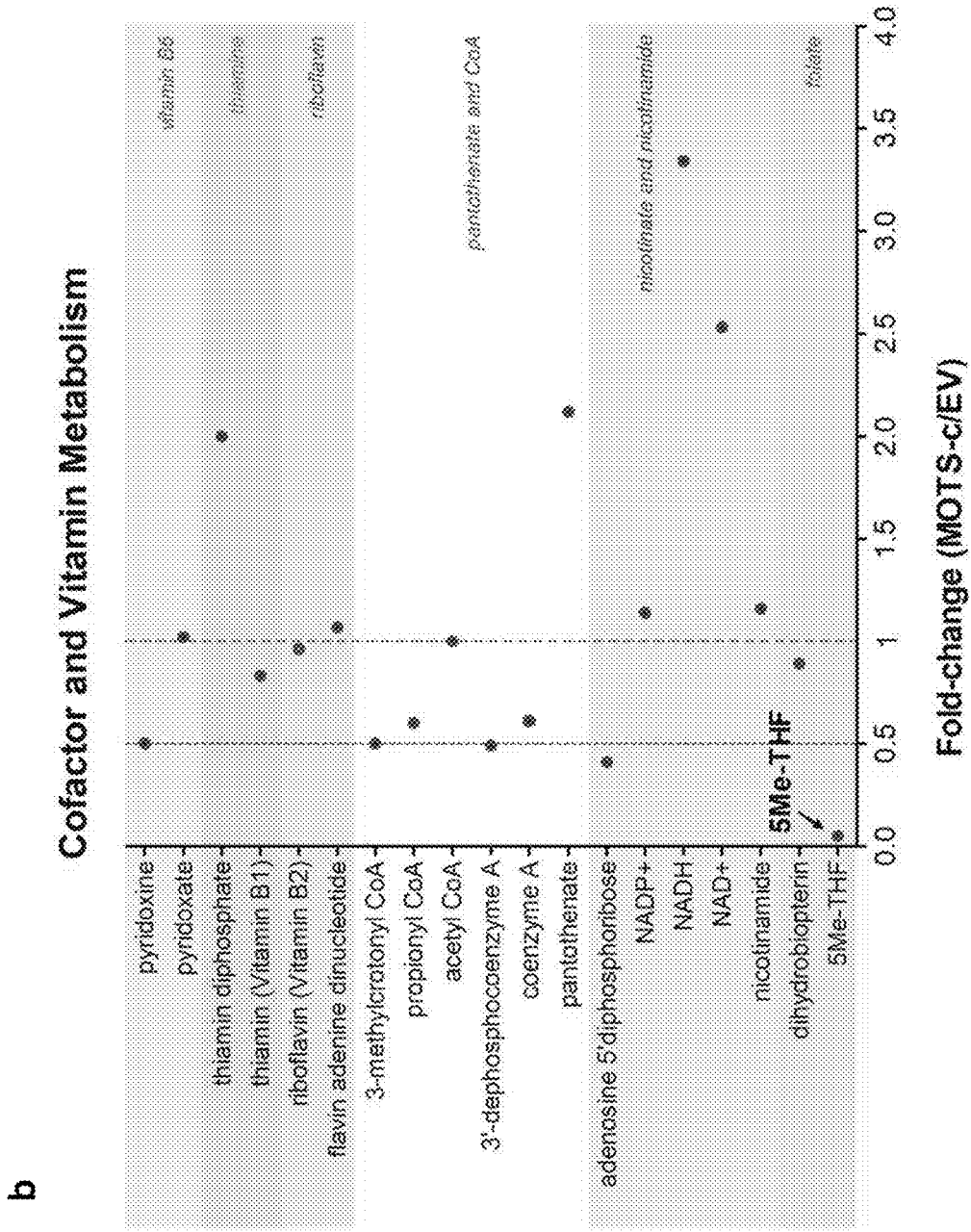

Next, the effect of MOTS-c on global metabolism was studied using unbiased metabolomic profiling in HEK293 cells either stably transfected with MOTS-c or empty expression clones (MOTS-c-ST and MOTS-c-EV cells, respectively) or exogenously treated with synthetic MOTS-c (10 uM) for 24- and 72-hours. Of the 356 named metabolites, 194 were found to be significantly altered in MOTS-c-ST cells and 49 and 177 were significantly altered by 24- and 72-hours, respectively (FIG. 31). Interestingly, the de novo purine biosynthetic pathway was found to be significantly altered (FIG. 14e, FIG. 20a), including a >20-fold increase in endogenous AICAR (5-aminoimidazole-4-carboxamide ribonucleotide) concentration 72-hours of exogenous MOTS-c treatment (FIG. 18a). Consistent with the metabolomics findings, microarray analysis also showed that MOTS-c altered purine de novo biosynthesis by as early as 4 hours post-treatment (FIG. 18b). Purines are synthesized from ribose-5-phosphate (R5P) produced from the pentose phosphate pathway (PPP), and also by ADP-ribose derived from $NAD^+$ (FIG. 14e). Accelerated glycolysis/PPP and increased levels of $NAD^+$ (FIGS. 18a, 19b), but reduced levels of ADP-ribose and R5P in MOTS-c treated cells was found. These data are further supported by reduced glutamine and increased pyrophosphate (PPi) levels (FIG. 14g), which indicate that MOTC-s stimulated increased flux of these pathways in HEK293 cells. The build-up at AICAR consequently blocked and reduced downstream intermediates such as inosine, adenylosuccinate, AMP, and also the purine end-products, including adenine, guanine, and xanthine (FIGS. 14g, 18 and 20a). MOTS-c may promote a build-up at AICAR by altering folate metabolism. A significant reduction of 5-methyl-tetrahydrofolate (5Me-THF) was observed (FIG. 20b), which is required to catalyze the formylation of AICAR to its downstream intermediate F-AICAR. Indeed previous reports show that inhibiting folate metabolism by methotrexate increases intracellular AICAR levels (E. S. Chan, B. N. Cronstein, *Methotrexate—how does it really work? Nature reviews. Rheumatology* 6, 175 (March, 2010)). Impaired folate metabolism, especially 5Me-THF, has also been implicated as a mechanism underlying the activation of AMPK by the anti-diabetic drug metformin (B. Corominas-Faja et al., Metabolomic fingerprint reveals that metformin impairs one-carbon metabolism in a manner similar to the antifolate class of chemotherapy drugs. *Aging* 4, 480 (July, 2012)).

Figure 14H:
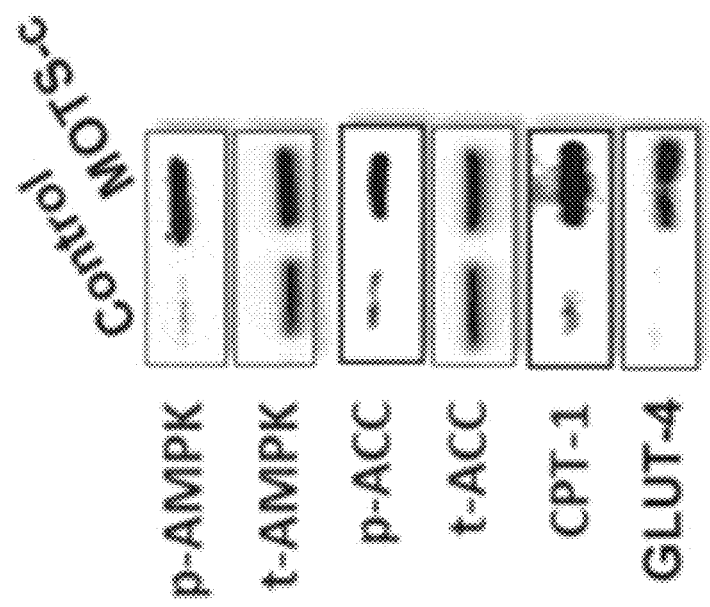
Figure 14I:
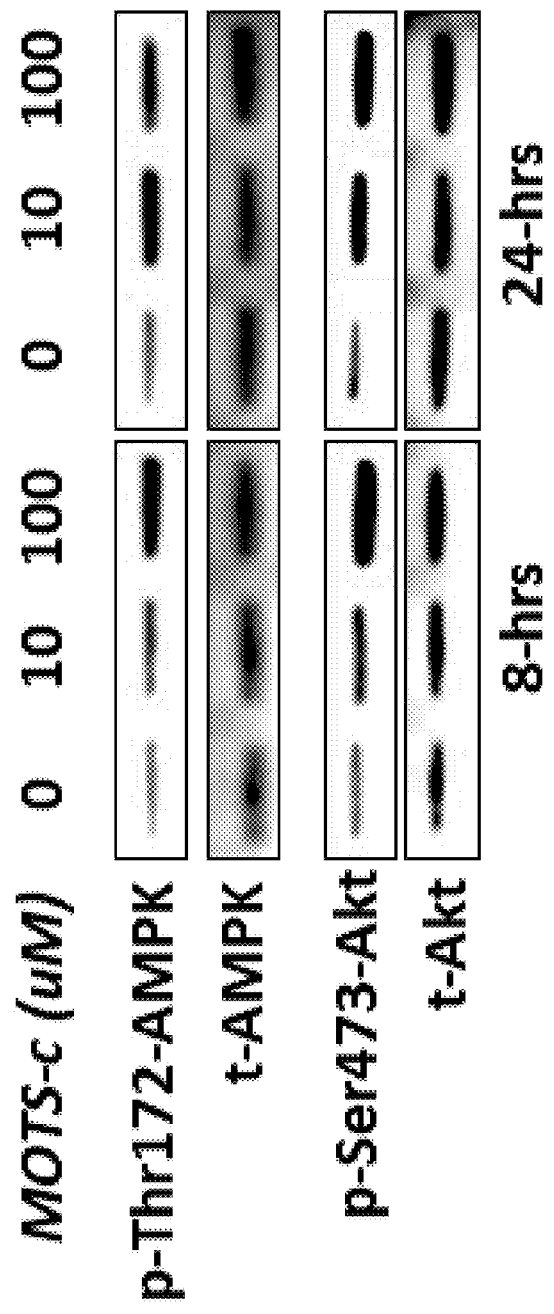

AICAR is a potent activator of the master energy regulator AMPK, shown to stimulate fatty acid oxidation via phosphorylation-induced inactivation of acetyl-CoA carboxylase (ACC) alleviating allosteric inhibition of carnitine palmitoyltransferase 1 (CPT-1), the central transport mechanism of fatty acids into mitochondria for β-oxidation. (G. Hasko, B. Cronstein, Regulation of inflammation by adenosine. *Frontiers in immunology* 4, 85 (2013)). AICAR-induced AMPK activation enhances glucose uptake in muscle, in part, by increasing GLUT4 transcription comparable to that achieved by exercise (G. R. Steinberg, B. E. Kemp, *AMPK in Health and Disease. Physiological reviews* 89, 1025 (July, 2009)). 72-hours of MOTS-c treatment (10 μM) led to the phosphorylation of AMPKα (Thr172) and ACC (Ser79), and also increased CPT-1 and GLUT4 protein levels (FIG. 14h) in a time and dose-dependent manner (FIG. 14i). Furthermore, it was found that MOTS-c promotes the phosphorylation of Akt at Ser-473 (FIG. 14*i*). Notably AMPK activation was observed under low AMP levels and high ADP and ATP levels (FIGS. 19*a*, 20*a*). Increased ATP may be attributed to enhanced glycolysis, which is a rapid but inefficient method of ATP production (P. S. Ward, C. B. Thompson, *Metabolic reprogramming: a cancer hallmark even warburg did not anticipate. Cancer cell* 21, 297 (Mar. 20, 2012)). These findings suggest that MOTS-c promotes AMP-independent activation of AMPK, similar to that achieved by salicylate (K. Hashiguchi, Q. M. Zhang-Akiyama, *Establishment of human cell lines lacking mitochondrial DNA. Methods in molecular biology* 554, 383 (2009)), leptin (T. Ohta et al., *Untargeted metabolomic profiling as an evaluative tool of fenofibrate-induced toxicology in Fischer* 344 *male rats. Toxicologic pathology* 37, 521 (June, 2009)), and metformin (N. Fujii, N. Jessen, L. J. Goodyear, *AMP-activated protein kinase and the regulation of glucose transport. American journal of physiology. Endocrinology and metabolism* 291, E867 (November, 2006)).

Figures 15A, 15B:
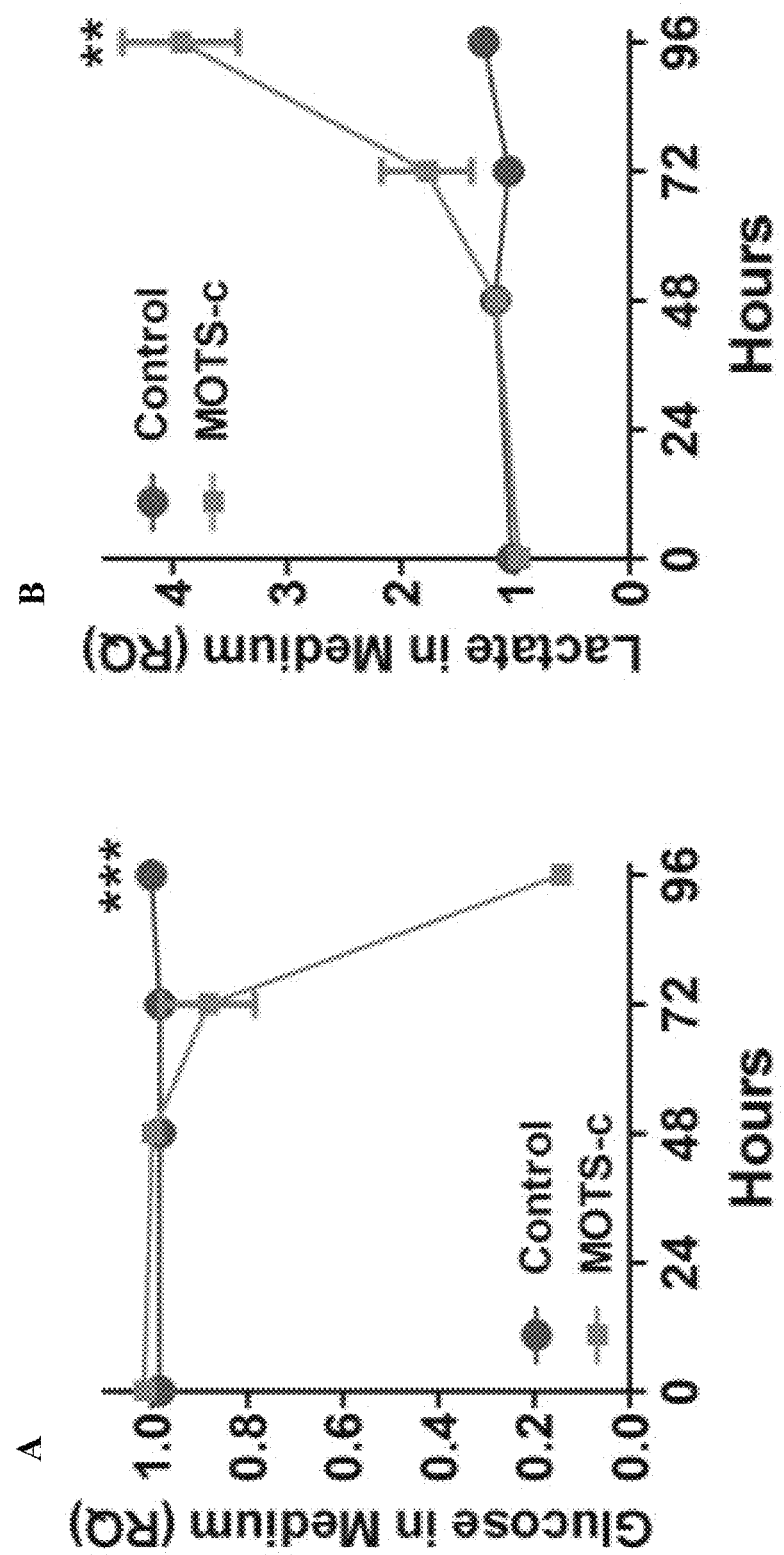
FIG. 15A-FIG. 15K describes MOTS-c coordinates cellular glucose, mitochondrial, and fatty acid metabolism. Measurements of: a, glucose and b, lactate in the cell culture medium after MOTS-c treatment (10 μM; N=6). c, MOTS-c-dependent glycolytic intermediate changes detected by metabolomics. d, Real-time glycolytic flux was determined by extracellular acidification rate (ECAR) (N=6). Glycolysis, glycolytic capacity, and glycolytic reserve were estimated by challenging cells with glucose, oligomycin, and 2-deoxyglucose, respectively. e-f, real-time oxygen consumption rate (OCR) was measured after MOTS-c treatment (N=6). e, ATP turnover, and maximum respiratory capacity was estimated by challenging cells with oligomycin and FCCP and f, spare respiratory capacity, proton leakage, and coupling efficiency was calculated. g, TCA intermediates after MOTS-c treatment determined by metabolomics are shown (N=5). h, Cell number was counted after MOTS-c treatment under glucose or galactose medium. Galactose forces mammalian cells to rely on mitochondrial metabolism (N=6). MOTS-c induced changes in intracellular i, acylcarnitine shuttles, j, essential fatty acids, and k, the β-oxidation intermediate myristoyl CoA determined by metabolomics (N=5). Data shown as mean±SEM. Student's t-test. *P<0.05, P<0.01, *P<0.001.
Figure 15C:
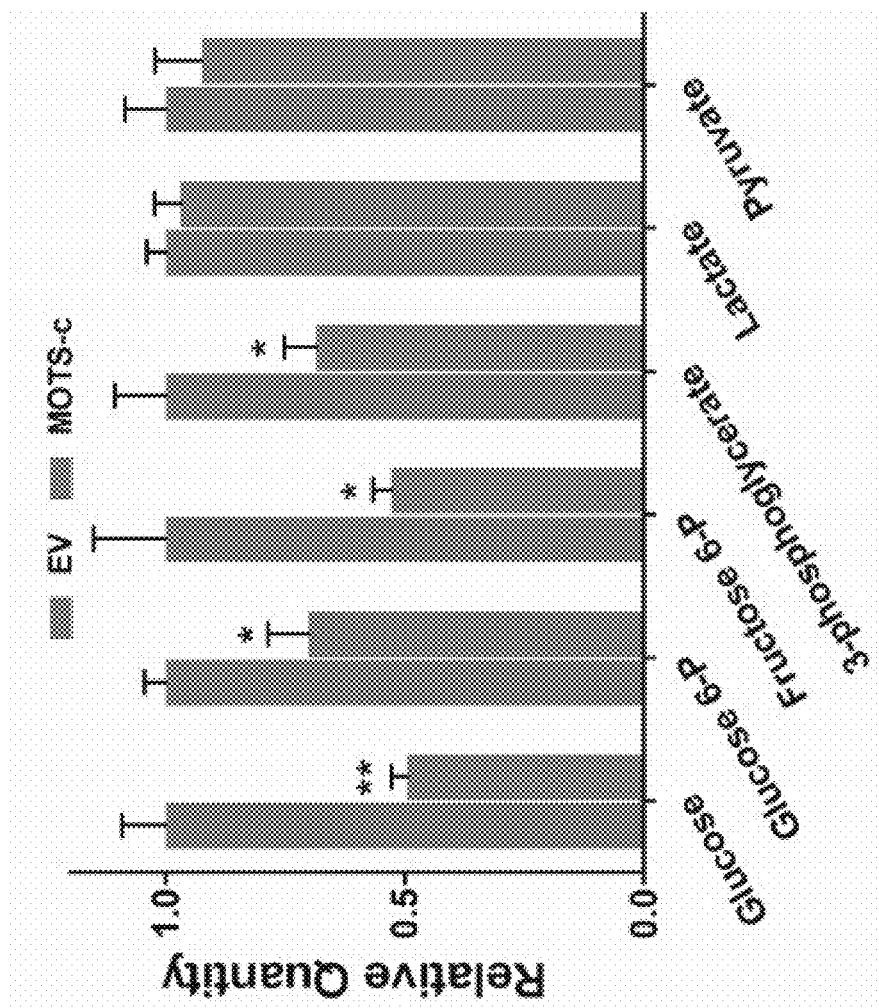
Figure 15D:
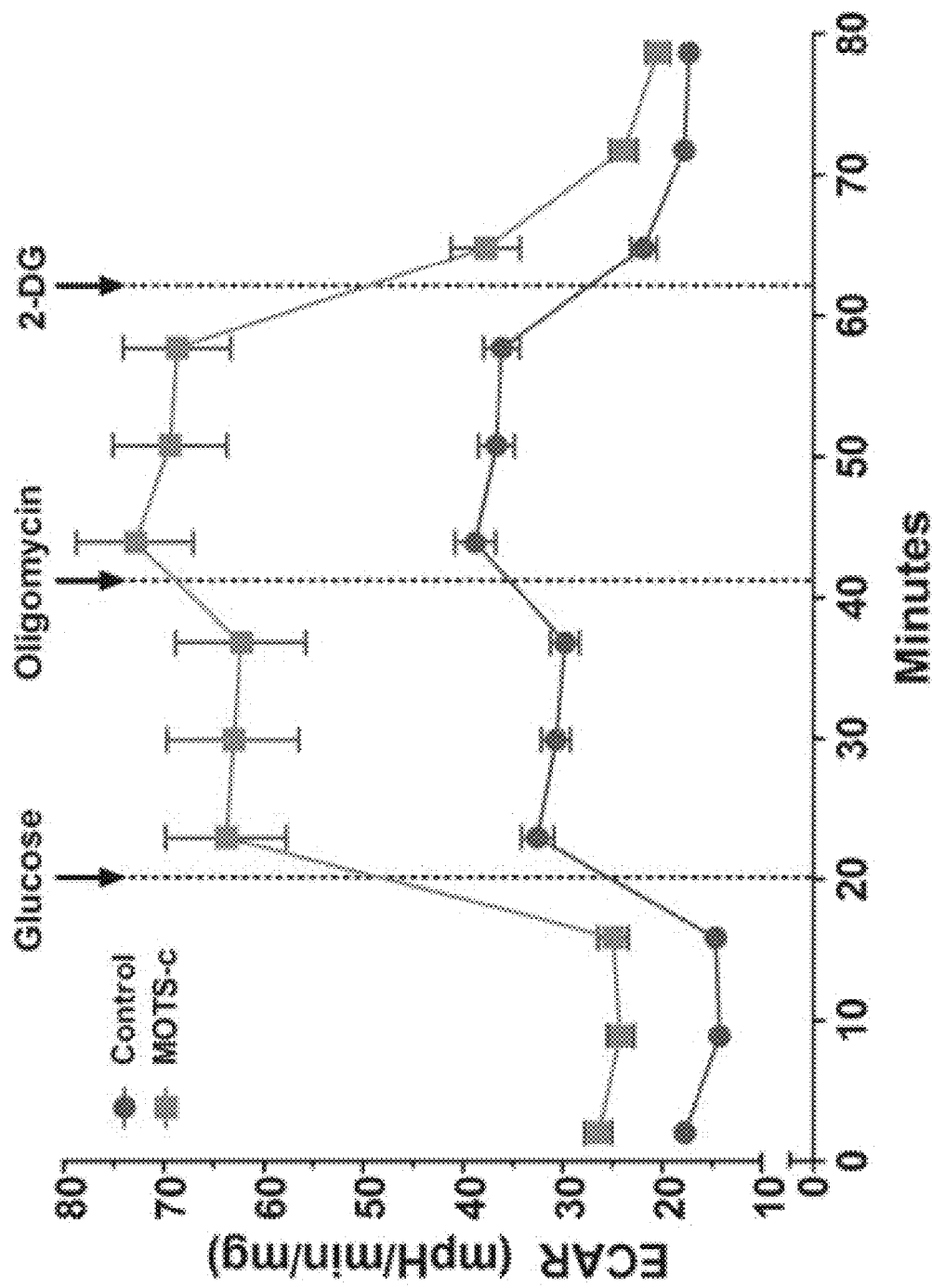
Figures 21A, 21B:
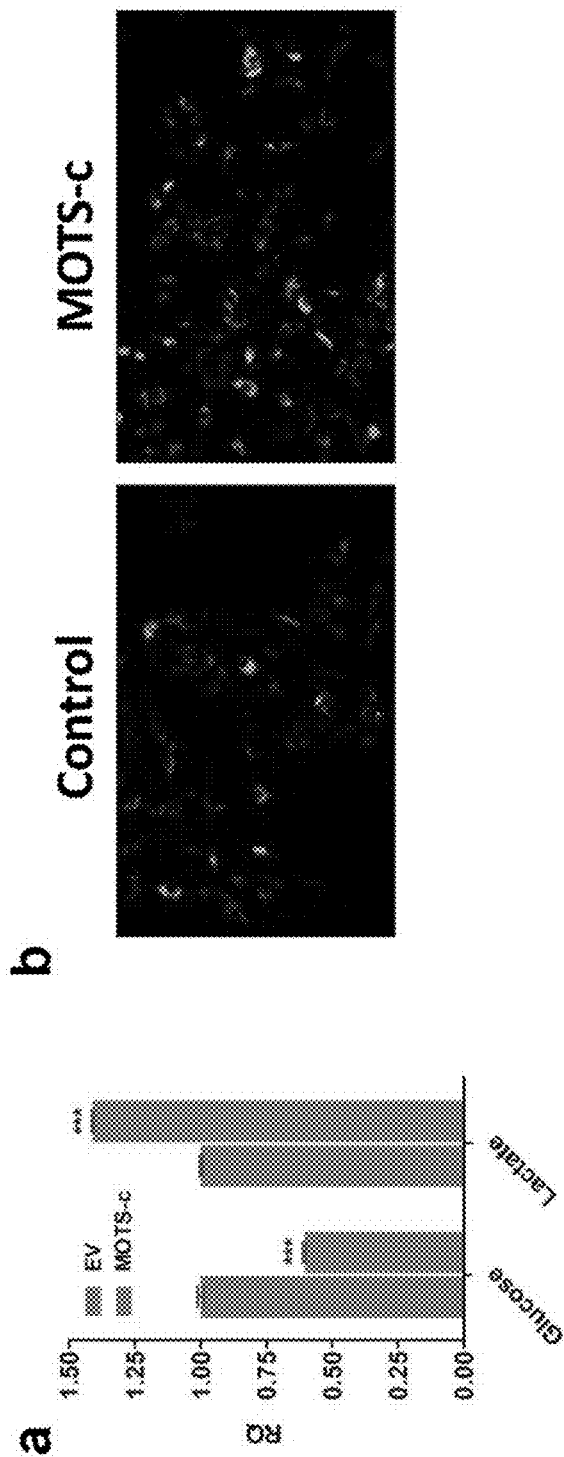
FIG. 21A-FIG. 21B describes the effect of MOTS-c on a, extra-cellular (culture medium) levels of glucose and lactate in HEK293 cells stably over-expressing MOTS-c (N=6), and b, intracellular glucose uptake rate, determined by the fluorescent glucose analog 2-NBDG, in HEK293 cells treated with MOTS-c (10 μM; 72-hours) (N=3). Student's t-test. ***P<0.001
Figure 22:
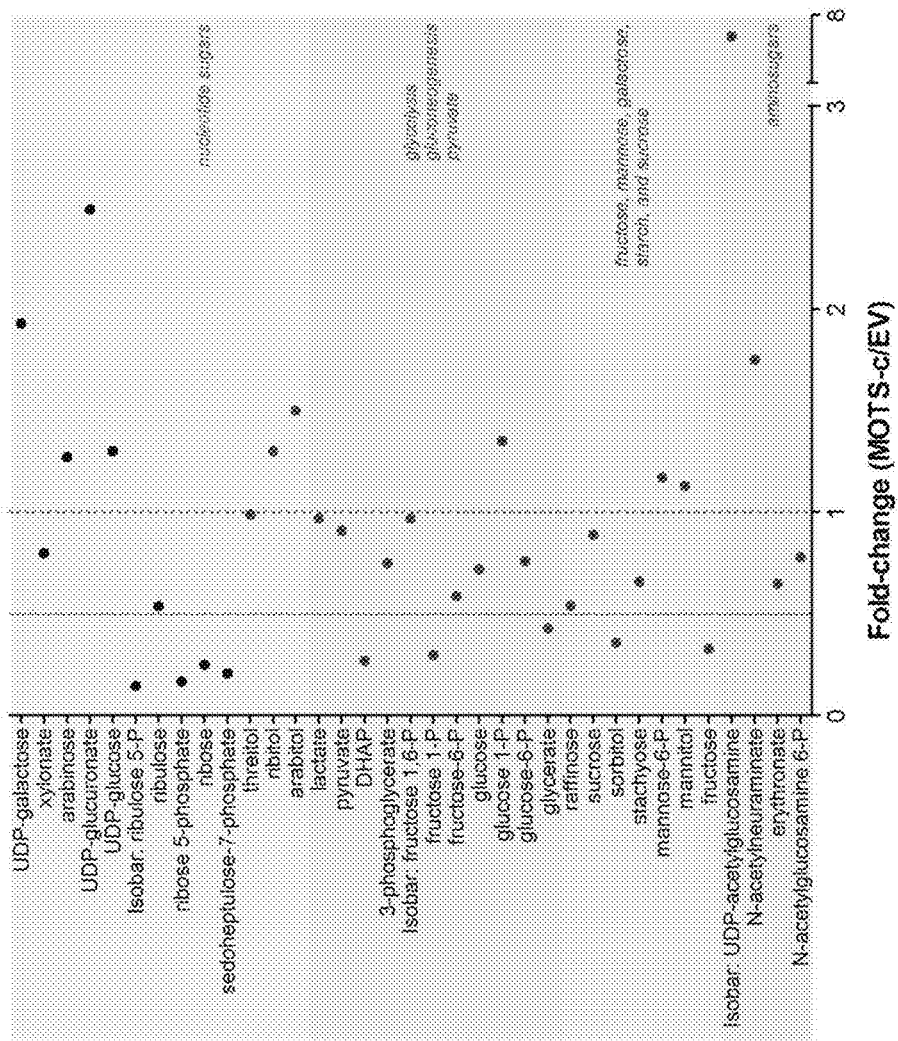
FIG. 22 describes the effect of MOTS-c on the metabolism of various sugar substrates in HEK293 cells stably over-expressing MOTS-c, determined by metabolomics (N=5). EV: HEK293 stably transfected with empty vector FIG. 23A-FIG. 23C describes intermediate metabolites, determined by metabolomics (N=5), of a, glycolysis and b, the pentose phosphate pathway (PPP) following 24- or 72-hours of exogenous MOTS-c (10 µM) treatment in HEK293 cells, and c, PPP in HEK293 cells stably over-expressing MOTS-c. EV: HEK293 stably transfected with empty vector. Student's t-test between groups within the same time point. *P<0.05, P<0.01, *P<0.001
Figures 23A, 23B, 23C:
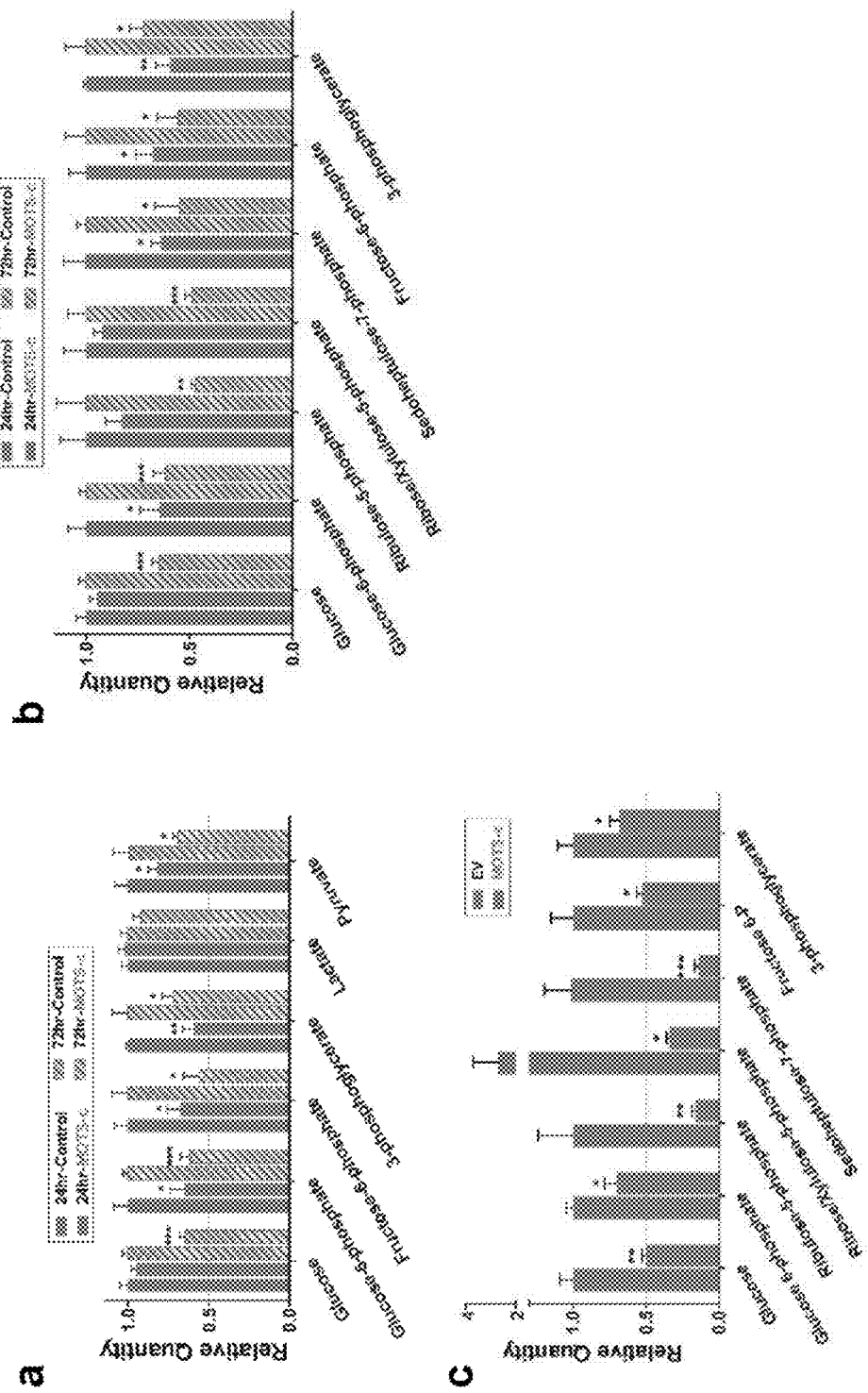

Next, the effect of MOTS-c on cellular metabolism focusing on glucose and fatty acid metabolism and cellular respiration was investigated. It was found that MOTS-c stimulated glycolysis reflected by increased glucose uptake (FIG. 15*a*; FIG. 21*a*, *b*) and lactate production (FIG. 15*b*; FIG. 21*a*). Additionally, intracellular glucose levels were decreased, along with other glycolytic intermediates (FIG. 15*c*; FIG. 22), further supporting increased glycolytic flux. MOTS-c also altered the utilization of other sugar substrates (FIG. 22). To directly test the rate of glycolysis in real-time, extracellular acidification rate (ECAR) was measured. MOTS-c-ST cells had a higher rate of basal glycolysis and showed improved glycolytic response when stimulated with glucose (FIG. 15*d*). Also, total glycolytic capacity, estimated by oligomycin treatment, was higher in these cells (FIG. 15*d*). Intracellular lactate levels were identical between MOTS-c-ST and MOTS-c-EV cells (FIG. 15*c*), as excess production by MOTS-c-ST cells was released into the medium (FIG. 15*b*; FIG. 21*a*). Consistent with observations in MOTS-c-ST cells, mass spectrometry analysis provided further evidence of increased glycolysis in HEK293 cells within 24 hours of MOTS-c treatment (FIG. 23*a*). The pentose phosphate pathway (PPP), an alternative branch of glycolysis, provides R5P for de novo purine biosynthesis. Reduced levels of PPP intermediates, including R5P, were observed in MOTS-c-ST cells and also MOTS-c-EV cells after 72-hours of exogenous MOTS-c treatment (10 μM) (FIG. 23*b*, *c*).

Figures 15E, 15F:
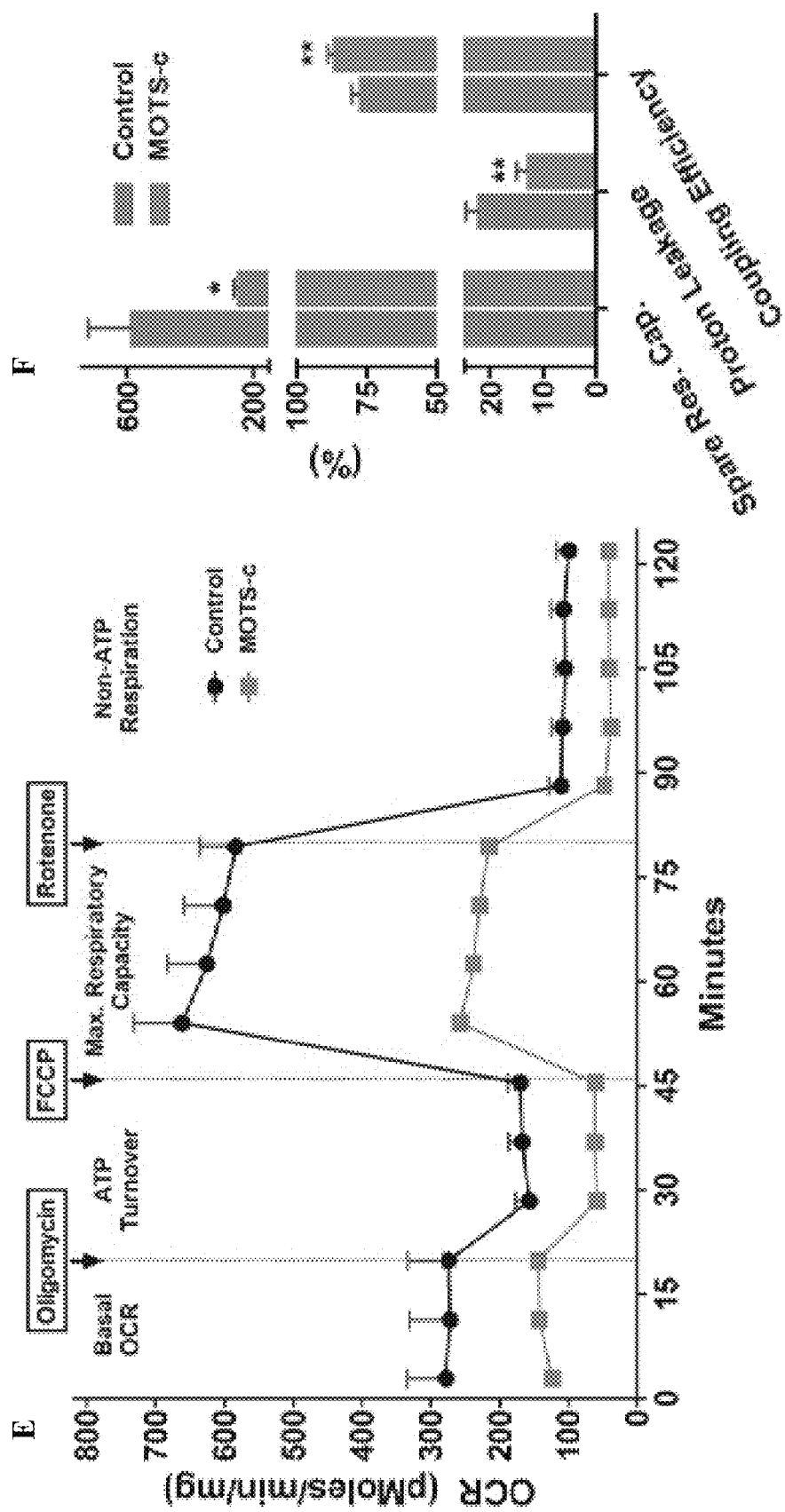
Figure 15G:
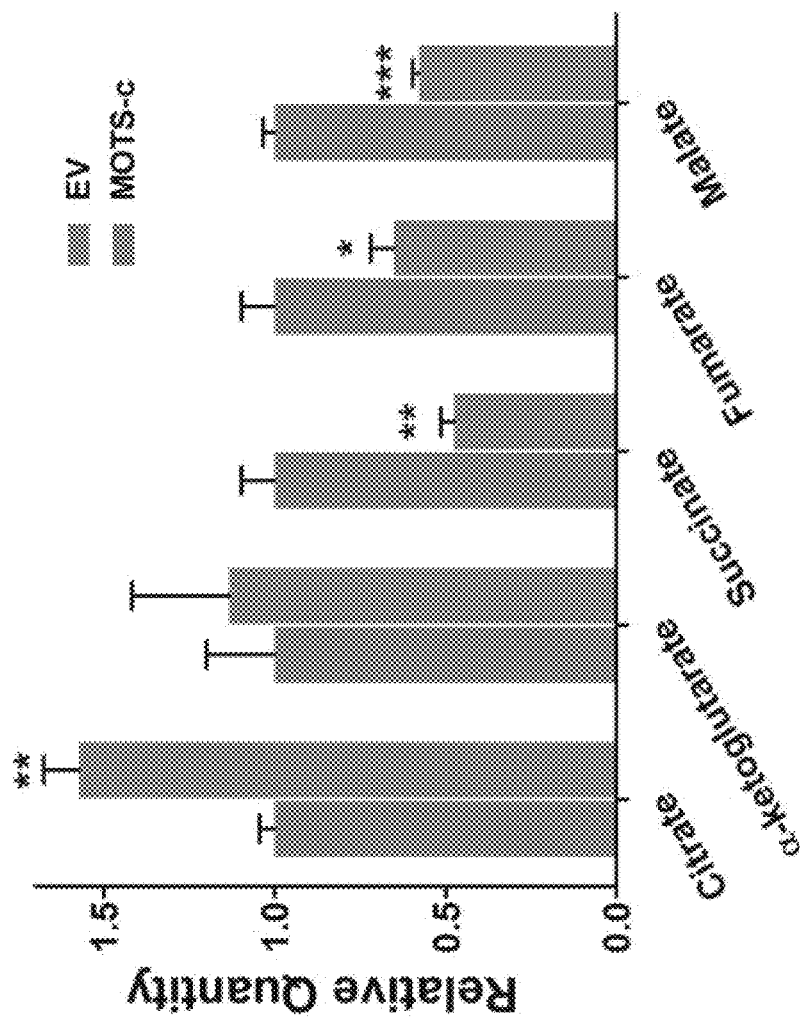
Figure 15H:
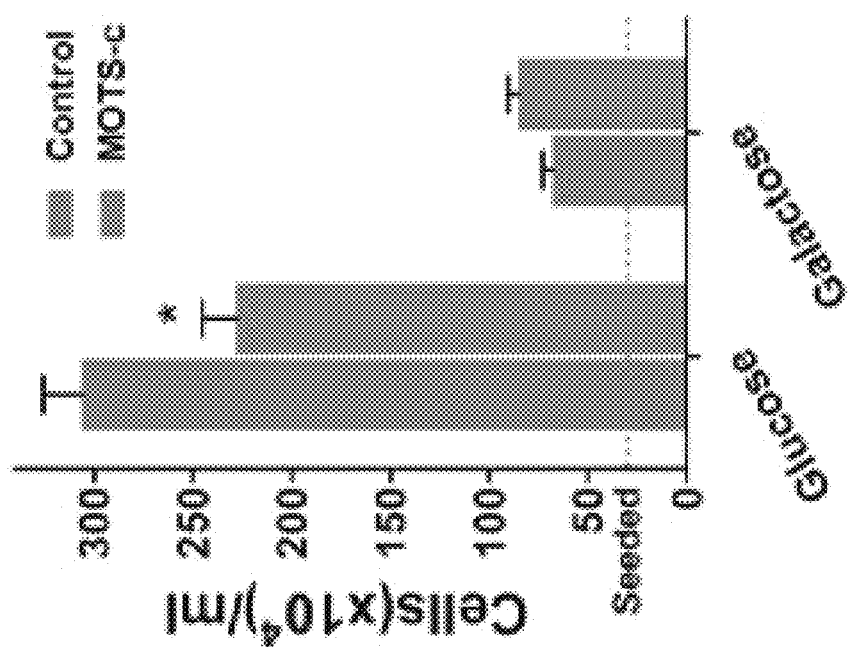
Figure 24:
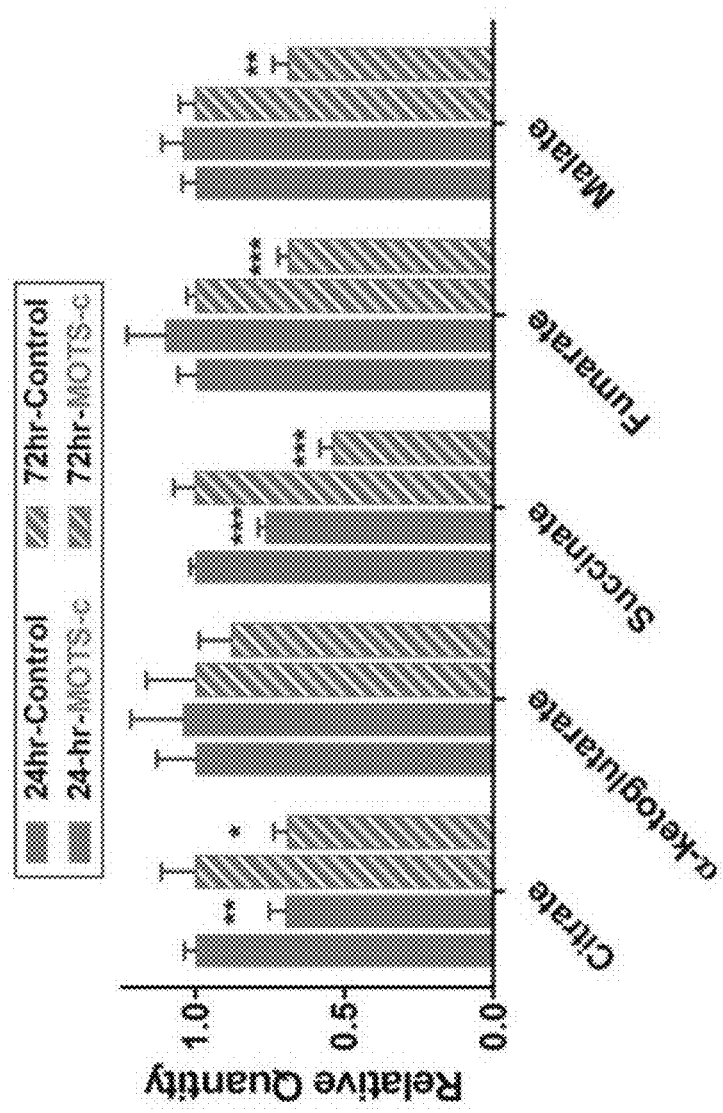
FIG. 24 describes the effect of exogenous MOTS-c treatment (10 µM; 24- or 72-hours) on the levels of the tricarboxylic acid (TCA) cycle intermediates in HEK293 cells, determined by metabolomics (N=5). Student's t-test between groups within the same time point. *P<0.05, P<0.01, *P<0.001
Figure 25:
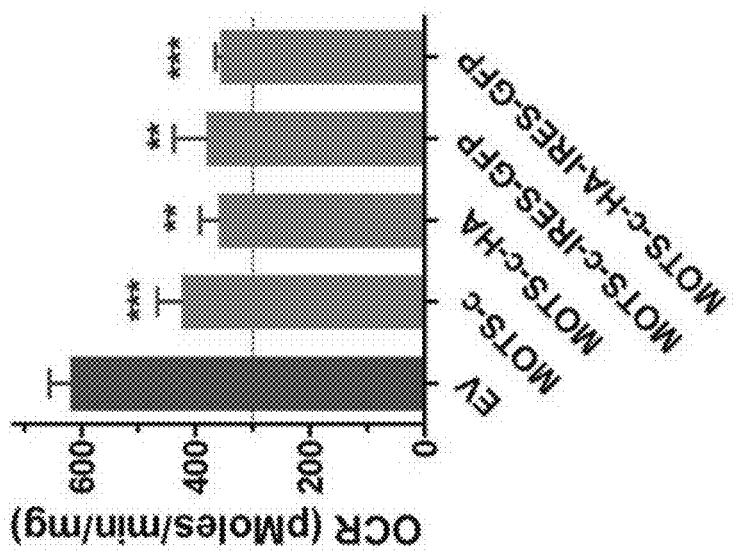
FIG. 25 describes the effect of various MOTS-c expression clones on oxygen consumption rate (OCR) in HEK293 cells (N=12). MOTS-c-HA: MOTS-c tagged with HA at the N-terminus; MOTS-c-IRES-GFP: MOTS-c cloned into an expression vector that independently expresses GFP via the internal ribosome entry site (IRES); MOTS-c-HA-IRES-GFP: MOTS-c-HA cloned into an expression vector with IRES-GFP. Student's t-test. *P<0.05, P<0.01, *P<0.001
Figures 26A, 26B:
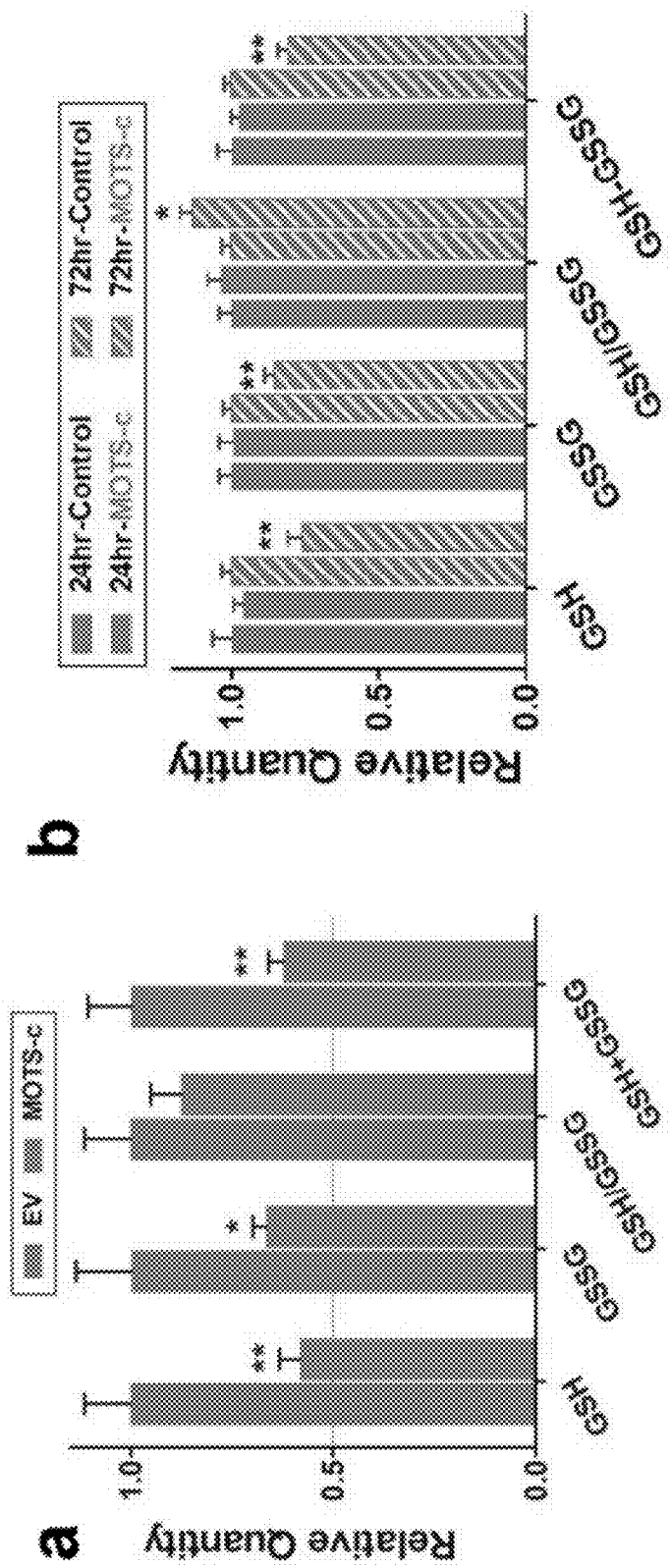
FIG. 26A-FIG. 26B describes the cellular redox homeostasis was determined by the state of the glutathione system. Glutathione in its reduced (GSH) and oxidized (GSSG) form, their ratio (GSH/GSSG), and total glutathione levels (GSH+GSSG) were determined in a, HEK293 cells stably over-expressing MOTS-c and b, HEK293 cells treated with exogenous MOTS-c (10 µM) for 24- or 72-hours (N=5), EV: HEK293 stably transfected with empty vector. Student's t-test. *P<0.05, **P<0.01

Next, mitochondrial respiration was measured because glycolytic end-products are shuttled into the mitochondria for further energy extraction through oxidative phosphorylation. In line with increased glycolysis, MOTS-c treatment reduced basal oxygen consumption rate (OCR) as well as maximum respiratory capacity in HEK293 cells (FIG. 15*e*). This is consistent with the "Crabtree effect", a phenomenon whereby rapidly dividing cells including: cancer cells, lymphocytes, stem cells, and spermatozoa, exhibit suppressed respiration in response to high glucose concentrations (K. H. Ibsen, *The Crabtree effect: a review. Cancer research* 21, 829 (August, 1961); T. Wang, C. Marquardt, J. Foker, Aerobic glycolysis during lymphocyte proliferation. *Nature* 261, 702 (Jun. 24, 1976); and V. Gogvadze, S. Orrenius, B. Zhivotovsky, *Mitochondria in cancer cells: what is so special about them? Trends in cell biology* 18, 165 (April, 2008)). Decreased electron transport chain activity was also indicated by reduced proton leakage (M. Jastroch, A. S. Divakaruni, S. Mookerjee, J. R. Treberg, M. D. Brand, *Mitochondrial proton and electron leaks*. Essays in biochemistry 47, 53 (2010)) (FIG. 15*f*). Reduced oxidative capacity was associated with depletion of TCA cycle intermediates in MOTS-c-ST cells and in HEK293 cells treated with exogenous MOTS-c (FIG. 15*g*; FIG. 24). Transient transfection of MOTS-c expression clones in HEK293 cells also decreased OCR (FIG. 25). Despite reduced mitochondrial metabolism, MOTS-c did not perturb cellular redox homeostasis as determined by the ratio of reduced to oxidized glutathione (GSH/GSSG), however total glutathione levels were decreased in MOTS-c-ST cells and in HEK293 cells 72-hours after MOTS-c treatment (FIG. 26). To test whether MOTS-c suppresses mitochondrial respiration by increasing glycolytic flux or by targeting mitochondrial metabolism per se, HEK293 cells were cultured in medium with either glucose or galactose as the main carbon source. In mammalian cells, galactose is largely metabolized by the mitochondria, shifting reliance on oxidative phosphorylation for energy production (L. D. Marroquin, J. Hynes, J. A. Dykens, J. D. Jamieson, Y. Will, *Circumventing the Crabtree effect: replacing media glucose with galactose increases susceptibility of HepG2 cells to mitochondrial toxicants. Toxicological sciences: an official journal of the Society of Toxicology* 97, 539 (June, 2007)). MOTS-c reduced cellular proliferation under conditions of abundant glucose, but failed to affect cells cultured in galactose medium. These data suggest that MOTS-c-induced respiratory suppression is likely secondary to increased glucose uptake (FIG. 15*h*).

Figure 15I:
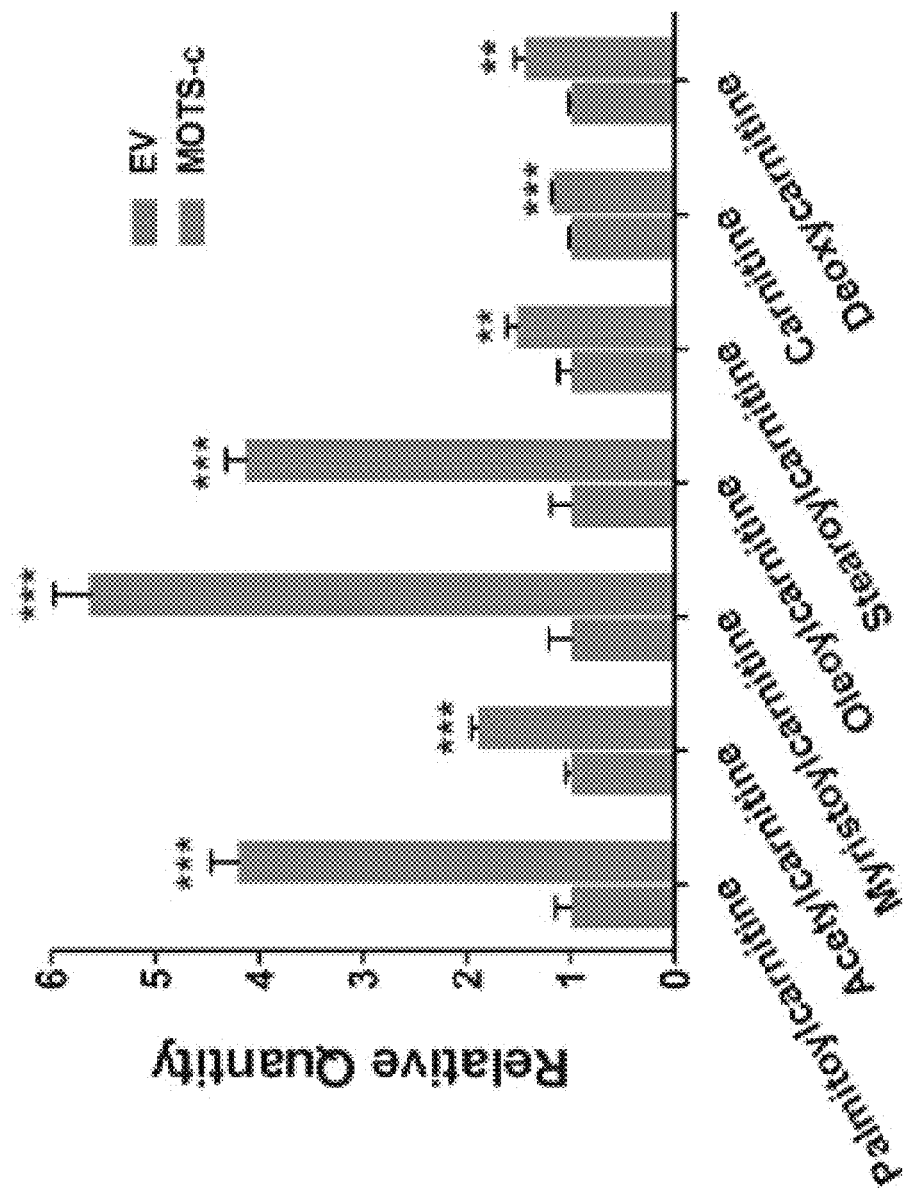
Figures 15J, 15K:
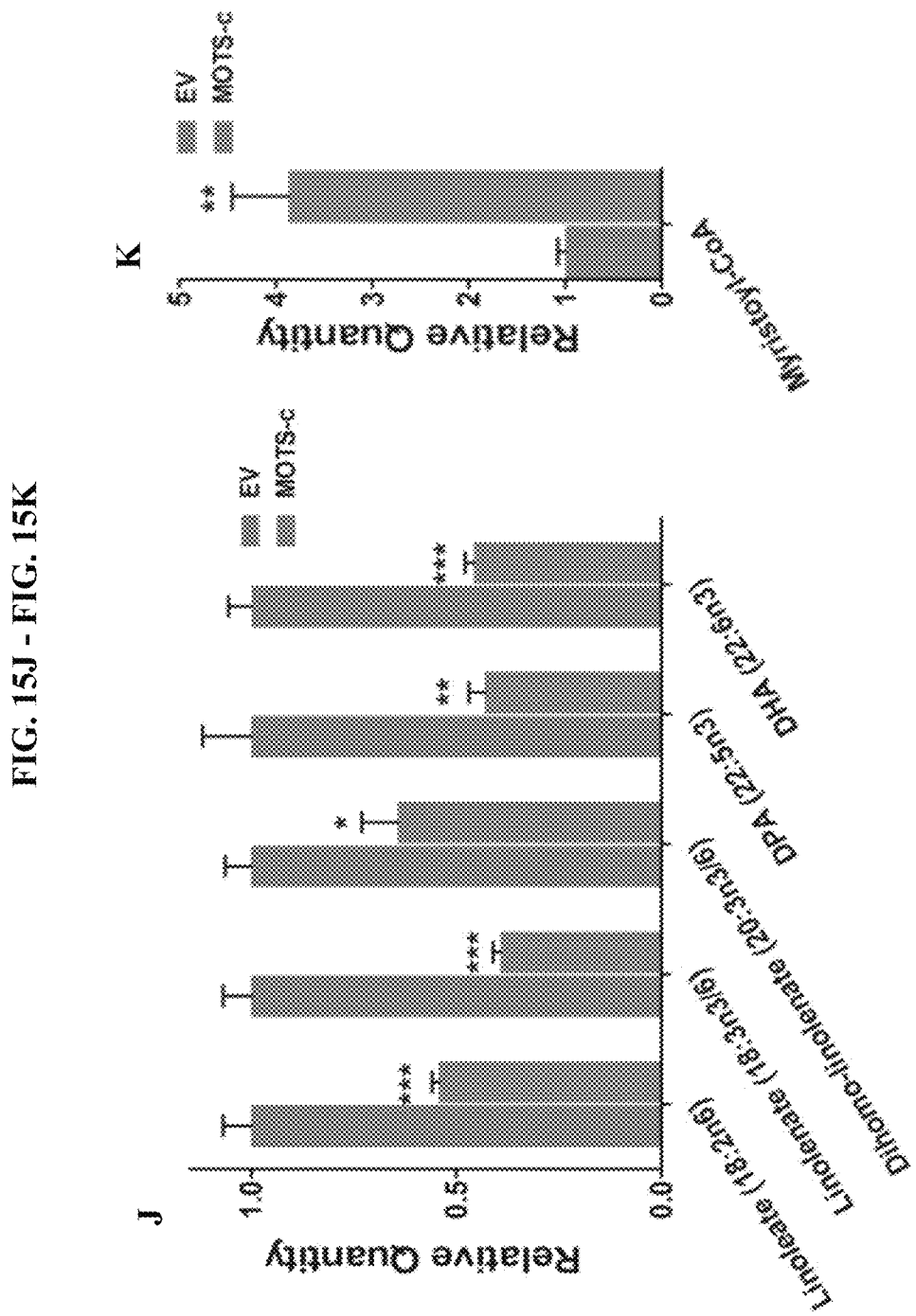
Figure 27A:
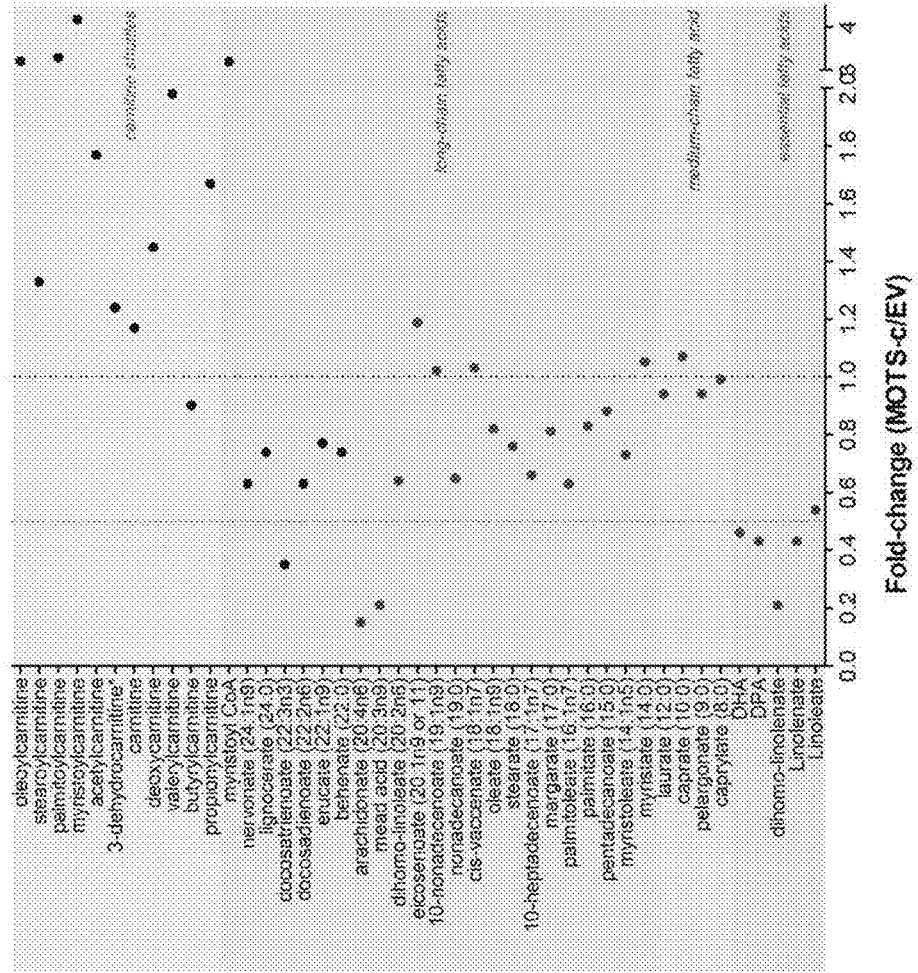
FIG. 27A-FIG. 27D describes the effect of MOTS-c on lipid metabolism. a, MOTS-c regulates lipid metabolism in HEK293 cells stably over-expressing MOTS-c. Exogenous MOTS-c treatment (10 µM; 24- or 72-hours) regulates the levels of b, the carnitine-shuttle system members, c, essential fatty acids, and d, the β-oxidation intermediate myristoyl-CoA. Student's t-test. *P<0.05, P<0.01, *P<0.001
Figures 27B, 27C, 27D:
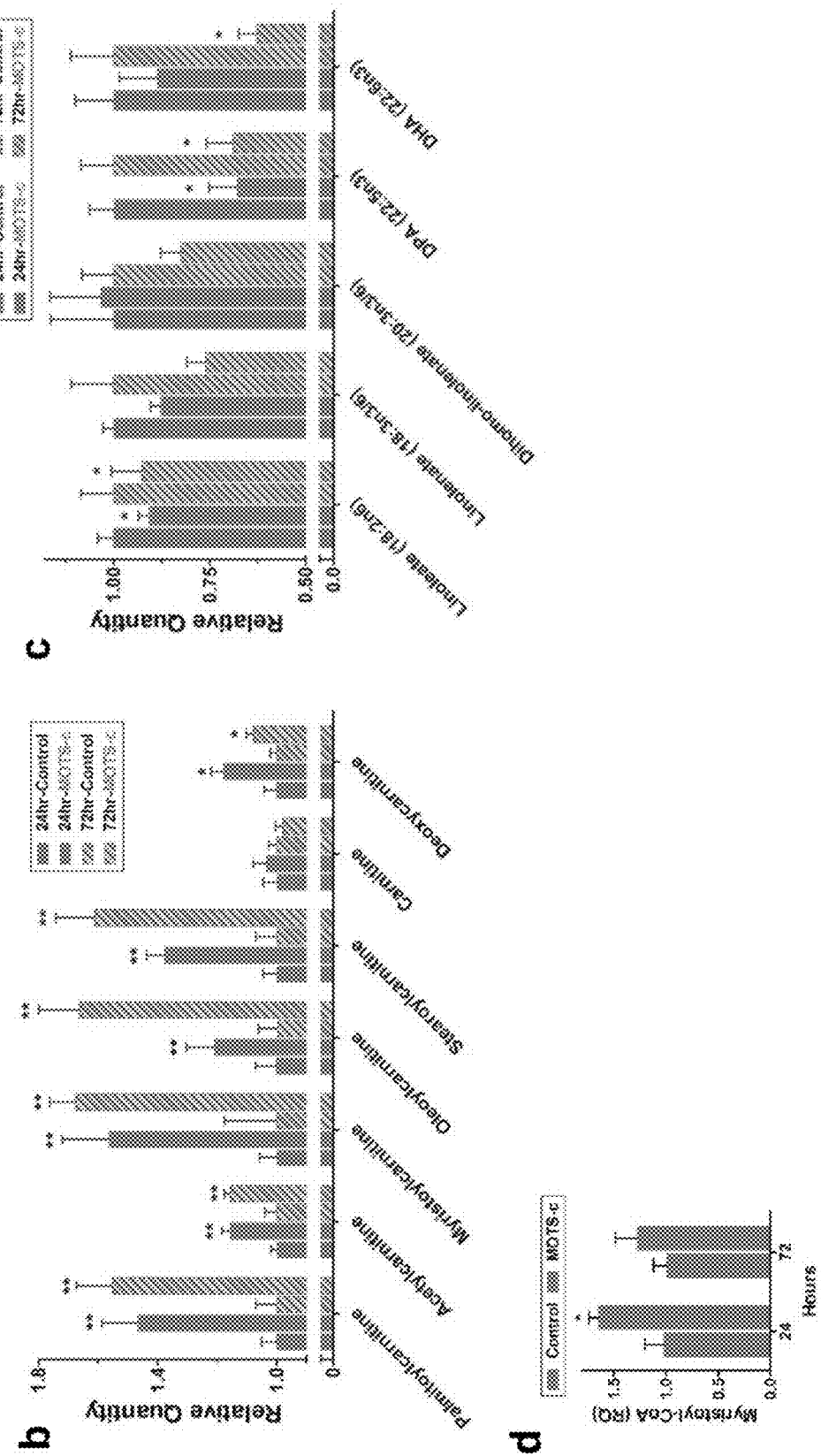
Figures 28A, 28B:
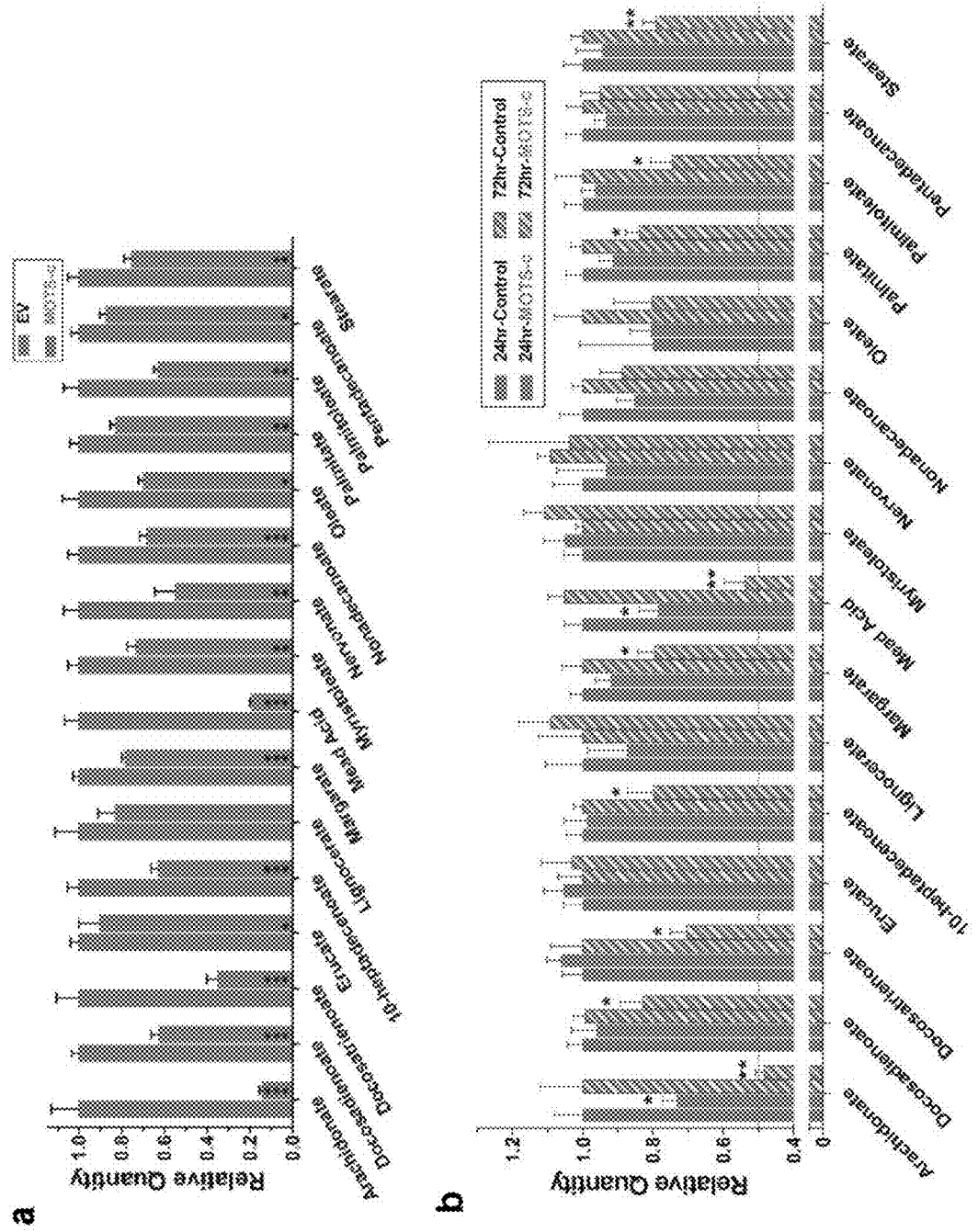
FIG. 28A-FIG. 28B describes the levels of long-chain fatty acids in a, HEK293 cells stably over-expressing MOTS-c and b, HEK293 cells treated with exogenous MOTS-c (10 µM) for 24- or 72-hours, determined by metabolomics (N=5). EV: HEK293 stably transfected with empty vector. Student's t-test. *P<0.05, P<0.01, *P<0.001

Lipid metabolism was also significantly affected by MOTS-c (FIG. 27*a*). MOTS-c-ST cells exhibited higher levels of carnitine shuttles, as well as increased concentrations of carnitine and deoxycarnitine compared with MOTS-c-EV cells (FIG. 15*i*). These findings were also observed, but to a lesser extent, in cells treated with exogenous MOTS-c (FIG. 27*b*). Consistent with increased carnitine shuttles, we found reduced levels of essential fatty acids in MOTS-c-ST cells (FIG. 15*j*), as well as in HEK293 cells treated with MOTS-c (FIG. 27*c*). After entering the mitochondria, fatty acids undergo β-oxidation to extract reducing potential and acetyl-CoA. Myristoyl-CoA, an early β-oxidation intermediate, was significantly increased in MOTS-c-ST cells (FIG. 15*k*), as well as HEK293 cells treated exogenously with MOTS-c (10 uM)(FIG. 27*d*). Furthermore, other long-chain fatty acids were also significantly reduced, suggesting increased fatty acid utilization (FIG. 28). Notably, β-oxidation itself is not an aerobic reaction, and increased fatty acid oxidation has been observed under reduced respiration during treatment with AICAR (L. D. Marroquin, J. Hynes, J. A. Dykens, J. D. Jamieson, Y. Will, *Circumventing the Crabtree effect: replacing media glucose with galactose increases susceptibility of HepG2 cells to mitochondrial toxicants. Toxicological sciences: an official journal of the Society of Toxicology* 97, 539 (June, 2007)) and metformin (A. Martin-Montalvo et al., *Metformin improves healthspan and lifespan in mice. Nature communications* 4, 2192 (Jul. 31, 2013)).

Figure 16A:
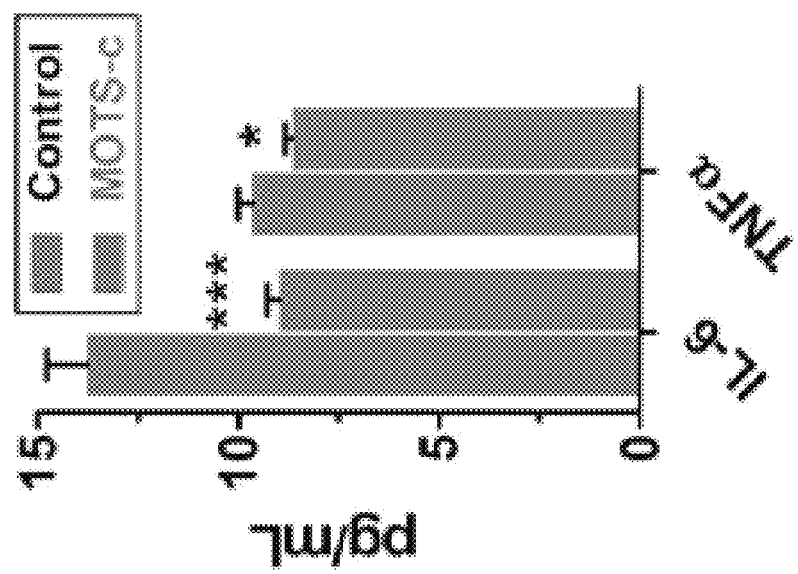
FIG. 16A-FIG. 16N describes MOTS-c regulates weight, metabolic homeostasis, and insulin sensitivity in mice. a, Effect of acute 4-day MOTS-c (5 mg/kg/day; IP; BID) treatment on circulating levels of the major adipokines IL-6 and TNFα in the outbred CD-1 male mice (N=6). b-f, 8-week old male CD-1 mice fed a high fat diet (60% by calories) or matched control diet (N=10). MOTS-c was injected intraperitoneally daily (0.5 mg/kg/day). b, body weight, c, blood glucose, d, insulin, e, liver H&E staining, f, skeletal muscle AMPK phosphorylation and GLUT4 levels. g, The effect of acute MOTS-c treatment (5 mg/kg/day; IP) for 7 days on intraperitoneal glucose tolerance test (IPGTT) performed on male C57BL/6 mice (N=7). h-j, Euglycemic-hyperglycemic clamps were performed on C57BL/6 mice fed a high-fat diet (60% by calories) and treated with MOTS-c (5 mg/kg/day; IP) for 7 days (N=6-8). h, glucose infusion rate (GIR), reflecting whole body insulin sensitivity, i, insulin-stimulated glucose disposal rate (IS-GDR), primarily reflecting muscle insulin sensitivity, and j, hepatic glucose production (HGP). k-l, MOTS-c levels in young (4-month) and aged (32-month) mice (N=3-4) decline in k, skeletal muscle, and l, circulation (serum). m, The effect of acute MOTS-c treatment (5 mg/kg/day; IP) for 7 days on insulin-stimulated (60 μU/ml) 2-deoxyglucose uptake into soleus muscles of young (3-month) and older (12-month) male C57BL/6 mice (N=6). n, proposed model for MOTS-c action. Data shown as mean±SEM. Student's t-test *P<0.05, P<0.01, *P<0.001.
Figure 16B:
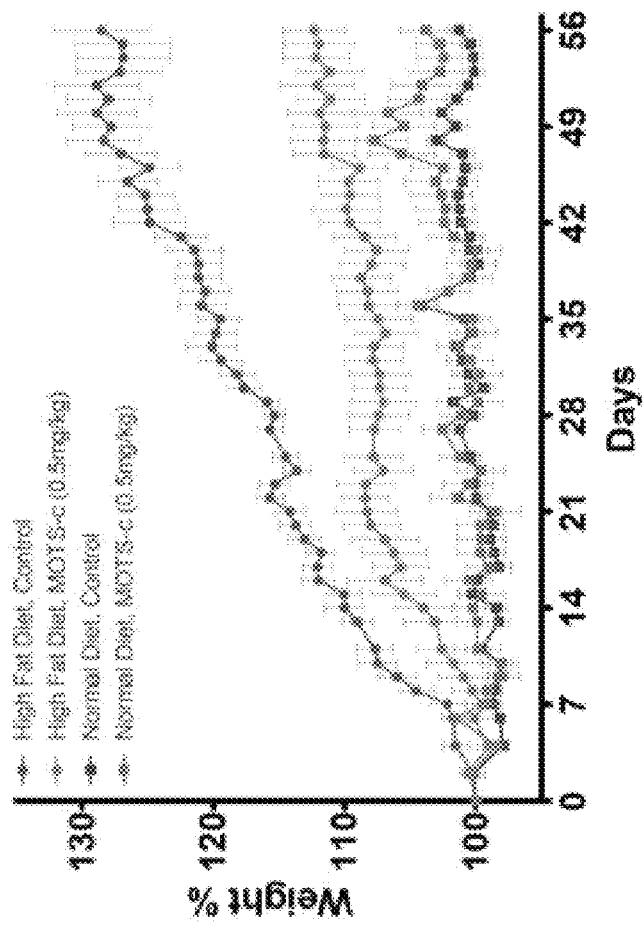
Figures 16C, 16D:
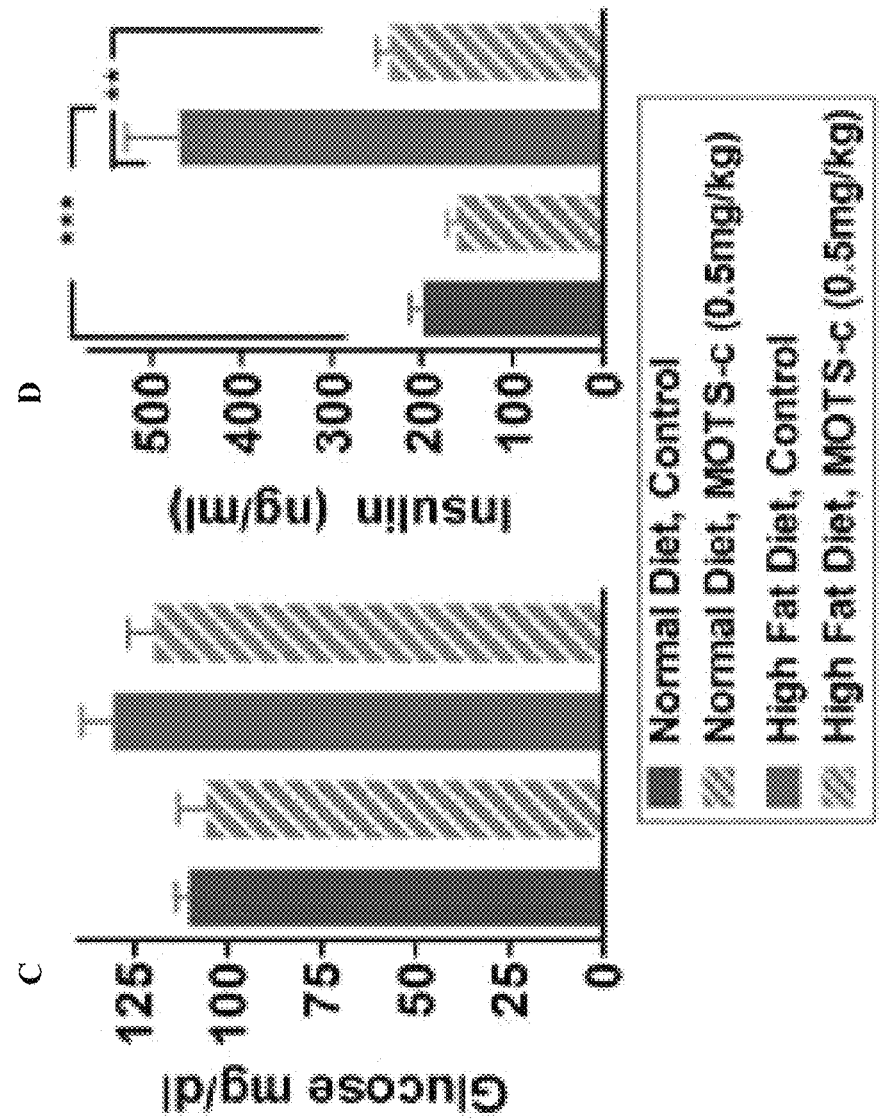
Figure 16E:
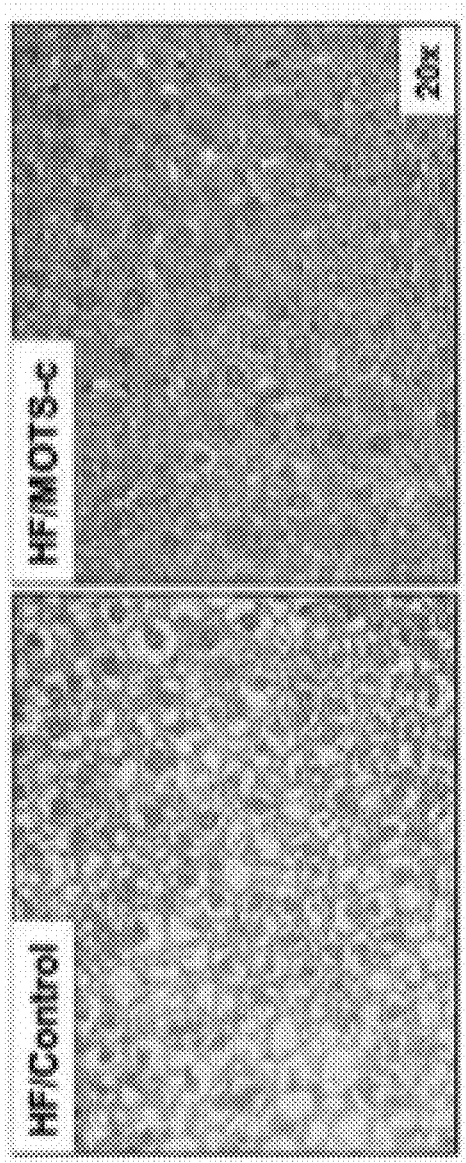
Figure 16F:
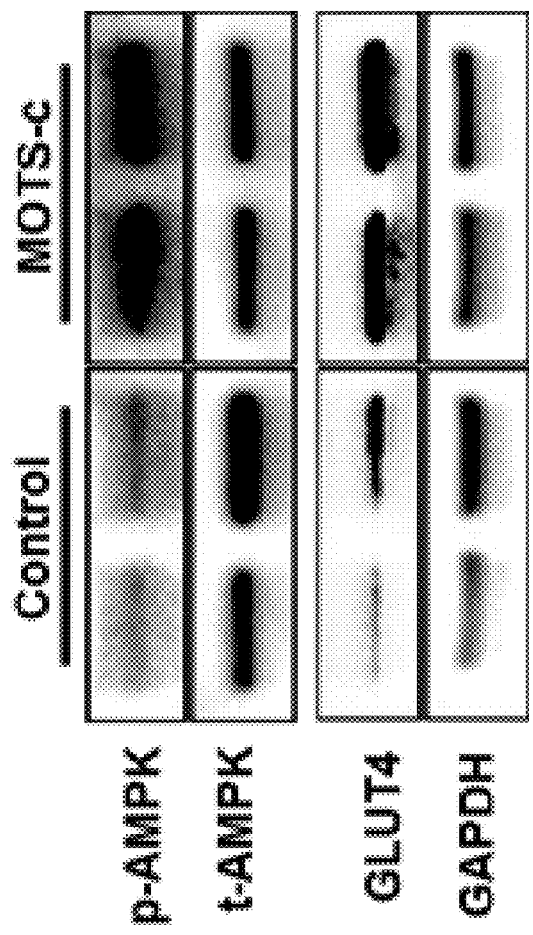
Figures 29A, 29B, 29C, 29D, 29E, 29F:
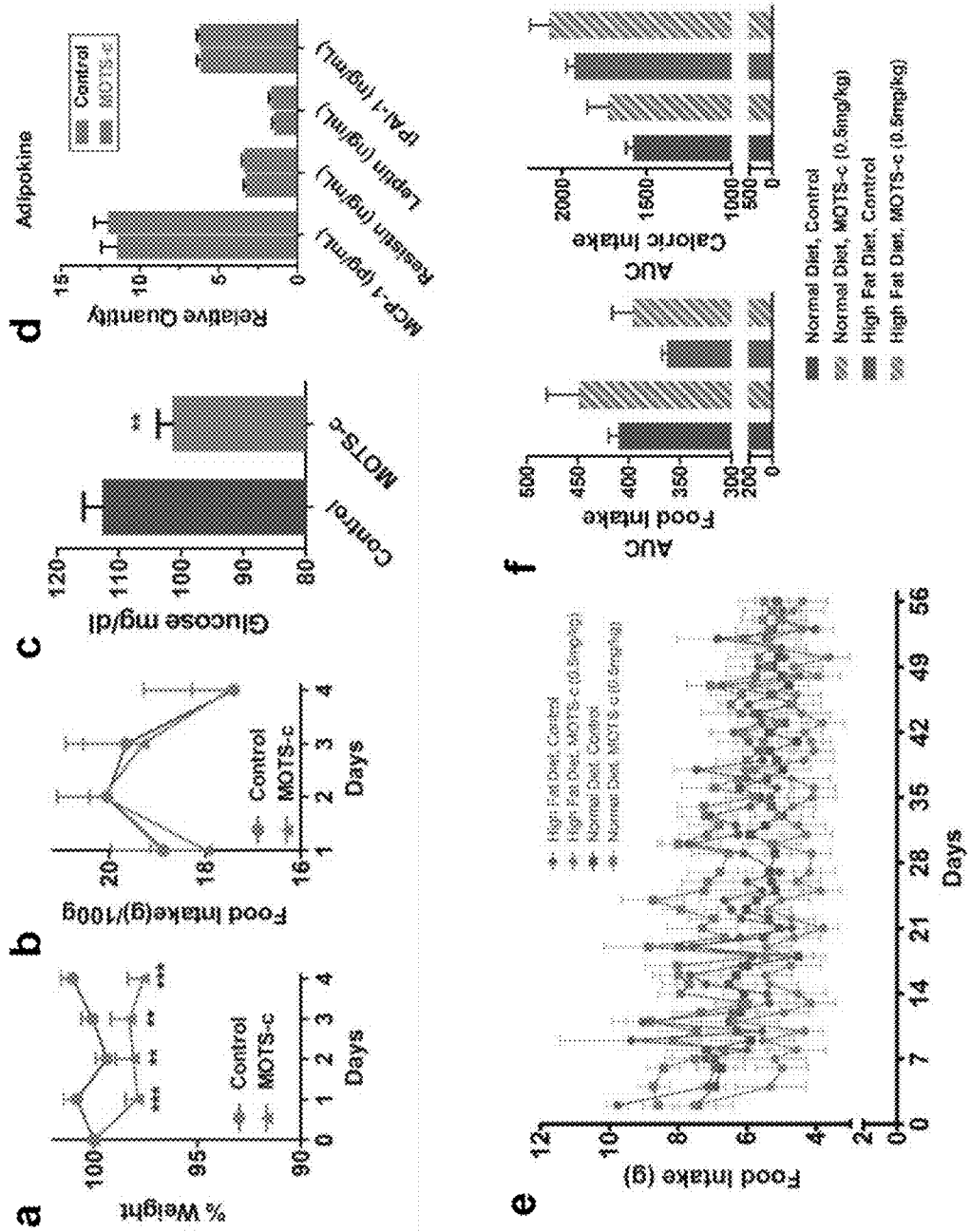
FIG. 29A-FIG. 29F describes the effect of acute MOTS-c (5 mg/kg/day; IP; BID) treatment for 4 days on a, body weight change (%), b, food intake, c, blood glucose, and d, adipokines in CD-1 male mice (N=6). e-f, The effect of MOTS-c (0.5 mg/kg/day) on e, daily food intake and f, total food/caloric intake of mice fed a high-fat diet (60% by calories) for 8 weeks. Student's t-test between groups within the same time point. *P<0.05, **P<0.01
Figure 33:
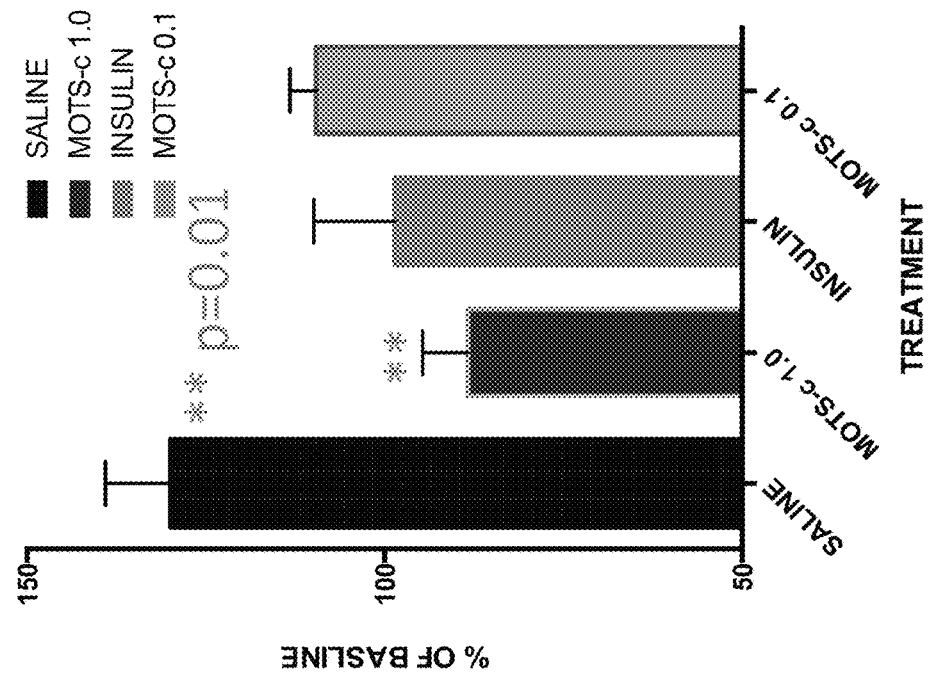
FIG. 33 describes Day 6 fasting blood sugars. ZDF diabetic rats were followed until their blood sugar was >300 ng/ml, at which point treatment was initiated with one of two doses of MOTS-c or insulin, given IV at 8 AM for 6 days. 6 rats per group were used. Fasting blood sugars were measured after 6-days. ANOVA and student t-tests were used for analysis and p-values.
Figure 34:
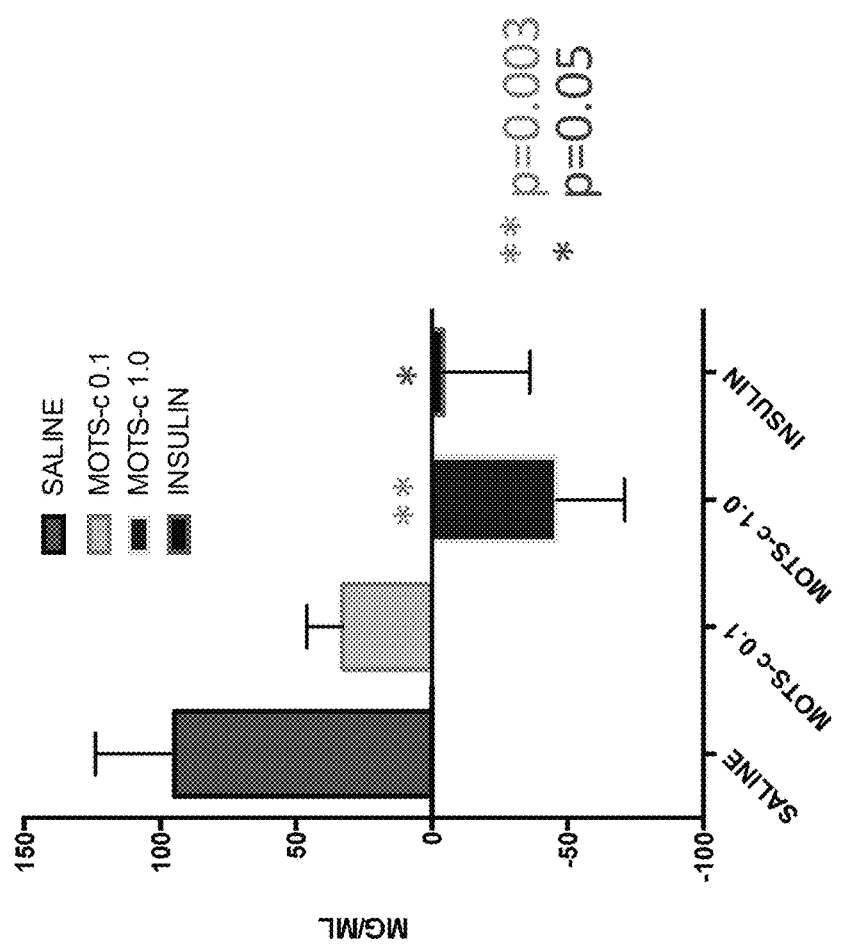
FIG. 34 describes absolute change in blood glucose at Day 6. In the same experiment described in FIG. 33, absolute changes in blood glucose are shown. Saline treated ZDF rats exhibit a further rise of 100 ng/ml in their blood sugar. Rats treated with daily insulin stabilize their blood sugar at levels similar to baseline, while MOTS-c treated rats (1 mg per 400 gram rat) show a substantial reduction of their blood sugar.
Figures 35A, 35B:
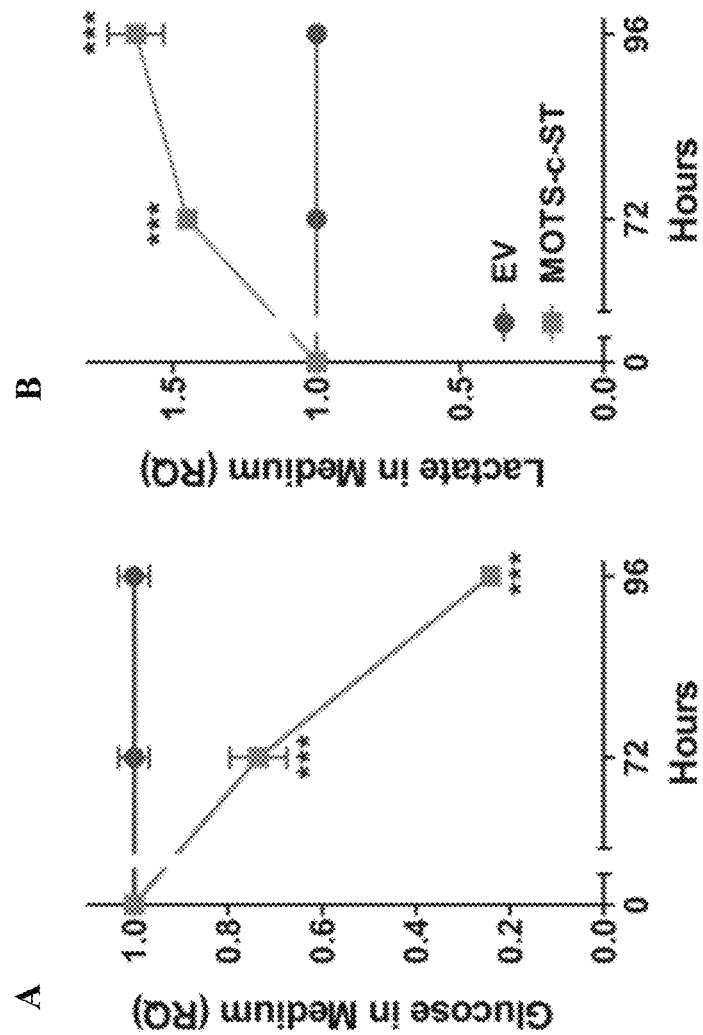
FIG. 35A-FIG. 35B describes MOTS-c stimulates glycolytic flux evidenced by increased glucose uptake and lactate production. Extracellular (A) glucose and (B) lactate in the culture medium of HEK293 cells stably over-expressing MOTS-c (N=6)
Figure 36:
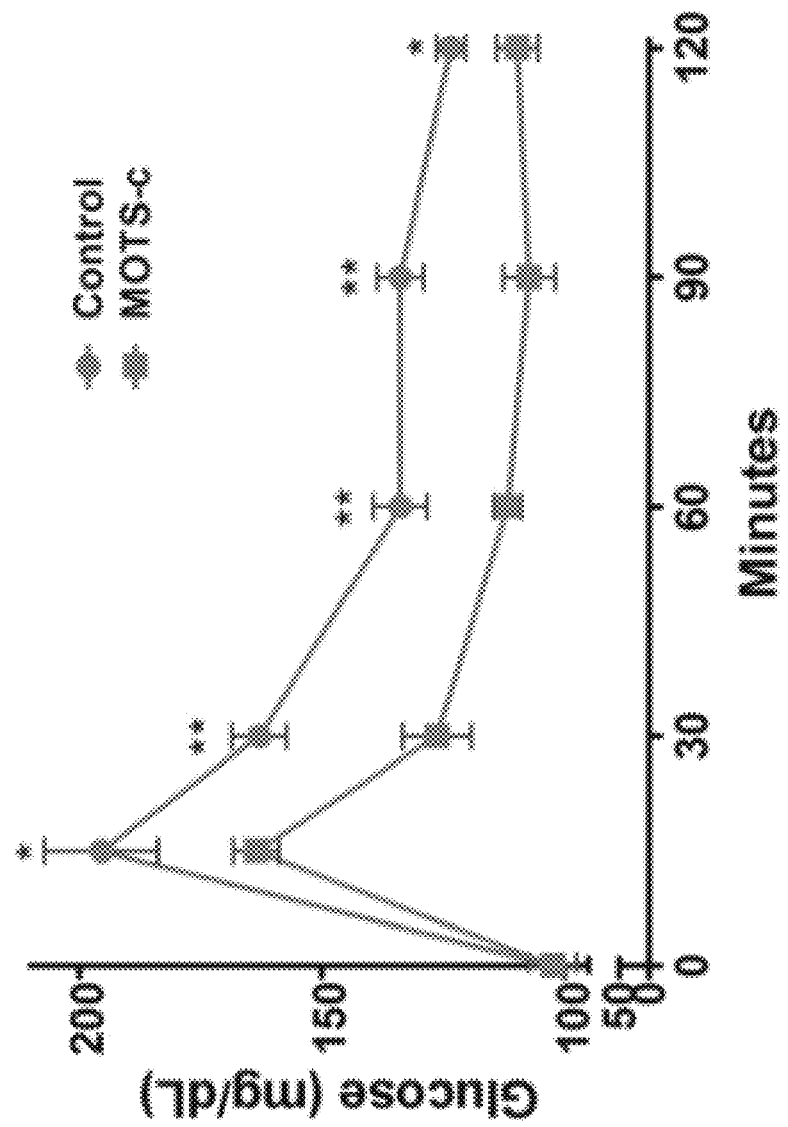
FIG. 36 describes MOTS-c enhances cellular glucose flux in vitro and acute treatment reduces glucose levels in mice fed a normal diet. To test insulin-sensitivity, we treated mice with intraperitoneal injections of MOTS-c (5 mg/kg/day) for 7 days and then subjected them to a glucose tolerance test (GTT; 1 g/kg glucose) in male C57BL/6 mice (N=7). We found significantly enhanced glucose clearance indicative of improved insulin sensitivity.
Figures 37A, 37B, 37C, 37D, 37E:
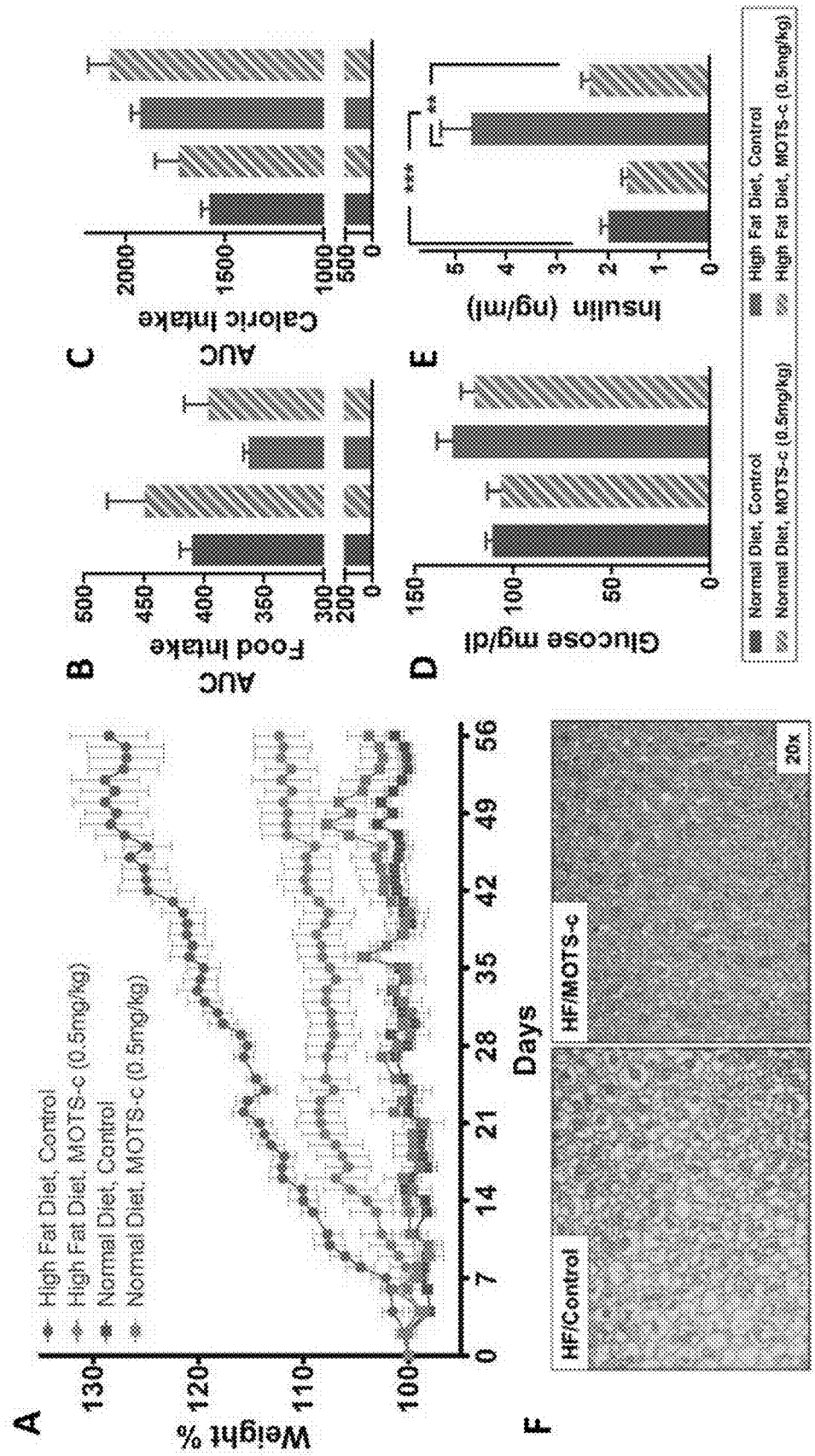
FIG. 37A-FIG. 37E describes testing of the effects of MOTS-c (0.5 mg/kg/day; IP) on metabolism in the context of a high-fat diet (HFD 60% by calories) (N=10). Although MOTS-c treatment had no effect on body weight when fed a normal diet, it remarkably prevented obesity in mice fed a HFD (A). (B-C) This difference in body weight was not attributed to food intake, as caloric intake was identical between the groups. (D-E) Additionally, MOTS-c treatment prevented HFD-induced hyperinsulinemia, indicating improved glucose homeostasis. (F) MOTS-c also reduced HFD-induced fatty liver determined by the liver H&E staining.
Figures 38A, 38B, 38C, 38D, 38E:
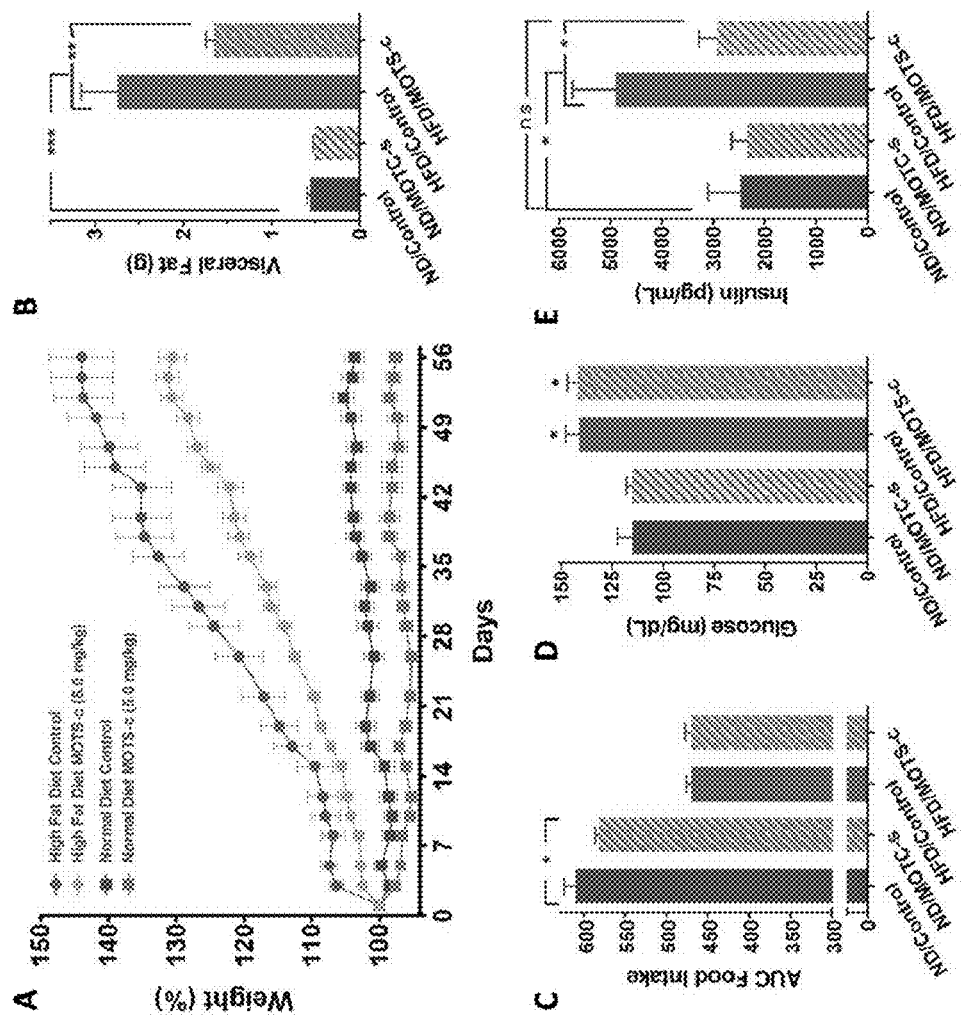
FIG. 38A-FIG. 38E describes testing of the effects of MOTS-c (5.0 mg/kg/day; IP) on high-fat diet (HFD 60% by calories) in mice from a different genetic background, C57BL/6 (N=12). (A) Similar to the CD-1 mice, MOTS-c treatment prevented obesity in C57BL/6 mice fed a HFD. (B) The reduced weight gain can be partially attributed to reduced levels of visceral fat. (C) This difference in body weight was not due to less food intake. Furthermore, MOTS-c treatment prevented HFD-induced hyperinsulinemia, indicating improved glucose homeostasis (D-E). ND: normal diet, HFD: high fat diet.
Figure 39:
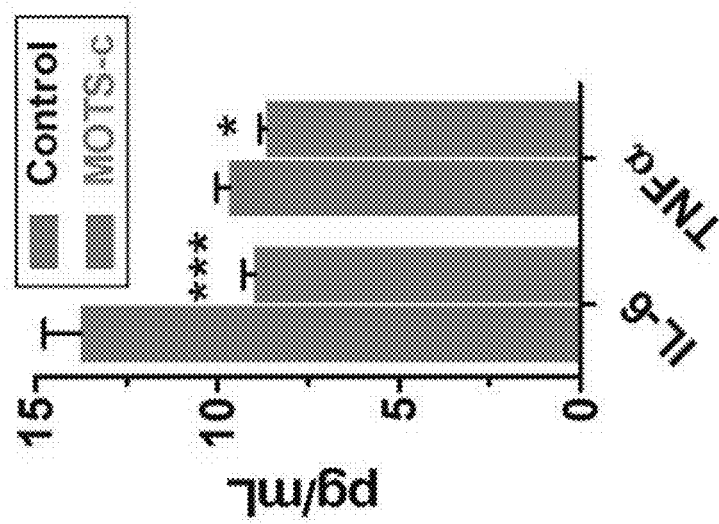
FIG. 39 shows the effect of MOTS-c on whole body metabolism, outbred CD-1 male mice fed a normal diet were treated with MOTS-c (5 mg/kg/day; BID, 4 days) or vehicle control (N=6). (4-day) treatment with MOTS-c reduced body weight, food and blood glucose levels. Also, basal levels of circulating IL-6 and TNFα (A), implicated in the pathogenesis of obesity and insulin resistance, were significantly reduced by MOTS-c treatment.
Figures 40A, 40B, 40C, 40D:
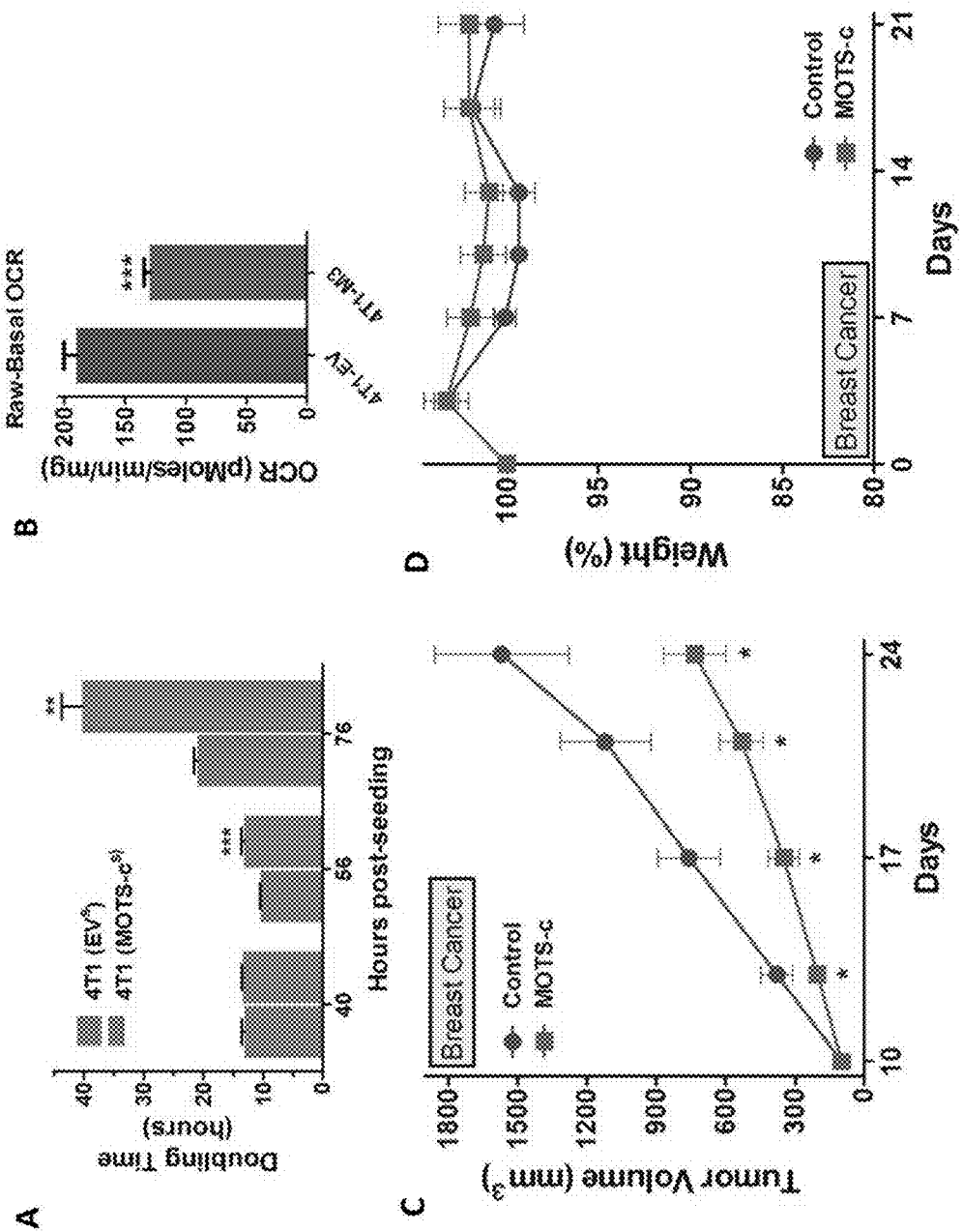
FIG. 40A-FIG. 40D shows cancer cells are known to have deranged metabolism to support its rampant growth. MOTS-c is regulator of metabolic homeostasis, and affects the proliferative capacity of a malignant cell. Breast cancer cells (4T1) stably over-expressing MOTS-c show (A) reduced proliferation rate and (B) reduced respiration. Also, (C) MOTS-c treatment retarded breast cancer (4T1) proliferation in a subcutaneous allograft mouse model; (D) MOTS-c treatment was not toxic as reflected by stable body weight maintenance.
Figures 41A, 41B, 41C, 41D:
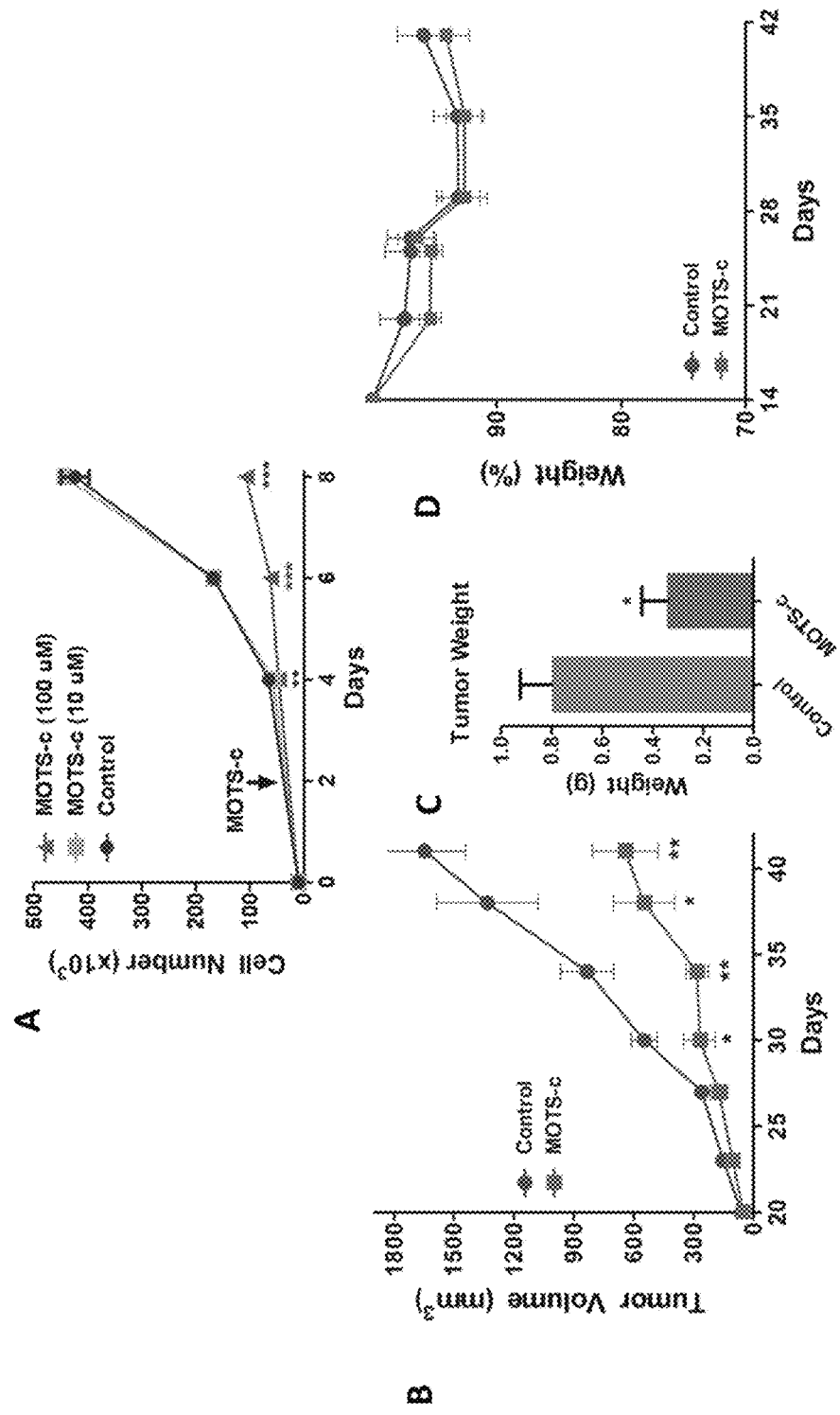
FIG. 41A-FIG. 41D shows that similar to the breast cancer, MOTS-c also retards the growth of a prostate cancer cells. (A) MOTS-c treatment retarded prostate cancer cell (22Rv1) proliferation in vitro. (B-C) Also, MOTS-c treatment retarded prostate cancer (22Rv1) proliferation in a subcutaneous allograft mouse model; (D) MOTS-c treatment was not toxic as reflected by stable body weight maintenance.
Figures 42A, 42B, 42C, 42D:
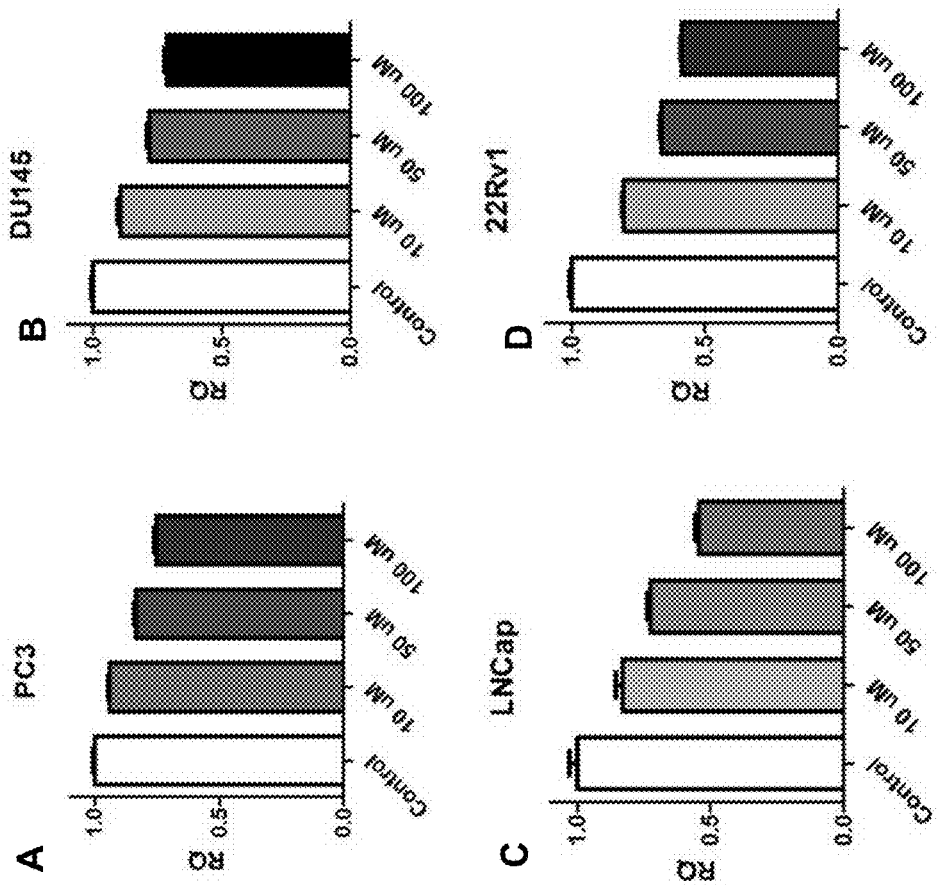
FIG. 42A-FIG. 42D describes that MOTS-c treatment retards proliferation of 4 different prostate cancer cell lines in vitro in a dose dependent manner. MTT reduction was used to assess cellular proliferation and relative quantity (RQ) to the control is presented. Cells were treated for 48-72 hours in optimum growth conditions.

Acute treatment of MOTS-c in outbred CD-1 male mice for 4 days (5 mg/kg/day; BID) caused modest reductions in body weight, food intake, and blood glucose levels (FIG. 29*a-c*), but significantly reduced basal levels of plasma IL-6 and TNFα (FIG. 16*a*; FIG. 29*d*), which are implicated in obesity and insulin resistance (M. F. Gregor, G. S. Hotamisligil, *Inflammatory mechanisms in obesity. Annual review of immunology* 29, 415 (2011)). Considering our findings in cultured cells, the effects of MOTS-c on metabolism in the outbred CD-1 mice fed a high-fat diet (HFD; 60% by calories) were tested (L. A. Scrocchi, D. J. Drucker, Effects of aging and a high fat diet on body weight and glucose tolerance in glucagon-like peptide-1 receptor −/− mice. *Endocrinology* 139, 3127 (July, 1998) and W. L. Breslin, K. Strohacker, K. C. Carpenter, L. Esposito, B. K. McFarlin, Weight gain in response to high-fat feeding in CD-1 male mice. *Laboratory animals* 44, 231 (July, 2010)). 8-weeks of MOTS-c treatment had no effect on body weight in mice fed a normal diet, but remarkably prevented HFD-induced obesity (FIG. 16b). This difference in body weight was not attributed to food intake, as caloric consumption was identical between the groups (FIG. 29e-f). High fat feeding promotes hyperinsulinemia in an attempt to overcome peripheral insulin resistance to maintain glucose homeostasis (M. Hou et al., *Protective effect of metformin in CD1 mice placed on a high carbohydrate-high fat diet. Biochemical and biophysical research communications* 397, 537 (Jul. 2, 2010)). Importantly, MOTS-c treatment prevented hyperinsulinemia (FIG. 16c, d) and ameliorated hepatic lipid accumulation in HFD fed mice (FIG. 16e). Notably, in line with our in vitro studies, MOTS-c promoted AMPK activation and GLUT4 expression in the muscle of these HFD fed mice (FIG. 16f).

Figure 16G:
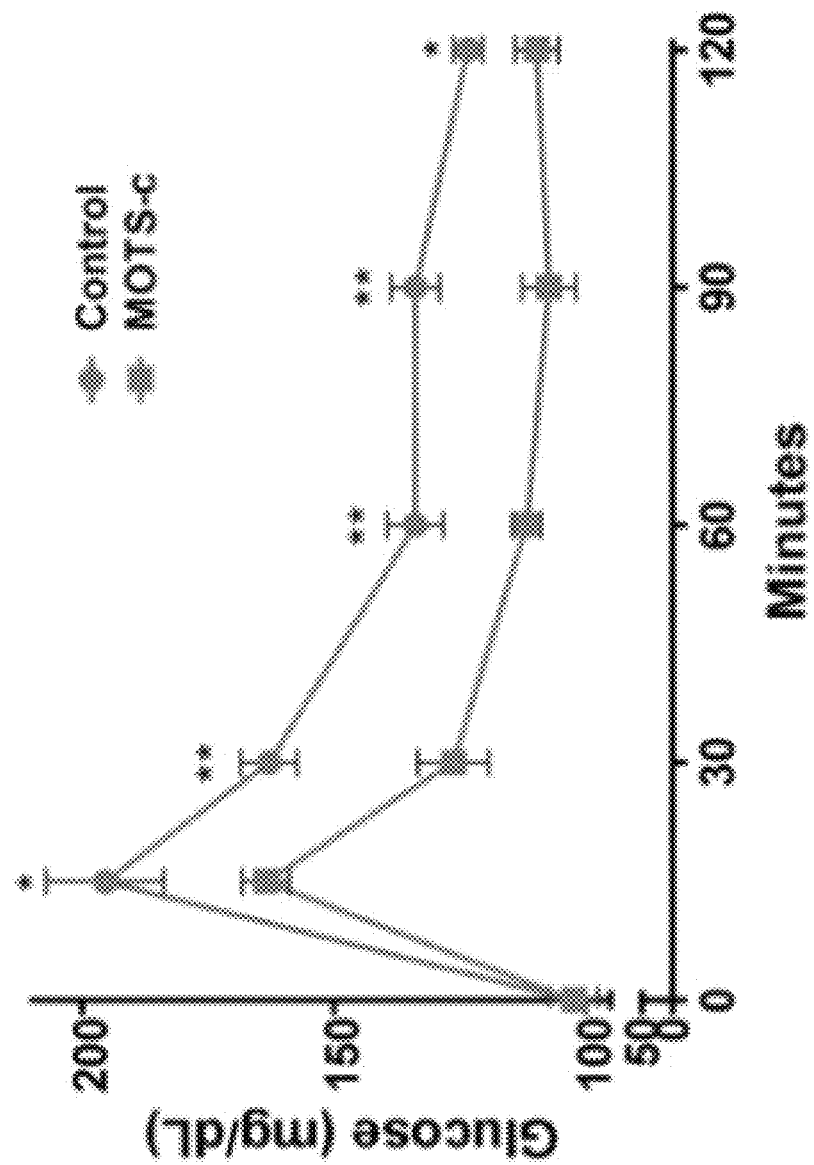
Figures 16H, 16I, 16J:
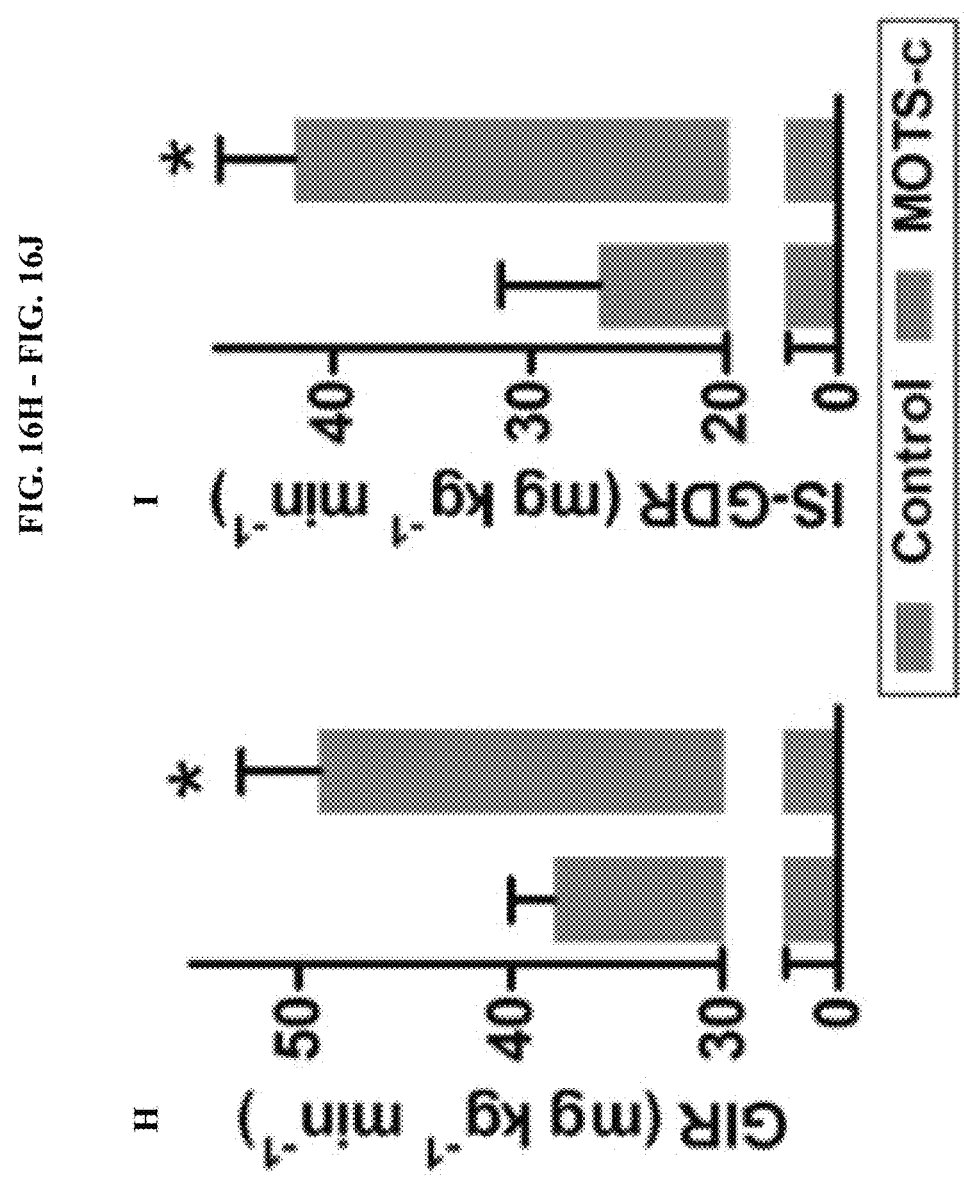
Figure 16K:
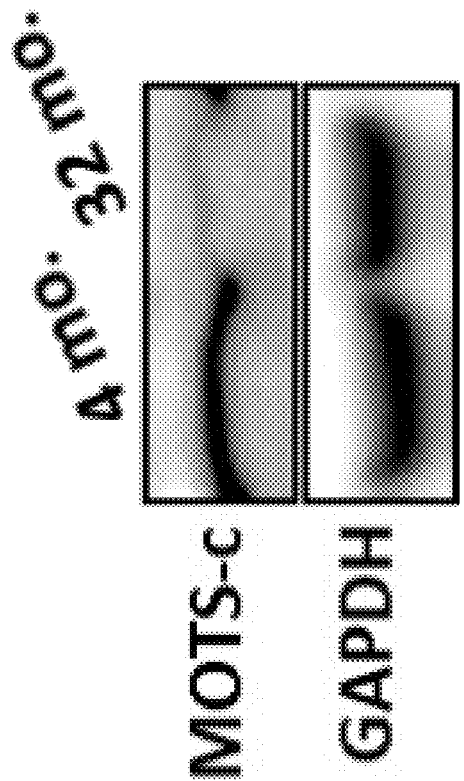
Figure 16L:
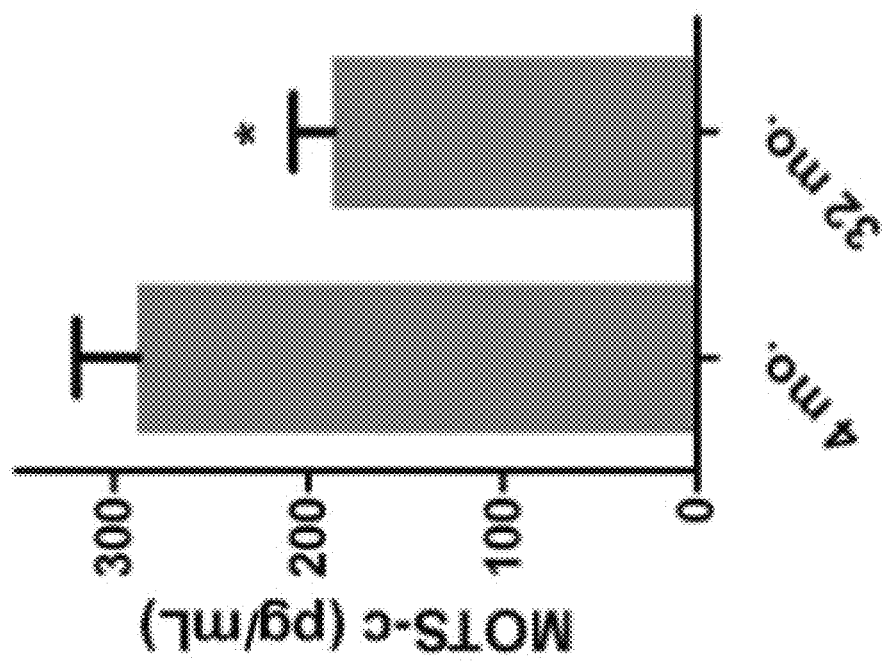
Figure 16M:
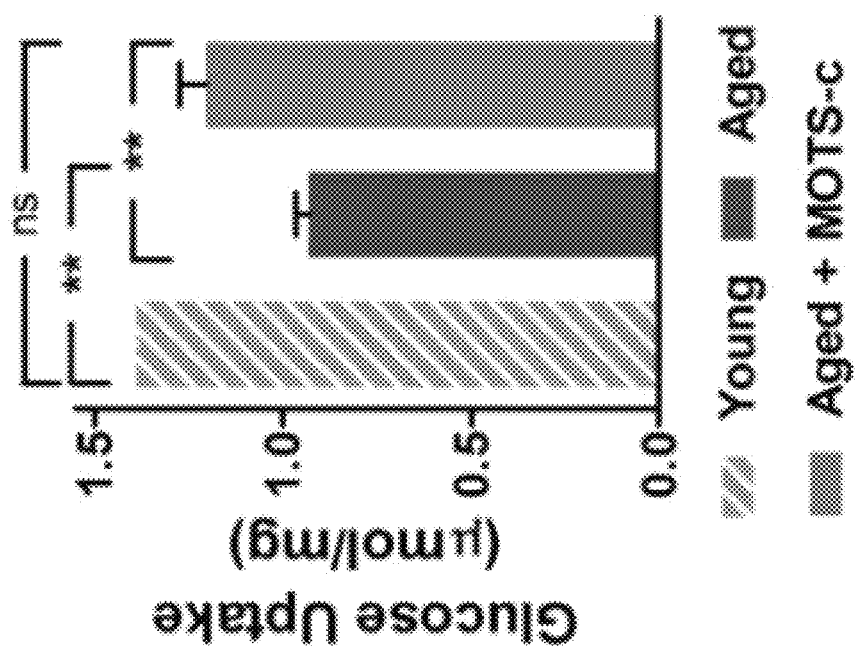

Next, the effects of MOTS-c on glucose homeostasis in the commonly studied, obesity prone C57BL/6 mouse strain were tested by performing a glucose tolerance test (GTT). MOTS-c treated mice showed rapid glucose clearance, suggesting enhanced insulin sensitivity (FIG. 16g). Next, hyperinsulinemic-euglycemic clamp studies were performed to quantify the effects of 7-day treatment with MOTS-c on whole body insulin sensitivity independent of changes in body weight that occur with extended treatment durations. MOTS-c improved whole body insulin sensitivity as reflected by a ~30% increase in the exogenous glucose infusion rate (GIR) required to maintain euglycemia during insulin stimulation (FIG. 16h). Insulin promotes glucose disposal into peripheral tissues and suppresses hepatic glucose production (HGP) to maintain homeostasis during periods of increased glucose availability (C. R. Kahn, Banting Lecture. *Insulin action, diabetogenes, and the cause of type II diabetes. Diabetes* 43, 1066 (August, 1994)). Tritiated glucose was infused during the clamp to determine the tissue specificity of MOTS-c action on insulin sensitivity. Although it was observed that MOTS-c treatment significantly enhanced the insulin-stimulated glucose disposal rate (IS-GDR) (FIG. 16i), no effect of MOTS-c on liver insulin sensitivity was detected, as the rate of hepatic glucose production (HGP) was comparable between the groups (FIG. 16j). Considering that 70-85% of insulin-stimulated glucose disposal is into skeletal muscle, MOTS-c actions to enhance insulin sensitivity and glucose homeostasis may be mediated in this tissue. Indeed this notion was supported by strong AMPK activation and increased GLUT4 expression in skeletal muscle of HFD-fed mice following MOTS-c treatment (FIG. 16f). Moreover, MOTS-c also enhanced glucose uptake into soleus muscle stimulated with a physiological dose of human insulin ex vivo. Because MOTS-c levels in muscle (FIG. 16k) and in circulation (FIG. 16l) decline concomitant with the development of insulin resistance during aging (C. R. Kahn, Banting Lecture. *Insulin action, diabetogenes, and the cause of type II diabetes. Diabetes* 43, 1066 (August, 1994)), it was determined if MOTS-c could reverse age-dependent impairments in insulin action by measuring insulin-stimulated glucose (2-deoxyglucose) uptake into soleus muscles of middle-aged (12 months) and young (3 months) male C57BL/6 mice. Signs of insulin resistance begin to show around 12 months of age in C57BL/6 mice (C. R. Kahn, Banting Lecture. *Insulin action, diabetogenes, and the cause of type II diabetes. Diabetes* 43, 1066 (August, 1994)). Indeed muscles from older mice were more insulin resistant, but 7 days of MOTS-c treatment restored sensitivity comparable to young animals (FIG. 16m).

Discussion

Technological advances have unveiled previously unknown properties of mitochondrial genetics suggesting the existence of small ORFs in the mitochondrial DNA (T. R. Mercer et al., *The human mitochondrial transcriptome. Cell* 146, 645 (Aug. 19, 2011)). Notably, various bioactive small ORFs in the nuclear genome have been reported in *Drosophila* (E. G. Magny et al., *Conserved regulation of cardiac calcium uptake by peptides encoded in small open reading frames. Science* 341, 1116 (Sep. 6, 2013); J. Savard, H. Marques-Souza, M. Aranda, D. Tautz, *A segmentation gene in tribolium produces a polycistronic mRNA that codes for multiple conserved peptides. Cell* 126, 559 (Aug. 11, 2006); T. Kondo et al., *Small peptides switch the transcriptional activity of Shavenbaby during Drosophila embryogenesis. Science* 329, 336 (Jul. 16, 2010).; and M. I. Galindo, J. I. Pueyo, S. Fouix, S. A. Bishop, J. P. Couso, *Peptides encoded by short ORFs control development and define a new eukaryotic gene family. PLoS biology* 5, e106 (May, 2007)). There is evidence in the literature discussing the potential existence of factors encoded within the mitochondrial DNA (mtDNA). For instance, polyadenylated mitochondrial rRNA clones were cloned in the early 1980s, as part of a cDNA library constructed from interferon-induced human myeloblast cells (J. Villegas, P. Araya, E. Bustos-Obregon, L. O. Burzio, *Localization of the 16S mitochondrial rRNA in the nucleus of mammalian spermatogenic cells. Molecular human reproduction* 8, 977 (November, 2002)), suggesting a strong interferon-induced factor encoded in the mtDNA. Also, in humans, the 16S rRNA was found localized in the nucleus of human spermatogenic cells (J. Durieux, S. Wolff, A. Dillin, *The cell-non-autonomous nature of electron transport chain-mediated longevity. Cell* 144, 79 (Jan. 7, 2011)), whereas in *Drosophila*, mitochondrial rRNAs have been found in the cytoplasm where they play a role in germ cell establishment (R. Amikura, M. Kashikawa, A. Nakamura, S. Kobayashi, *Presence of mitochondria-type ribosomes outside mitochondria in germ plasm of Drosophila embryos. Proceedings of the National Academy of Sciences of the United States of America* 98, 9133 (Jul. 31, 2001)).

MOTS-c may be a product of adaptation for effective bilateral communication between mitochondria and the cell or distant organs such as skeletal muscle, especially considering that its translation requires the mammalian genetic code. Herein is provided sufficient evidence to suggest MOTS-c, and humanin, as a novel class of inherent mitochondrial signals that regulate global physiology (C. Lee, K. Yen, P. Cohen, *Humanin: a harbinger of mitochondrial-derived peptides? Trends in endocrinology and metabolism: TEM*, (Feb. 7, 2013)). A recent report, using the nematode *C. elegans*, showed that mitochondrial disruption in neurons causes mitochondrial unfolded-protein response (UPR) in the intestine and extends lifespan, an effect mediated by an unidentified circulating signal that allows inter-organ communication of stress (D. K. Woo, G. S. Shadel, *Mitochondrial stress signals revise an old aging theory. Cell* 144, 11 (Jan. 7, 2011) and C. Cheadle, M. P. Vawter, W. J. Freed, K. G. Becker, *Analysis of microarray data using Z score transformation. The Journal of molecular diagnostics: JMD* 5, 73 (May, 2003)).

Figure 16N:
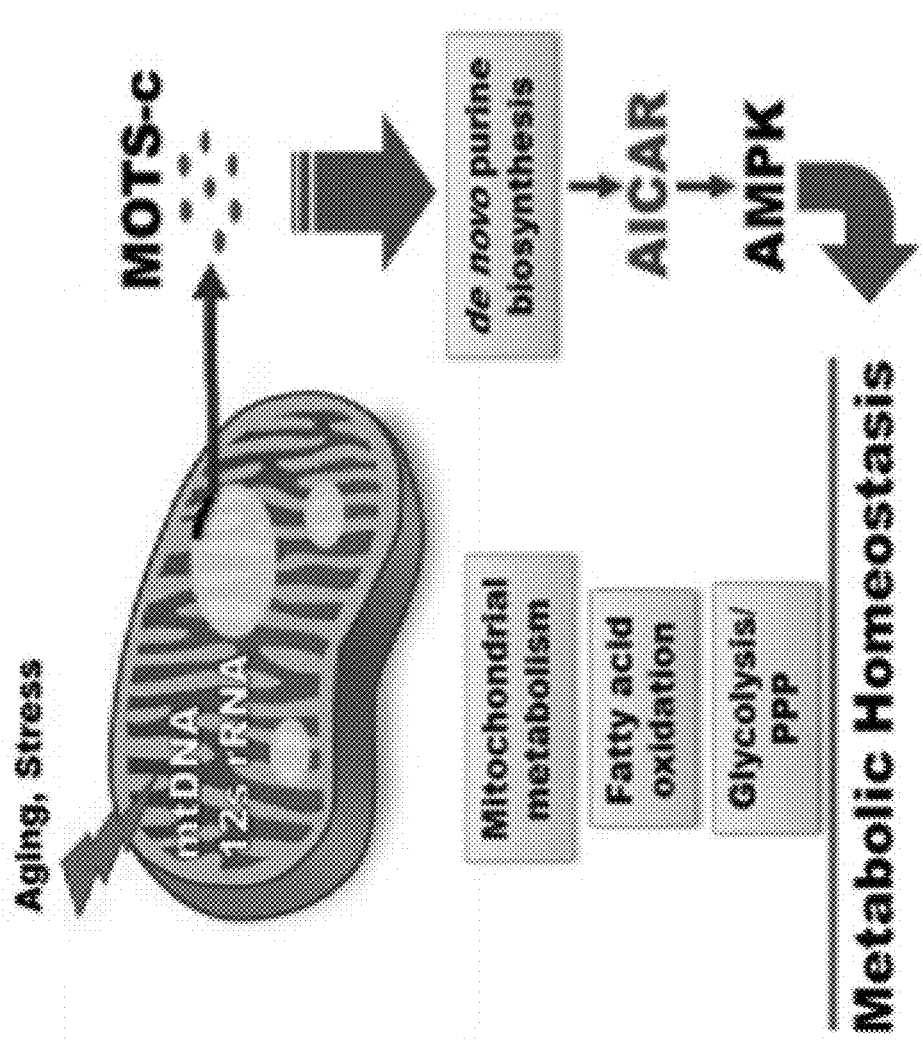

Although the specific mechanistic details of MOTS-c action have yet to be fully identified, its impact on metabolism will likely have major implications for aging and age-related diseases including diabetes, cancer, atherosclerosis, and neurodegeneration. The emerging biology of MDPs and the unique involvement of AICAR and AMPK in MOTS-c action (FIG. 16n) provide an interesting opportunity to expand our understanding of the role of mitochondria in physiological and pathological conditions, as well as identifying novel diagnostic and therapeutic targets.

Methods

Cell Culture

HEK293 and HeLa cells were routinely cultured in Dulbecco's modified Eagle's medium (DMEM) supplemented with 10% fetal bovine serum (FBS) at 37° C. with 5% $CO_2$. ρ0 cells, which are devoid of mitochondrial DNA, were generated by culturing HeLa cells in low doses of ethidium bromide (EtBr; 100 ng/mL) as described before (K. Hashiguchi, Q. M. Zhang-Akiyama, *Establishment of human cell lines lacking mitochondrial DNA*. Methods in molecular biology 554, 383 (2009)). MOTS-c-ST cells were generated by selection in and maintenance in G418 (500 µM; Sigma) in DMEM with 10% FBS.

Mice

All animal work was performed in accordance with the University of Southern California and University of California Los Angeles Institutional Animal Care and Use Committee. MOTS-c (Genscript, USA) was injected daily via intraperitoneal injections in all in vivo experiments. 8-week old CD-1 (ICR) mice were purchased from Harlan. C57BL/6 mice were purchased from Jackson Laboratories. Mice were fed a high-fat diet (60% by calories) and matching control diet purchased from Research Diets (Cat# D12492 and D12450J, respectively) for 8 weeks. Pellets were replaced twice weekly, and body weight and food consumption were recorded daily (N=10).

Cloning

Directional cloning using restriction enzymes EcoRI (5') and XhoI (3') was performed to construct MOTS-c expression clones. MOTS-c and MOTS-c-HA nucleotide sequences flanked by the restriction enzymes were synthesized and 5' phosphorylated (IDT, USA), hybridized, and ligated with digested pcDNA3.1(+) (Invitrogen, USA), or pcDNA-IRES GFP (kind gift from Nir Barzilai at AECOM). All enzymes were purchased from NEB (USA) unless stated otherwise.

Immunocytochemistry

HEK293 cells plated on coverslip were fixed with 4% paraformaldehyde for 15 min at room temperature. After fixation, the cells were permeablized with 0.2% Triton X-100 in phosphate-buffered saline (PBS) for 10 minutes at room temperature and were blocked in PBS containing 0.2% Triton X-100 and 1% bovine serum albumin (BSA) for 1 hour at room temperature. Cells were then incubated with rabbit anti-MOTS-c antibody (1:50) and goat anti-hsp60 antibody (1:100; Santa Cruz Biotechnology, USA) in PBS containing 0.2% Triton X-100 and 1% BSA at 4° C. overnight. After three washes with PBS, the cells were further incubated with Alexa Fluor 488-conjugated donkey anti-rabbit IgG (1:200; Invitrogen, US) and Alexa Fluor 568-conjugated donkey anti-goat IgG (1:200; Invitrogen) in PBS containing 0.2% Triton X-100 and 1% BSA for 1 hour at room temperature. Nuclei were stained for 5 minutes at room temperature in PBS containing Hoechst 33258 (2 mg/ml; Invitrogen). Specificity of immunostaining was demonstrated by using MOTS-c antibody after incubation with 69 µg/ml MOTS-c peptide (Genscript, USA) for 1 hour at room temperature. Coverslips were mounted with Pro-Long Gold antifade reagent (Invitrogen) and observed under an ELYRA PS.1 (Carl Zeiss, Germany) using Laser wide field. For structured illumination microscopy (SIM) images, Z-stack sections were collected with five rotations of gratings and images were was reconstructed using ELYRA PS.1 software.

Immunoassays

The entire MOTS-c peptide was conjugated to Keyhole limpet hemocyanin (KLH) and injected into rabbits. IgG purified serum were used for western blotting and ELISA. Circulating MOTS-c levels were measured from serum, plasma, and CSF by in-house sandwich ELISA developed at USC. The custom rabbit anti-MOTS-c polyclonal anti-sera were produced at YenZym Antibodies, LLC (South San Francisco, Calif.). IgG subclasses purified with a protein A/G column chromatography (Pierce, Rockford, Ill.) was used as a capture antibody. The anti-MOTS-c IgG was labeled with biotin and used as a detection antibody. To measure endogenous MOTS-c levels, synthetic MOTS-c (GenScript) was used as a standard within the range of 25 pg/mL to 6400 pg/mL. Prior to assay, MOTS-c was extracted in 90% acetonitrile and 10% 1N HCl. Briefly, 200 µL of extraction reagent was added to 100 µL of plasma, gently mixed and incubated at room temperature for 30 minutes. The mixture was centrifuged and the supernatant was removed and dried. The dried extract was reconstituted with 200 µL of phosphate buffer with 0.5% Tween 20, and then used for assay. 96-well microtiter plates were coated with capture antibody at 0.5 µg/well and incubated 4 hr at room temperature on a shaker. Standards, controls or extracted samples and pre-titered detection antibody were added to the appropriate wells and incubated overnight after 2 washes with wash buffer and 2 washes with Superblock buffer (Pierce Chemicals, Rockford, Ill.). Wells were washed 3 times and then added with streptavidin-HRP and further incubated for 30 minutes at room temperature. After washes, 200 µL/well of OPD solution (1 mg/mL in hydrogen peroxide substrate) was added and incubated for 10-20 minutes. The reaction was terminated by the addition of 2N $H_2SO_4$, and absorbance was measured on a plate spectrophotometer (Molecular Designs, Sunnyvale, Calif.) at 490 nm. The intra- and inter-assay coefficient variations (CV) were less than 10%. Plasma insulin levels were detected using a mouse insulin assay kit (MSD; Cat# K112BZC-1) and Sector Imager 2400A (MSD, USA).

For western blotting, protein samples were prepared in 1% Triton X-100 with EDTA-free protease and phosphatase inhibitors (Roche, USA), heated at 95° C. for 5 minutes, ran on 4-20% gradient tris-glycine gels (TGX; Bio-Rad, USA) and transferred to PVDF membranes (Bio-Rad) using a turbo semidry transfer system (Transblot Turbo; Biorad) at 9V for 15-30 minutes. Membranes were blocked with 5% BSA for 30 minutes and incubated with primary antibody overnight at 4° C., followed by secondary HRP-conjugated antibodies for 1 hour at room temperature. Chemiluminescence was detected and imaged using enhanced ECL (Immun-Star WesternC; Bio-Rad) and Chemidoc XRS system (Bio-Rad).

Microarray

RNA was isolated using the RNeasy kit (Qiagen, Valencia, Calif.) and then hybridized to BD-103-0603 Illumina Beadchips. Raw data were subjected to Z-normalization, as previously described (C. Cheadle, M. P. Vawter, W. J. Freed, K. G. Becker, *Analysis of microarray data using Z score transformation. The Journal of molecular diagnostics: JMD* 5, 73 (May, 2003)). Principal component analysis, performed on the normalized Z-scores of all of the detectable probes in the samples, was performed by using the DIANE 6.0 software (http://www.grc.nia.nih.gov/branches/rrb/dna/diane_software.pdf). Significant genes were selected by the z-test <0.05, false discovery rate <0.30, as well as z-ratio >1.5 in both directions and ANOVA p value <0.05. Parametric analysis of gene set enrichment (PAGE) was analyzed as previously described (S. Y. Kim, D. J. Volsky, *PAGE: parametric analysis of gene set enrichment. BMC bioinformatics* 6, 144 (2005)). Gene regulatory network and canonic pathway analysis was performed using Ingenuity Pathways Analysis© (Ingenuity Systems; Redwood City, Calif.) (N=6).

Metabolomics

HEK293 cells were treated with MOTS-c (10 µM) or water (vehicle) for 24- and 72-hours. Also, HEK293 cells that were stably transfected with a validated MOTS-c expression vector, or empty vector (control) were used. Cells were cultured in 10-cm dishes in 7-mL of phenol-free DMEM supplemented with 10% FBS. For collection, cells were washed twice with ice-cold phosphate buffered saline (PBS) and immediately scraped, centrifuged, and snap frozen after aspiration supernatant. Frozen pellets were used for metabolomics analysis (Metabolon). The non-targeted metabolic profiling instrumentation employed a combination of three independent platforms: ultrahigh performance liquid chromatography/tandem mass spectrometry (UHPLC/MS/MS$^2$) optimized for basic species, UHPLC/MS/MS$^2$ optimized for acidic species, and gas chromatography/mass spectrometry (GC/MS). Samples were processed essentially as described previously (T. Ohta et al., *Untargeted metabolomic profiling as an evaluative tool of fenofibrate-induced toxicology in Fischer* 344 *male rats. Toxicologic pathology* 37, 521 (June, 2009) and A. M. Evans, C. D. DeHaven, T. Barrett, M. Mitchell, E. Milgram, *Integrated, nontargeted ultrahigh performance liquid chromatography/electrospray ionization tandem mass spectrometry platform for the identification and relative quantification of the small-molecule complement of biological systems. Analytical chemistry* 81, 6656 (Aug. 15, 2009)). In a minimum volume of water, cells were lysed using a Covaris adaptive focused acoustics E-series tissue disrupter/homogenizer. From the homogenate, a 100 µL aliquot was withdrawn for subsequent mass spectrometry and 25 µL used for measurement of total protein (Bradford Assay). Using an automated liquid handler (Hamilton LabStar, Salt Lake City, Utah), protein was precipitated from homogenate with methanol that contained four standards to report on extraction efficiency. The resulting supernatant was split into equal aliquots for analysis on the three platforms. Aliquots, dried under nitrogen and vacuum-desiccated, were subsequently either reconstituted in 50 µL 0.1% formic acid in water (acidic conditions) or in 50 µL 6.5 mM ammonium bicarbonate in water, pH 8 (basic conditions) for the two UHPLC/MS/MS$^2$ analyses or derivatized to a final volume of 50 µL for GC/MS analysis using equal parts bistrimethyl-silyl-trifluoroacetamide and solvent mixture acetonitrile:dichloromethane:cyclohexane (5:4:1) with 5% triethylamine at 60° C. for one hour. In addition, three types of controls were analyzed in concert with the experimental samples: aliquots of a sample derived from pooled experimental sample aliquots served as technical replicates throughout the data set, extracted water samples served as process blanks, and a cocktail of standards spiked into every analyzed sample allowed instrument performance monitoring. Experimental samples and controls were randomized across platform run days.

For UHLC/MS/MS$^2$ analysis, aliquots were separated using a Waters Acquity UPLC (Waters, Millford, Mass.) and analyzed using an LTQ mass spectrometer (Thermo Fisher Scientific, Inc., Waltham, Mass.) which consisted of an electrospray ionization (ESI) source and linear ion-trap (LIT) mass analyzer. The MS instrument scanned 99-1000 m/z and alternated between MS and MS$^2$ scans using dynamic exclusion with approximately 6 scans per second. Derivatized samples for GC/MS were separated on a 5% phenyldimethyl silicone column with helium as the carrier gas and a temperature ramp from 60° C. to 340° C. and then analyzed on a Thermo-Finnigan Trace DSQ MS (Thermo Fisher Scientific, Inc.) operated at unit mass resolving power with electron impact ionization and a 50-750 atomic mass unit scan range.

Metabolites were identified by automated comparison of the ion features in the experimental samples to a reference library of chemical standard entries that included retention time, molecular weight (m/z), preferred adducts, and in-source fragments as well as associated MS spectra, and were curated by visual inspection for quality control using software developed at Metabolon (C. D. Dehaven, A. M. Evans, H. Dai, K. A. Lawton, *Organization of GC/MS and LC/MS metabolomics data into chemical libraries. Journal of cheminformatics* 2, 9 (2010)).

For statistical analyses and data display purposes, any missing values were assumed to be below the limits of detection and these values were imputed with the compound minimum (minimum value imputation). In addition, each value was normalized to a total protein value on a per sample basis. Statistical analysis of log-transformed data was performed using "R" (http://cran.r-project.org/), which is a freely available, open-source software package. Student's t-test was performed to compare data between experimental groups.

Glucose and Lactate Assay

Extracellular glucose and lactate from cell culture medium was measured using glucose and D-lactate assay kits per manufacturer's instructions (Eton Bioscienes, USA). Intracellular glucose was determined by microscopy using 2-NBDG (Invitrogen, USA) per manufacturer's instructions.

Oxygen Consumption and Extracellular Acidification Rate

Real-time oxygen consumption rates (OCR) were measured using XF24/96 Extracellular Flux Analyzer (Seahorse Bioscience). ATP turnover, and maximum respiratory capacity was estimated by challenging cells with oligomycin and FCCP. Spare respiratory capacity was determined by 'maximum respiratory rate/basal respiratory rate', proton leakage by 'ATP turnover OCR−non-mitochondrial OCR (rotenone/antimycin A)', and coupling efficiency by '1−(ATP turnover OCR/Basal Respiratory rate)'. Glycolytic rate was determined using extracellular acidification rate (ECAR). Cell were stimulated with glucose to determine active glycolytic rate, and with oligomycin to determine maximum glycolytic capacity, and with 2-DG to determine glycolytic capacity.

Ex-vivo Soleus Muscle Strip Glucose Uptake

Whole muscle ex-vivo glucose uptake was assessed in mice 12 weeks of age using 2-deoxy glucose (Perkin Elmer) and 60 µl/ml human insulin (Novo Nordisk Pharmaceutical Industries), with minor changes to that described previously (V. Ribas et al., *Myeloid-specific estrogen receptor alpha deficiency impairs metabolic homeostasis and accelerates atherosclerotic lesion development. Proc Natl Acad Sci USA* 108, 16457 (Sep. 27, 2011) and C. E. McCurdy, G. D. Cartee, *Akt2 is essential for the full effect of calorie restriction on insulin-stimulated glucose uptake in skeletal muscle.*

*Diabetes* 54, 1349 (May, 2005)). Briefly, soleus and EDL muscles were carefully excised from anaesthetized animals and immediately incubated for 30 min in complete Krebs-Henseleit buffer with or without 60 µU/ml insulin at 35° C. Muscles were then transferred to the same buffer containing 3 mCi/ml $^3$H-2-deoxyglucose and 0.053 mCi/ml $^{14}$C-mannitol, and incubated for 20 min prior to snap freezing. Muscles were homogenized in lysis buffer and counted for radioactivity or subjected to western blotting. Glucose uptake was standardized to the non-specific uptake of mannitol and estimated as mmol of glucose uptake per gram soleus muscle.

Hyperinsulinemic-euglycemic Clamp Studies

Dual catheters were surgically placed in the right jugular vein and glucose clamp studies were performed 3 days post-surgery as previously described (V. Ribas et al., *Myeloid-specific estrogen receptor alpha deficiency impairs metabolic homeostasis and accelerates atherosclerotic lesion development. Proc Natl Acad Sci USA* 108, 16457 (Sep. 27, 2011); A. L. Hevener et al., *Muscle-specific Pparg deletion causes insulin resistance. Nature medicine* 9, 1491 (December, 2003); and A. L. Hevener et al., *Macrophage PPAR gamma is required for normal skeletal muscle and hepatic insulin sensitivity and full antidiabetic effects of thiazolidinediones. J Clin Invest* 117, 1658 (June, 2007)). All animals were fasted for 6 h and the final MOTS-c dose was administered 4 h prior to the clamp. Animals were studied in the conscious state. Basal glucose turnover was determined following a 90-minute constant infusion of (5.0 µCi/h, 0.12 ml/h) of [3-$^3$H] D-glucose (Perkin Elmer). After the basal period, glucose (50% dextrose, Abbott Laboratories) and insulin (8 mU/kg/min), Novo Nordisk Pharmaceutical Industries) plus tracer (5.0 µCi/h) infusions were initiated simultaneously, and glucose levels clamped at euglycemia using a variable glucose infusion rate (GIR). At steady state the total glucose disposal rate (GDR), measured by tracer dilution technique, is equal to the sum of the rate of endogenous or hepatic glucose production (HGP) and the exogenous (cold) glucose infusion rate (GIR)(A. L. Hevener et al., *Muscle-specific Pparg deletion causes insulin resistance. Nature medicine* 9, 1491 (December, 2003); A. L. Hevener et al., *Macrophage PPAR gamma is required for normal skeletal muscle and hepatic insulin sensitivity and full antidiabetic effects of thiazolidinediones. J Clin Invest* 117, 1658 (June, 2007); and R. Steele, *Influences of glucose loading and of injected insulin on hepatic glucose output. Ann N Y Acad Sci* 82, 420 (Sep. 25, 1959)). The insulin-stimulated component of the total GDR (IS-GDR) is equal to the total GDR minus the basal glucose turnover rate.

Glucose Tolerance Test (GTT)

Blood glucose was measured using a glucometer (Freestyle, Abbott). 12-week old male C57BL/6 mice were treated with MOTS-c (0.5 mg/kg/day; IP), or sterile pure water (vehicle), daily for 7 days. Then mice were injected with D-glucose (1 g/kg; IP) and blood was sampled from the tail at 0, 15, 30, 60, 90, and 120 minutes post-glucose injection.

The examples set forth above are provided to give those of ordinary skill in the art a complete disclosure and description of how to make and use the embodiments of the compositions, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated herein by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the disclosure is to be limited only by the terms of the appended claims, along with the full scope of equivalents to which the claims are entitled.

What is claimed is:

1. A method of treating diabetes, the method comprising administering to a subject in need thereof a therapeutically effective amount of a pharmaceutical composition comprising an isolated polypeptide or a pharmaceutically acceptable salt thereof comprising SEQ ID NO:1.

2. The method of claim 1, wherein the diabetes is type I diabetes.

3. The method of claim 1, wherein the diabetes is type II diabetes.

4. The method of claim 1, wherein the subject is a human.

5. The method of claim 1, wherein said pharmaceutical composition is formulated for unit dosage administration, wherein said isolated polypeptide is dosed from about 0.001 to about 1000 mg per day.

6. The method of claim 1, wherein said pharmaceutical composition is formulated for unit dosage administration, wherein said isolated polypeptide is dosed from about 0.01 to about 500 mg per day.

7. The method of claim 1, wherein said pharmaceutical composition is formulated for unit dosage administration, wherein said isolated polypeptide is dosed from about 0.5 to about 100 mg per day.

8. The method of claim 1, wherein said pharmaceutical composition is formulated as a sterile injectable solution.

9. The method of claim 1, wherein said pharmaceutical composition further comprises a pharmaceutically acceptable excipient.

* * * * *